(12) United States Patent
Avitable et al.

(10) Patent No.: US 9,387,146 B2
(45) Date of Patent: *Jul. 12, 2016

(54) COMPRESSION DEVICE HAVING WELD SEAM MOISTURE TRANSFER

(71) Applicant: Covidien LP, Mansfield, MA (US)

(72) Inventors: Raymond C Avitable, Framingham, MA (US); Jennie Brown, Providence, RI (US)

(73) Assignee: Covidien LP, Mansfield, MA (US)

( * ) Notice: Subject to any disclaimer, the term of this patent is extended or adjusted under 35 U.S.C. 154(b) by 741 days.

This patent is subject to a terminal disclaimer.

(21) Appl. No.: 13/858,314

(22) Filed: Apr. 8, 2013

(65) Prior Publication Data

US 2014/0135669 A1    May 15, 2014

Related U.S. Application Data

(63) Continuation of application No. 11/733,077, filed on Apr. 9, 2007, now Pat. No. 8,506,508.

(51) Int. Cl.
*A61H 9/00* (2006.01)
*A61F 13/08* (2006.01)

(52) U.S. Cl.
CPC ............... *A61H 9/00* (2013.01); *A61F 13/085* (2013.01); *A61H 9/0078* (2013.01); *A61H 9/0092* (2013.01); *A61H 2201/1697* (2013.01); *A61H 2205/10* (2013.01); *A61H 2205/106* (2013.01); *A61H 2205/108* (2013.01); *A61H 2209/00* (2013.01)

(58) Field of Classification Search
CPC ..... A61H 9/00; A61H 9/0092; A61H 9/0078; A61H 2209/00; A61H 2201/1697; A61H 2205/10; A61H 2205/108; A61H 2205/106; A61F 13/085; A61F 13/046; D04H 3/04; D04H 3/05

See application file for complete search history.

(56) References Cited

U.S. PATENT DOCUMENTS

| 908,959 | A | 1/1909 | Cooke |
|---|---|---|---|
| 910,689 | A | 1/1909 | Kelly et al. |
| 1,510,482 | A | 10/1924 | Kramer |
| 1,608,239 | A | 11/1926 | Rosett |
| 2,199,408 | A | 5/1940 | Liberte |
| 2,250,617 | A | 7/1941 | Argentin |
| 2,489,388 | A | 11/1949 | Rubin |
| 2,533,504 | A | 12/1950 | Poor |

(Continued)

FOREIGN PATENT DOCUMENTS

| CA | 2582678 A1 | 4/2006 |
|---|---|---|
| CN | 1009155 A | 1/1987 |

(Continued)

OTHER PUBLICATIONS

Office Action dated Oct. 6, 2014 in related U.S. Appl. No. 14/093,756, 7 pages.

(Continued)

*Primary Examiner* — Justine Yu
*Assistant Examiner* — Timothy Stanis

(57) ABSTRACT

A compression sleeve includes a wicking layer secured to bladder material defining an inflatable bladder along a seamline. Fibers of the wicking layer extend through the seamline to allow fluid wicked by the wicking layer from the wearer's skin to evaporate to the atmosphere.

17 Claims, 22 Drawing Sheets

(56) References Cited

U.S. PATENT DOCUMENTS

| | | |
|---|---|---|
| 2,638,915 A | 5/1953 | Mitchell |
| 2,676,587 A | 4/1954 | Corcoran |
| 2,694,395 A | 11/1954 | Brown |
| 2,853,998 A | 9/1958 | Emerson |
| 2,880,721 A | 4/1959 | Corcoran |
| 2,896,612 A | 7/1959 | Bates et al. |
| 2,998,817 A | 9/1961 | Armstrong |
| 3,164,152 A | 1/1965 | Nicoll |
| 3,245,405 A | 4/1966 | Gardner |
| 3,288,132 A | 11/1966 | Meredith |
| 3,351,055 A | 11/1967 | Gottfried |
| 3,454,010 A | 7/1969 | Lilligren et al. |
| 3,469,769 A | 9/1969 | Guenther |
| 3,473,527 A | 10/1969 | Spiro |
| 3,504,675 A | 4/1970 | Bishop, Jr. |
| 3,561,435 A | 2/1971 | Nicholson |
| 3,568,227 A | 3/1971 | Dunham |
| 3,606,880 A | 9/1971 | Ogle, Jr. |
| 3,638,334 A | 2/1972 | Malikowski |
| 3,701,173 A | 10/1972 | Whitney |
| 3,728,875 A | 4/1973 | Hartigan et al. |
| 3,760,795 A | 9/1973 | Adelhed |
| 3,770,040 A | 11/1973 | De Cicco |
| 3,771,519 A | 11/1973 | Haake |
| 3,786,805 A | 1/1974 | Tourin |
| 3,824,992 A | 7/1974 | Nicholson et al. |
| 3,826,249 A | 7/1974 | Lee et al. |
| 3,862,629 A | 1/1975 | Rotta |
| 3,868,952 A | 3/1975 | Hatton |
| 3,877,426 A | 4/1975 | Nirschl |
| 3,878,839 A | 4/1975 | Norton et al. |
| 3,899,210 A | 8/1975 | Samhammer et al. |
| 3,901,221 A | 8/1975 | Nicholson et al. |
| 3,906,937 A | 9/1975 | Aronson |
| 3,920,006 A | 11/1975 | Lapidus |
| D239,981 S | 5/1976 | Arluck et al. |
| 3,955,565 A | 5/1976 | Johnson, Jr. |
| 4,013,069 A | 3/1977 | Hasty |
| 4,029,087 A | 6/1977 | Dye et al. |
| 4,030,488 A | 6/1977 | Hasty |
| 4,054,129 A | 10/1977 | Byars et al. |
| 4,066,084 A | 1/1978 | Tillander |
| 4,076,022 A | 2/1978 | Walker |
| 4,091,804 A | 5/1978 | Hasty |
| 4,116,236 A | 9/1978 | Albert |
| 4,146,021 A | 3/1979 | Brosseau et al. |
| 4,149,529 A | 4/1979 | Copeland et al. |
| 4,149,541 A | 4/1979 | Gammons et al. |
| 4,153,050 A | 5/1979 | Bishop et al. |
| 4,156,425 A | 5/1979 | Arkans |
| 4,197,837 A | 4/1980 | Tringali et al. |
| 4,198,961 A | 4/1980 | Arkans |
| 4,201,203 A | 5/1980 | Applegate |
| 4,202,312 A | 5/1980 | Mori et al. |
| 4,202,325 A | 5/1980 | Villari et al. |
| 4,206,751 A | 6/1980 | Schneider |
| 4,207,875 A | 6/1980 | Arkans |
| 4,207,876 A | 6/1980 | Annis |
| 4,219,892 A | 9/1980 | Rigdon |
| 4,253,449 A | 3/1981 | Arkans et al. |
| D259,058 S | 4/1981 | Marshall |
| 4,267,611 A | 5/1981 | Agulnick |
| 4,270,527 A | 6/1981 | Peters et al. |
| 4,280,485 A | 7/1981 | Arkans |
| 4,294,238 A | 10/1981 | Woodford |
| 4,294,240 A | 10/1981 | Thill |
| 4,300,245 A | 11/1981 | Saunders |
| 4,308,862 A | 1/1982 | Kalmar |
| 4,311,135 A | 1/1982 | Brueckner et al. |
| 4,320,746 A | 3/1982 | Arkans et al. |
| 4,343,302 A | 8/1982 | Dillon |
| 4,351,872 A | 9/1982 | Brosseau et al. |
| 4,352,253 A | 10/1982 | Oswalt |
| 4,355,632 A | 10/1982 | Sandman |
| 4,363,125 A | 12/1982 | Brewer et al. |
| 4,372,297 A | 2/1983 | Perlin |
| 4,375,217 A | 3/1983 | Arkans et al. |
| 4,379,217 A | 4/1983 | Youmans |
| 4,402,312 A | 9/1983 | Villari et al. |
| 4,408,599 A | 10/1983 | Mummert |
| 4,417,587 A | 11/1983 | Ichinomiya et al. |
| 4,425,912 A | 1/1984 | Harper |
| 4,437,269 A | 3/1984 | Shaw |
| 4,442,834 A | 4/1984 | Tucker et al. |
| 4,445,505 A | 5/1984 | Labour et al. |
| 4,453,538 A | 6/1984 | Whitney |
| 4,522,197 A | 6/1985 | Hasegawa |
| 4,531,516 A | 7/1985 | Poole et al. |
| 4,547,906 A | 10/1985 | Nishida et al. |
| 4,547,919 A | 10/1985 | Wang |
| 4,552,821 A | 11/1985 | Gibbard et al. |
| 4,580,816 A | 4/1986 | Campbell et al. |
| 4,583,255 A | 4/1986 | Mogaki et al. |
| 4,593,692 A | 6/1986 | Flowers |
| 4,597,384 A | 7/1986 | Whitney |
| 4,614,179 A | 9/1986 | Gardner et al. |
| 4,614,180 A | 9/1986 | Gardner et al. |
| 4,624,244 A | 11/1986 | Taheri |
| 4,624,248 A | 11/1986 | Poole et al. |
| 4,650,452 A | 3/1987 | Jensen |
| 4,657,003 A | 4/1987 | Wirtz |
| 4,682,588 A | 7/1987 | Curlee |
| 4,696,289 A | 9/1987 | Gardner et al. |
| 4,699,424 A | 10/1987 | Andres et al. |
| 4,702,232 A | 10/1987 | Gardner et al. |
| 4,703,750 A | 11/1987 | Sebastian et al. |
| 4,706,658 A | 11/1987 | Cronin |
| 4,721,101 A | 1/1988 | Gardner et al. |
| 4,722,332 A | 2/1988 | Saggers |
| 4,730,606 A | 3/1988 | Leininger |
| 4,753,649 A | 6/1988 | Pazdernik |
| 4,762,121 A | 8/1988 | Shienfeld |
| 4,773,397 A | 9/1988 | Wright et al. |
| 4,805,620 A | 2/1989 | Meistrell |
| 4,809,684 A | 3/1989 | Gardner et al. |
| 4,827,912 A | 5/1989 | Carrington et al. |
| 4,832,010 A | 5/1989 | Lerman |
| RE32,939 E | 6/1989 | Gardner et al. |
| RE32,940 E | 6/1989 | Gardner et al. |
| 4,836,194 A | 6/1989 | Sebastian et al. |
| 4,836,691 A | 6/1989 | Suzuki et al. |
| 4,841,956 A | 6/1989 | Gardner et al. |
| D302,301 S | 7/1989 | Robinette-Lehman |
| 4,846,160 A | 7/1989 | Gardner et al. |
| 4,846,189 A | 7/1989 | Sun |
| 4,869,265 A | 9/1989 | McEwen |
| 4,872,448 A | 10/1989 | Johnson, Jr. |
| 4,876,788 A | 10/1989 | Steer et al. |
| 4,883,073 A | 11/1989 | Aziz |
| 4,886,053 A | 12/1989 | Neal |
| 4,898,160 A | 2/1990 | Brownlee |
| 4,913,136 A | 4/1990 | Chong et al. |
| 4,938,207 A | 7/1990 | Vargo |
| 4,938,208 A | 7/1990 | Dye |
| 4,938,226 A | 7/1990 | Danielsson et al. |
| 4,945,571 A | 8/1990 | Calvert |
| 4,947,834 A | 8/1990 | Kartheus et al. |
| 4,957,105 A | 9/1990 | Kurth |
| 4,960,115 A | 10/1990 | Ranciato |
| 4,964,402 A | 10/1990 | Grim et al. |
| 4,979,953 A | 12/1990 | Spence |
| 4,985,024 A | 1/1991 | Sipinen |
| 4,989,273 A | 2/1991 | Cromartie |
| 4,997,452 A | 3/1991 | Kovach et al. |
| 5,007,411 A | 4/1991 | Dye |
| 5,014,681 A | 5/1991 | Heeman et al. |
| 5,022,387 A | 6/1991 | Hasty |
| 5,031,604 A | 7/1991 | Dye |
| 5,048,536 A | 9/1991 | McEwen |
| 5,052,377 A | 10/1991 | Frajdenrajch |
| 5,062,414 A | 11/1991 | Grim |
| 5,069,219 A | 12/1991 | Knoblich |
| 5,071,415 A | 12/1991 | Takemoto |
| 5,080,951 A | 1/1992 | Guthrie |

(56) References Cited

U.S. PATENT DOCUMENTS

| | | |
|---|---|---|
| 5,082,284 A | 1/1992 | Reed |
| 5,109,832 A | 5/1992 | Proctor et al. |
| 5,117,812 A | 6/1992 | McWhorter |
| 5,120,300 A | 6/1992 | Shaw |
| 5,135,473 A | 8/1992 | Epler et al. |
| 5,139,475 A | 8/1992 | Robicsek |
| 5,139,476 A | 8/1992 | Peters |
| 5,139,479 A | 8/1992 | Peters |
| 5,146,932 A | 9/1992 | McCabe |
| 5,156,629 A | 10/1992 | Shane et al. |
| 5,158,541 A | 10/1992 | McCurley |
| 5,168,576 A | 12/1992 | Krent et al. |
| 5,172,689 A | 12/1992 | Wright |
| D332,495 S | 1/1993 | Lake |
| 5,179,941 A | 1/1993 | Siemssen et al. |
| 5,181,522 A | 1/1993 | McEwen |
| 5,186,163 A | 2/1993 | Dye |
| 5,193,549 A | 3/1993 | Bellin et al. |
| 5,211,162 A | 5/1993 | Gillen, Jr. et al. |
| 5,226,245 A | 7/1993 | Lamont |
| 5,226,564 A | 7/1993 | Steer et al. |
| 5,228,478 A | 7/1993 | Kleisle |
| 5,230,335 A | 7/1993 | Johnson, Jr. et al. |
| 5,245,990 A | 9/1993 | Bertinin |
| 5,259,397 A | 11/1993 | McCabe |
| 5,261,871 A | 11/1993 | Greenfield |
| 5,263,473 A | 11/1993 | McWhorter |
| 5,275,588 A | 1/1994 | Matsumoto et al. |
| 5,277,695 A | 1/1994 | Johnson, Jr. et al. |
| 5,277,697 A | 1/1994 | France et al. |
| 5,288,286 A | 2/1994 | Davis |
| 5,312,431 A | 5/1994 | McEwen |
| 5,314,455 A | 5/1994 | Johnson, Jr. et al. |
| 5,334,135 A | 8/1994 | Grim et al. |
| 5,342,285 A | 8/1994 | Dye |
| 5,354,260 A | 10/1994 | Cook |
| 5,378,224 A | 1/1995 | Billotti |
| 5,383,894 A | 1/1995 | Dye |
| 5,383,919 A | 1/1995 | Kelly et al. |
| 5,385,538 A | 1/1995 | Mann |
| 5,389,065 A | 2/1995 | Johnson, Jr. |
| 5,391,141 A | 2/1995 | Hamilton |
| 5,399,153 A | 3/1995 | Caprio, Jr. et al. |
| 5,403,265 A | 4/1995 | Berguer et al. |
| 5,406,661 A | 4/1995 | Pekar |
| 5,407,421 A | 4/1995 | Goldsmith |
| D358,216 S | 5/1995 | Dye |
| 5,413,142 A | 5/1995 | Johnson et al. |
| 5,413,582 A | 5/1995 | Eaton |
| 5,419,757 A | 5/1995 | Daneshvar |
| 5,425,701 A | 6/1995 | Oster et al. |
| 5,435,009 A | 7/1995 | Schild et al. |
| 5,437,595 A | 8/1995 | Smith |
| 5,437,610 A | 8/1995 | Cariapa et al. |
| 5,441,533 A | 8/1995 | Johnson et al. |
| 5,443,440 A | 8/1995 | Tumey et al. |
| 5,449,341 A | 9/1995 | Harris |
| 5,449,379 A | 9/1995 | Hadtke |
| 5,450,858 A | 9/1995 | Zablotsky et al. |
| 5,451,201 A | 9/1995 | Prengler |
| 5,453,081 A | 9/1995 | Hansen |
| 5,455,969 A | 10/1995 | Pratson et al. |
| 5,458,265 A | 10/1995 | Hester et al. |
| 5,462,517 A | 10/1995 | Mann |
| 5,466,250 A | 11/1995 | Johnson, Jr. et al. |
| 5,470,156 A | 11/1995 | May |
| 5,478,119 A | 12/1995 | Dye |
| 5,489,252 A | 2/1996 | May |
| 5,489,259 A | 2/1996 | Jacobs et al. |
| 5,496,262 A | 3/1996 | Johnson, Jr. et al. |
| 5,503,620 A | 4/1996 | Danzger |
| 5,511,552 A | 4/1996 | Johnson |
| 5,513,658 A | 5/1996 | Goseki |
| 5,514,081 A | 5/1996 | Mann |
| 5,514,155 A | 5/1996 | Daneshvar |
| 5,527,267 A | 6/1996 | Billotti |
| 5,554,105 A | 9/1996 | Taylor |
| D376,013 S | 11/1996 | Sandman et al. |
| 5,575,762 A | 11/1996 | Peeler et al. |
| 5,578,055 A | 11/1996 | McEwen |
| 5,584,798 A | 12/1996 | Fox |
| 5,588,954 A | 12/1996 | Ribando et al. |
| 5,588,955 A | 12/1996 | Johnson, Jr. et al. |
| 5,588,956 A | 12/1996 | Billotti |
| 5,591,200 A | 1/1997 | Cone et al. |
| 5,591,337 A | 1/1997 | Lynn et al. |
| 5,603,690 A | 2/1997 | Barry |
| 5,609,570 A | 3/1997 | Lamont |
| 5,620,411 A | 4/1997 | Schumann et al. |
| 5,622,113 A | 4/1997 | Hansen |
| 5,626,556 A | 5/1997 | Tobler et al. |
| 5,626,557 A | 5/1997 | Mann |
| 5,634,889 A | 6/1997 | Gardner et al. |
| 5,637,106 A | 6/1997 | Mitchell et al. |
| 5,640,714 A | 6/1997 | Tanaka |
| 5,649,954 A | 7/1997 | McEwen |
| 5,653,244 A | 8/1997 | Shaw |
| D383,547 S | 9/1997 | Mason et al. |
| 5,664,270 A | 9/1997 | Bell et al. |
| 5,669,872 A | 9/1997 | Fox |
| 5,673,028 A | 9/1997 | Levy |
| 5,674,262 A | 10/1997 | Tumey |
| 5,678,558 A | 10/1997 | Johnson |
| 5,695,453 A | 12/1997 | Neal |
| 5,704,999 A | 1/1998 | Lukich et al. |
| 5,711,757 A | 1/1998 | Bryant |
| 5,711,760 A | 1/1998 | Ibrahim et al. |
| 5,717,996 A | 2/1998 | Feldmann |
| 5,720,739 A | 2/1998 | Hilston et al. |
| 5,725,485 A | 3/1998 | Ribando et al. |
| 5,728,055 A | 3/1998 | Sebastian |
| 5,728,057 A | 3/1998 | Ouellette et al. |
| 5,730,710 A | 3/1998 | Eichhorn et al. |
| 5,733,304 A | 3/1998 | Spence |
| 5,741,295 A | 4/1998 | McEwen |
| 5,746,213 A | 5/1998 | Marks |
| 5,759,167 A | 6/1998 | Shields et al. |
| 5,765,298 A | 6/1998 | Potter et al. |
| 5,769,800 A | 6/1998 | Gelfand et al. |
| 5,769,801 A | 6/1998 | Tumey et al. |
| 5,772,880 A | 6/1998 | Lynn et al. |
| 5,790,998 A | 8/1998 | Crescimbeni |
| 5,795,312 A | 8/1998 | Dye |
| 5,797,851 A | 8/1998 | Byrd |
| 5,823,981 A | 10/1998 | Grim et al. |
| 5,830,164 A | 11/1998 | Cone et al. |
| 5,833,639 A | 11/1998 | Nunes et al. |
| 5,840,049 A | 11/1998 | Tumey et al. |
| 5,843,007 A | 12/1998 | McEwen et al. |
| D403,775 S | 1/1999 | Davis et al. |
| D405,884 S | 2/1999 | Roper |
| 5,876,359 A | 3/1999 | Bock et al. |
| 5,891,065 A | 4/1999 | Cariapa et al. |
| 5,894,682 A | 4/1999 | Broz |
| D411,301 S | 6/1999 | Hampson et al. |
| 5,916,183 A | 6/1999 | Reid |
| 5,925,010 A | 7/1999 | Caprio, Jr. |
| 5,926,850 A | 7/1999 | Han |
| 5,931,797 A | 8/1999 | Tumey et al. |
| 5,938,628 A | 8/1999 | Oguri et al. |
| 5,951,502 A | 9/1999 | Peeler et al. |
| 5,957,872 A | 9/1999 | Flick |
| 5,966,763 A | 10/1999 | Thomas et al. |
| 5,968,072 A | 10/1999 | Hite et al. |
| 5,970,519 A | 10/1999 | Weber |
| 5,976,099 A | 11/1999 | Kellogg |
| 5,976,300 A | 11/1999 | Buchanan et al. |
| 5,988,704 A | 11/1999 | Ryhman |
| 5,989,204 A | 11/1999 | Lina |
| 5,991,654 A | 11/1999 | Tumey et al. |
| 5,997,495 A | 12/1999 | Cook et al. |
| 5,997,981 A | 12/1999 | McCormack et al. |
| 6,001,119 A | 12/1999 | Hampson et al. |
| 6,007,559 A | 12/1999 | Arkans |

(56) References Cited

U.S. PATENT DOCUMENTS

| | | |
|---|---|---|
| 6,010,471 A | 1/2000 | Ben-Noon |
| 6,021,780 A | 2/2000 | Darby |
| 6,036,718 A | 3/2000 | Ledford et al. |
| 6,048,326 A | 4/2000 | Davis et al. |
| 6,051,016 A | 4/2000 | Mesaros et al. |
| 6,056,713 A | 5/2000 | Hayashi |
| 6,062,244 A | 5/2000 | Arkans |
| 6,066,217 A | 5/2000 | Dibble et al. |
| 6,076,193 A | 6/2000 | Hood |
| 6,080,120 A | 6/2000 | Sandman et al. |
| D428,153 S | 7/2000 | Davis |
| 6,110,135 A | 8/2000 | Madow et al. |
| 6,120,469 A | 9/2000 | Bruder |
| 6,126,683 A | 10/2000 | Momtaheni |
| 6,129,688 A | 10/2000 | Arkans |
| 6,129,695 A | 10/2000 | Peters et al. |
| 6,134,720 A | 10/2000 | Foreman |
| 6,135,116 A | 10/2000 | Vogel et al. |
| 6,145,143 A | 11/2000 | Hicks et al. |
| 6,149,600 A | 11/2000 | Poorman-Ketchum |
| 6,149,616 A | 11/2000 | Szlema et al. |
| 6,152,495 A | 11/2000 | Hoffmann et al. |
| 6,152,893 A | 11/2000 | Pigg et al. |
| 6,168,539 B1 | 1/2001 | Maina |
| 6,171,271 B1 | 1/2001 | Hörnberg |
| 6,179,796 B1 | 1/2001 | Waldridge |
| 6,197,045 B1 | 3/2001 | Carson |
| 6,203,510 B1 | 3/2001 | Takeuchi et al. |
| 6,209,159 B1 | 4/2001 | Murphy |
| 6,212,719 B1 | 4/2001 | Thomas et al. |
| 6,227,275 B1 | 5/2001 | Dibble et al. |
| 6,231,507 B1 | 5/2001 | Zikorus et al. |
| 6,231,532 B1 | 5/2001 | Watson et al. |
| 6,245,023 B1 | 6/2001 | Clemmons |
| 6,254,554 B1 | 7/2001 | Turtzo |
| 6,257,626 B1 | 7/2001 | Campau |
| 6,257,627 B1 | 7/2001 | Fujiwara et al. |
| 6,260,201 B1 | 7/2001 | Rankin |
| 6,273,866 B2 | 8/2001 | Thomas et al. |
| 6,290,662 B1 | 9/2001 | Morris et al. |
| 6,290,664 B1 | 9/2001 | Nauert |
| 6,296,617 B1 | 10/2001 | Peeler et al. |
| 6,315,745 B1 | 11/2001 | Kloecker |
| 6,319,215 B1 | 11/2001 | Manor et al. |
| 6,322,530 B1 | 11/2001 | Johnson, Jr. et al. |
| 6,336,935 B1 | 1/2002 | Davis et al. |
| 6,338,723 B1 | 1/2002 | Carpenter et al. |
| 6,349,506 B1 | 2/2002 | Pace et al. |
| 6,358,219 B1 | 3/2002 | Arkans |
| 6,361,496 B1 | 3/2002 | Zikorus et al. |
| 6,368,357 B1 | 4/2002 | Schon et al. |
| 6,375,633 B1 | 4/2002 | Endress et al. |
| 6,385,778 B1 | 5/2002 | Johnson |
| 6,385,864 B1 | 5/2002 | Sell, Jr. et al. |
| 6,387,065 B1 | 5/2002 | Tumey |
| 6,402,879 B1 | 6/2002 | Tawney et al. |
| 6,409,691 B1 | 6/2002 | Dakin et al. |
| 6,421,859 B1 | 7/2002 | Hicks et al. |
| 6,423,053 B1 | 7/2002 | Lee |
| 6,436,064 B1 | 8/2002 | Kloecker |
| 6,440,093 B1 | 8/2002 | McEwen et al. |
| 6,447,460 B1 | 9/2002 | Zheng et al. |
| 6,447,467 B1 | 9/2002 | Barak |
| 6,463,934 B1 | 10/2002 | Johnson, Jr. et al. |
| 6,468,237 B1 | 10/2002 | Lina |
| 6,478,757 B1 | 11/2002 | Barak |
| 6,478,761 B2 | 11/2002 | Bracamonte-Sommer |
| 6,488,643 B1 | 12/2002 | Tumey et al. |
| 6,493,568 B1 | 12/2002 | Bell et al. |
| 6,494,852 B1 | 12/2002 | Barak et al. |
| 6,508,205 B1 | 1/2003 | Zink |
| 6,520,926 B2 | 2/2003 | Hall |
| 6,526,597 B1 | 3/2003 | Shepard |
| 6,527,727 B2 | 3/2003 | Itonaga et al. |
| 6,537,298 B2 | 3/2003 | Dedo |
| 6,540,707 B1 | 4/2003 | Stark et al. |
| 6,544,202 B2 | 4/2003 | McEwen et al. |
| 6,549,748 B2 | 4/2003 | Miura |
| 6,551,280 B1 | 4/2003 | Knighton et al. |
| 6,554,785 B1 | 4/2003 | Sroufe et al. |
| 6,557,704 B1 | 5/2003 | Randolph |
| 6,558,338 B1 | 5/2003 | Wasserman |
| 6,562,060 B1 | 5/2003 | Momtaheni |
| 6,589,267 B1 | 7/2003 | Hui |
| 6,589,534 B1 | 7/2003 | Shaul et al. |
| 6,592,534 B1 | 7/2003 | Rutt et al. |
| 6,593,508 B1 | 7/2003 | Harder |
| 6,598,249 B2 | 7/2003 | Pajanacci et al. |
| D478,995 S | 8/2003 | Cipra et al. |
| 6,616,622 B1 | 9/2003 | Barberio |
| 6,618,859 B1 | 9/2003 | Kadymir et al. |
| 6,629,941 B1 | 10/2003 | Ishibashi et al. |
| 6,645,165 B2 | 11/2003 | Waldridge et al. |
| D484,986 S | 1/2004 | Cipra et al. |
| 6,676,614 B1 | 1/2004 | Hansen et al. |
| 6,682,547 B2 | 1/2004 | McEwen et al. |
| 6,685,661 B2 | 2/2004 | Peled |
| 6,719,711 B1 | 4/2004 | Islava |
| 6,726,641 B2 | 4/2004 | Chiang et al. |
| 6,746,470 B2 | 6/2004 | McEwen et al. |
| 6,757,516 B2 | 6/2004 | Miura |
| 6,762,337 B2 | 7/2004 | Boukanov et al. |
| 6,762,338 B2 | 7/2004 | Harder |
| 6,842,915 B2 | 1/2005 | Turner et al. |
| 6,846,294 B2 | 1/2005 | Rastegar et al. |
| 6,846,295 B1 | 1/2005 | Ben-Nun |
| 6,849,057 B2 | 2/2005 | Satou et al. |
| 6,852,089 B2 | 2/2005 | Kloecker et al. |
| 6,860,862 B2 | 3/2005 | Waldridge et al. |
| 6,862,989 B2 | 3/2005 | Belanger et al. |
| 6,866,636 B2 | 3/2005 | Inoue et al. |
| 6,869,409 B2 | 3/2005 | Rothman et al. |
| D506,553 S | 6/2005 | Tesluk |
| 6,945,944 B2 | 9/2005 | Kuiper et al. |
| D510,626 S | 10/2005 | Krahner et al. |
| 6,966,884 B2 | 11/2005 | Waldridge et al. |
| 6,973,690 B2 | 12/2005 | Muci et al. |
| 6,984,215 B2 | 1/2006 | Shah et al. |
| 6,991,613 B2 | 1/2006 | Sensabaugh |
| 7,011,640 B2 | 3/2006 | Patterson et al. |
| 7,022,096 B1 | 4/2006 | Alfieri |
| 7,041,074 B1 | 5/2006 | Averianov et al. |
| 7,044,924 B1 | 5/2006 | Roth et al. |
| 7,048,703 B2 | 5/2006 | Riach |
| 7,063,676 B2 | 6/2006 | Barak et al. |
| 7,090,500 B1 | 8/2006 | Guttman |
| 7,104,967 B2 | 9/2006 | Rothman et al. |
| D533,668 S | 12/2006 | Brown |
| 7,166,077 B2 | 1/2007 | Millay et al. |
| 7,214,202 B1 | 5/2007 | Vogel et al. |
| 7,217,249 B2 | 5/2007 | Scott |
| D545,972 S | 7/2007 | Wieringa et al. |
| 7,237,272 B2 | 7/2007 | Botcher |
| 7,238,080 B2 | 7/2007 | Gimble |
| 7,244,483 B2 | 7/2007 | Tawney et al. |
| 7,258,676 B2 | 8/2007 | Calderon et al. |
| D550,367 S | 9/2007 | Nash |
| 7,276,037 B2 | 10/2007 | Ravikumar |
| 7,276,039 B2 | 10/2007 | Garelick et al. |
| 7,278,980 B1 | 10/2007 | Garelick et al. |
| 7,282,038 B2 | 10/2007 | Gillis et al. |
| 7,285,103 B2 | 10/2007 | Nathanson |
| 7,288,076 B2 | 10/2007 | Grim et al. |
| 7,297,128 B2 | 11/2007 | Binder et al. |
| 7,300,410 B1 | 11/2007 | Weber |
| 7,303,539 B2 | 12/2007 | Binder et al. |
| 7,306,568 B2 | 12/2007 | Diana |
| 7,310,847 B2 | 12/2007 | Bolkan et al. |
| 7,318,812 B2 | 1/2008 | Taylor et al. |
| D562,461 S | 2/2008 | Nash |
| D562,462 S | 2/2008 | Muir et al. |
| 7,326,227 B2 | 2/2008 | Dedo et al. |
| 7,329,232 B2 | 2/2008 | Lipshaw et al. |
| 7,351,217 B2 | 4/2008 | Scherpenborg |

(56) References Cited

U.S. PATENT DOCUMENTS

| | | |
|---|---|---|
| 7,353,770 B2 | 4/2008 | Sanguinetti |
| 7,354,410 B2 | 4/2008 | Perry et al. |
| 7,354,411 B2 | 4/2008 | Perry et al. |
| 7,374,550 B2 | 5/2008 | Hansen et al. |
| D577,124 S | 9/2008 | Freeland et al. |
| 7,424,936 B2 | 9/2008 | McClellan |
| 7,442,175 B2 | 10/2008 | Meyer et al. |
| D580,553 S | 11/2008 | Nash |
| 7,465,283 B2 | 12/2008 | Grim et al. |
| 7,468,048 B2 | 12/2008 | Meehan |
| 7,473,816 B2 | 1/2009 | Hall |
| D594,561 S | 6/2009 | Freeland et al. |
| 7,543,399 B2 | 6/2009 | Kilgore et al. |
| 7,556,707 B2 | 7/2009 | Giori |
| 7,559,908 B2 | 7/2009 | Ravikumar |
| 7,578,799 B2 | 8/2009 | Thorsteinsson et al. |
| 7,591,796 B1 | 9/2009 | Barak et al. |
| 7,591,797 B2 | 9/2009 | Hakonson et al. |
| 7,597,675 B2 | 10/2009 | Ingimundarson et al. |
| 7,615,027 B2 | 11/2009 | Nordt, III et al. |
| 7,618,384 B2 | 11/2009 | Nardi et al. |
| 7,618,389 B2 | 11/2009 | Nordt, III et al. |
| 7,625,348 B2 | 12/2009 | Young et al. |
| 7,637,879 B2 | 12/2009 | Barak et al. |
| D608,006 S | 1/2010 | Avitable et al. |
| 7,654,117 B2 | 2/2010 | Barnett |
| 7,670,306 B2 | 3/2010 | Nordt, III et al. |
| 7,691,084 B2 | 4/2010 | Knighton et al. |
| 7,748,090 B2 | 7/2010 | Seth et al. |
| 7,749,182 B2 | 7/2010 | Gramza et al. |
| 7,758,607 B2 | 7/2010 | McEwen et al. |
| 7,766,890 B2 | 8/2010 | Ito et al. |
| 7,771,376 B2 | 8/2010 | Roth et al. |
| 7,780,614 B2 | 8/2010 | Bruce et al. |
| 7,780,698 B2 | 8/2010 | McEwen et al. |
| 7,803,358 B2 | 9/2010 | Gordan et al. |
| 7,827,624 B1 | 11/2010 | Cole |
| 7,871,387 B2 | 1/2011 | Tordella et al. |
| 7,874,997 B2 | 1/2011 | Jaccard |
| 7,882,568 B2 | 2/2011 | Fee |
| 7,931,606 B2 | 4/2011 | Meyer |
| 7,967,766 B2 | 6/2011 | Ravikumar |
| 7,976,487 B2 | 7/2011 | Gramza et al. |
| 8,002,721 B2 | 8/2011 | Bretl et al. |
| 8,016,778 B2 | 9/2011 | Brown et al. |
| 8,016,779 B2 | 9/2011 | Brown et al. |
| 8,021,388 B2 | 9/2011 | Brown et al. |
| 8,029,450 B2 | 10/2011 | Brown et al. |
| 8,029,451 B2 | 10/2011 | Meyer et al. |
| 8,034,007 B2 | 10/2011 | Avitable et al. |
| 8,034,013 B2 | 10/2011 | Winkler |
| 8,070,699 B2 | 12/2011 | Avitable et al. |
| 8,109,892 B2 | 2/2012 | Brown et al. |
| 8,114,117 B2 | 2/2012 | Avitable |
| 8,128,584 B2 | 3/2012 | Brown |
| 8,177,734 B2 | 5/2012 | Vess |
| 8,235,923 B2 | 8/2012 | Avitable et al. |
| 8,419,666 B2 | 4/2013 | Liu et al. |
| 2001/0018564 A1 | 8/2001 | Manor et al. |
| 2002/0042585 A1 | 4/2002 | Kloecker |
| 2002/0068886 A1 | 6/2002 | Lin |
| 2002/0069731 A1 | 6/2002 | Soucy |
| 2002/0115949 A1 | 8/2002 | Kuslich et al. |
| 2002/0121235 A1 | 9/2002 | Carpenter et al. |
| 2003/0018313 A1 | 1/2003 | Tanzer et al. |
| 2003/0083605 A1 | 5/2003 | Edmund |
| 2003/0130644 A1 | 7/2003 | Baker |
| 2003/0139255 A1 | 7/2003 | Lina |
| 2003/0199922 A1 | 10/2003 | Buckman |
| 2004/0010212 A1 | 1/2004 | Kuiper et al. |
| 2004/0039317 A1 | 2/2004 | Souney et al. |
| 2004/0039413 A1 | 2/2004 | Akerfeldt et al. |
| 2004/0054306 A1 | 3/2004 | Roth et al. |
| 2004/0068290 A1 | 4/2004 | Bates et al. |
| 2004/0097860 A1 | 5/2004 | Tauber |
| 2004/0158283 A1 | 8/2004 | Shook et al. |
| 2004/0158285 A1 | 8/2004 | Pillai |
| 2004/0176715 A1 | 9/2004 | Nelson |
| 2004/0181156 A1 | 9/2004 | Kingsford et al. |
| 2004/0181254 A1 | 9/2004 | Choi et al. |
| 2004/0199090 A1 | 10/2004 | Sanders et al. |
| 2004/0210167 A1 | 10/2004 | Webster |
| 2004/0236258 A1 | 11/2004 | Burns et al. |
| 2005/0070828 A1 | 3/2005 | Hampson et al. |
| 2005/0143683 A1 | 6/2005 | Waldridge et al. |
| 2005/0154336 A1 | 7/2005 | Kloecker et al. |
| 2005/0187503 A1 | 8/2005 | Tordella et al. |
| 2005/0209545 A1 | 9/2005 | Farrow et al. |
| 2005/0242315 A1 | 11/2005 | Lund |
| 2006/0010574 A1 | 1/2006 | Linnane et al. |
| 2006/0020236 A1 | 1/2006 | Ben-Nun |
| 2006/0026736 A1 | 2/2006 | Nordt et al. |
| 2006/0089617 A1 | 4/2006 | Bunnelle |
| 2006/0102423 A1 | 5/2006 | Lang et al. |
| 2006/0135894 A1 | 6/2006 | G. Linnane et al. |
| 2006/0137072 A1 | 6/2006 | Visco et al. |
| 2006/0142719 A1 | 6/2006 | Vogt et al. |
| 2006/0161081 A1 | 7/2006 | Barak et al. |
| 2006/0189907 A1 | 8/2006 | Pick et al. |
| 2006/0211965 A1 | 9/2006 | Horn et al. |
| 2006/0287672 A1 | 12/2006 | McEwen et al. |
| 2006/0293151 A1 | 12/2006 | Rast |
| 2007/0038167 A1 | 2/2007 | Tabron et al. |
| 2007/0055188 A1 | 3/2007 | Avni et al. |
| 2007/0129658 A1 | 6/2007 | Hampson et al. |
| 2007/0130732 A1 | 6/2007 | Matsumura et al. |
| 2007/0135835 A1 | 6/2007 | McEwen et al. |
| 2007/0135836 A1 | 6/2007 | McEwen et al. |
| 2007/0179416 A1 | 8/2007 | Obrien et al. |
| 2007/0197947 A1 | 8/2007 | Scott |
| 2007/0260162 A1 | 11/2007 | Meyer et al. |
| 2007/0264497 A1 | 11/2007 | Kong |
| 2007/0276310 A1 | 11/2007 | Lipshaw et al. |
| 2007/0276311 A1 | 11/2007 | Wieringa et al. |
| 2007/0282233 A1 | 12/2007 | Meyer et al. |
| 2008/0000477 A1 | 1/2008 | Huster et al. |
| 2008/0004555 A1 | 1/2008 | Reis et al. |
| 2008/0004560 A1 | 1/2008 | Miskie |
| 2008/0023423 A1 | 1/2008 | Duffy |
| 2008/0071204 A1 | 3/2008 | Linnane et al. |
| 2008/0072629 A1 | 3/2008 | Gehring |
| 2008/0082029 A1 | 4/2008 | Diana |
| 2008/0086071 A1 | 4/2008 | Weatherly |
| 2008/0087740 A1 | 4/2008 | Gusenoff et al. |
| 2008/0103397 A1 | 5/2008 | Barak |
| 2008/0103422 A1 | 5/2008 | Perry et al. |
| 2008/0141428 A1 | 6/2008 | Kapah et al. |
| 2008/0143007 A1 | 6/2008 | Tuma |
| 2008/0183115 A1 | 7/2008 | Pierce |
| 2008/0188786 A1 | 8/2008 | Hickling |
| 2008/0208092 A1 | 8/2008 | Sawa |
| 2008/0234615 A1 | 9/2008 | Cook et al. |
| 2008/0243173 A1 | 10/2008 | Thorpe |
| 2008/0245361 A1 | 10/2008 | Brown |
| 2008/0249440 A1 | 10/2008 | Avitable et al. |
| 2008/0249441 A1 | 10/2008 | Avitable et al. |
| 2008/0249443 A1 | 10/2008 | Avitable et al. |
| 2008/0249449 A1 | 10/2008 | Brown et al. |
| 2008/0249559 A1 | 10/2008 | Brown et al. |
| 2008/0250551 A1 | 10/2008 | Mazzarolo |
| 2008/0255485 A1 | 10/2008 | Johnson et al. |
| 2008/0281351 A1 | 11/2008 | Croushorn et al. |
| 2008/0306420 A1 | 12/2008 | Vess |
| 2008/0312682 A1 | 12/2008 | Shams et al. |
| 2009/0005718 A1 | 1/2009 | Lightbourne |
| 2009/0064919 A1 | 3/2009 | Greenwald |
| 2009/0082708 A1 | 3/2009 | Scott et al. |
| 2009/0099562 A1 | 4/2009 | Ingimudarson et al. |
| 2009/0110890 A1 | 4/2009 | Garza et al. |
| 2009/0124944 A1 | 5/2009 | Ravikumar |
| 2009/0133446 A1 | 5/2009 | Burrow et al. |
| 2009/0137938 A1 | 5/2009 | Parivash |
| 2009/0163842 A1 | 6/2009 | Cropper |
| 2009/0171223 A1 | 7/2009 | McEwen et al. |

(56) References Cited

U.S. PATENT DOCUMENTS

| | | |
|---|---|---|
| 2009/0198160 A1 | 8/2009 | Coyne |
| 2009/0198261 A1 | 8/2009 | Schweikert |
| 2009/0227917 A1 | 9/2009 | Nardi |
| 2009/0227919 A1 | 9/2009 | Nardi et al. |
| 2009/0227922 A1 | 9/2009 | Nardi et al. |
| 2009/0234265 A1 | 9/2009 | Reid, Jr. et al. |
| 2009/0270910 A1 | 10/2009 | Hargens et al. |
| 2009/0278707 A1 | 11/2009 | Biggins et al. |
| 2009/0281470 A1 | 11/2009 | Sandusky et al. |
| 2009/0299249 A1 | 12/2009 | Wilkes et al. |
| 2009/0312681 A1 | 12/2009 | McSpadden et al. |
| 2009/0320174 A1 | 12/2009 | Turner |
| 2009/0326576 A1 | 12/2009 | Ben-Nun |
| 2010/0004575 A1 | 1/2010 | Vess |
| 2010/0004676 A1 | 1/2010 | McEwen et al. |
| 2010/0010408 A1 | 1/2010 | Linares |
| 2010/0016771 A1 | 1/2010 | Arbesman et al. |
| 2010/0022930 A1 | 1/2010 | Koby et al. |
| 2010/0037369 A1 | 2/2010 | Reichert |
| 2010/0042026 A1 | 2/2010 | Kloecker et al. |
| 2010/0042028 A1 | 2/2010 | Frank et al. |
| 2010/0081974 A1 | 4/2010 | Vess |
| 2010/0081975 A1 | 4/2010 | Avitable et al. |
| 2010/0081977 A1 | 4/2010 | Vess |
| 2010/0210982 A1 | 8/2010 | Balachandran et al. |
| 2010/0268130 A1 | 10/2010 | Khan |
| 2012/0071801 A1 | 3/2012 | Avitable |
| 2012/0078146 A1 | 3/2012 | Deshpande |
| 2013/0184623 A1 | 7/2013 | Fraser |
| 2013/0310719 A1 | 11/2013 | Davis et al. |
| 2014/0236058 A1 | 8/2014 | Lee |

FOREIGN PATENT DOCUMENTS

| | | |
|---|---|---|
| DE | 19846922 A1 | 10/2011 |
| EP | 0221636 A1 | 5/1987 |
| EP | 0303029 A1 | 2/1989 |
| EP | 0408049 A2 | 1/1991 |
| EP | 0861651 A1 | 9/1998 |
| EP | 0893115 A2 | 1/1999 |
| EP | 1468816 A1 | 10/2004 |
| EP | 1980228 A2 | 10/2008 |
| FR | 2813770 A1 | 3/2002 |
| FR | 2950245 A1 | 9/2009 |
| GB | 2061086 A | 5/1981 |
| GB | 2178663 A | 2/1987 |
| GB | 2183483 A | 6/1987 |
| GB | 2313784 A | 12/1997 |
| GB | 2373444 A | 9/2002 |
| JP | 59218154 A | 12/1984 |
| JP | 60135110 U | 9/1985 |
| JP | 09262261 A | 10/1997 |
| JP | 2002065782 | 3/2002 |
| JP | 2003310312 A | 11/2003 |
| JP | 2004081709 | 3/2004 |
| JP | 2005066247 | 3/2005 |
| JP | 2009000277 A | 1/2009 |
| WO | 96/20685 A1 | 7/1996 |
| WO | 2004012644 A1 | 2/2004 |
| WO | 2004021950 A1 | 3/2004 |
| WO | 2005082315 A1 | 9/2005 |
| WO | 2006039242 A2 | 4/2006 |
| WO | 2006083865 A2 | 8/2006 |

OTHER PUBLICATIONS

Office action issued Mar. 6, 2013 regarding U.S. Appl. No. 13/292,308—12 pgs.
Response filed Jun. 6, 2013 to Office Action dated Mar. 6, 2013 regarding U.S. Appl. No. 13/292,308—11 pgs.
Office action issued Sep. 12, 2013 regarding U.S. Appl. No. 13/292,308—12 pgs.
Response filed Nov. 12, 2013 to Office Action dated Sep. 12, 2013 regarding U.S. Appl. No. 13/292,308—10 pgs.
Supplemental Response filed Dec. 12, 2013 to Office Action dated Sep. 12, 2013 regarding U.S. Appl. No. 13/292,308—11 pgs.
Office action issued Jan. 23, 2013 regarding U.S. Appl. No. 13/362,130—10 pgs.
Response filed Apr. 22, 2013 to Office Action dated Jan. 23, 2013 regarding U.S. Appl. No. 13/362,130—17 pgs.
Office action issued May 24, 2013 regarding U.S. Appl. No. 13/362,130—12 pgs.
Response filed Jul. 24, 2013 to Office Action dated May 24, 2013 regarding U.S. Appl. No. 13/362,130—13 pgs.
Pre-Appeal Brief Request for Review dated Aug. 22, 2013 regarding U.S. Appl. No. 13/362,130—5 pgs.
Office action dated Mar. 26, 2015 in related European Patent Application No. 10156035.7, 4 pages.
Response dated Feb. 24, 2015 to Office Action dated Dec. 24, 2014 in related U.S. Appl. No. 13/214,632, 12 pages.
Response dated Mar. 10, 2015 to Office Action dated Dec. 24, 2014 in related U.S. Appl. No. 13/214,632, 3 pages.
Office Action dated May 20, 2014 in related Japanese Patent Application serial No. 2013-021713, 9 pages.
Office Action dated Jun. 18, 2014 in related U.S. Appl. No. 13/214,632, 18 pages.
Search Report dated Jul. 14, 2014 in related European Patent Application serial No. 13155960.1, 7 pages.
Office Action dated Aug. 1, 2014 in related European Patent Application serial No. 08153409.1, 4 pages.
Office Action dated Aug. 22, 2013 in related European Patent Application serial No. 08154262.3, 5 pages.
Office Action dated Jul. 18, 2014 in related Chinese Patent Application serial No. 201110410558.3, 14 pages
Office Action dated Nov. 25, 2013 in related Chinese Patent Application serial No. 201110410558.3, 24 pages.
Office Action dated Jul. 21, 2014 in related European Patent Application serial No. 08153402.6, 4 pages.
Mittelman, Jonathan S., MD: "Effectiveness of Leg Compression in Preventing Venous Stasis", The American Journal of Surgery, Dec. 1982, p. 611-613, vol. 144, No. 6, Elsevier Publ., Bridgewater, NJ, USA.
Tyco Healthcare Kendall, SCD Response Catalog, Mar. 2000, pp. 1-2.
Tyco Healthcare Kendall, SCD Soft Sleeve Catalog, Apr. 2001, pp. 1-2.
The Kendall Company, Vascular Therapy Products Catalog, Jan. 1996, pp. 8-5 thru 8-7.
The Kendall Company, The New SCD Compression Sleeve, Aug. 1993, pp. 1-2.
Tyco Healthcare Kendall, Prevention Gets Personal Mar. 2001, pp. 1, 2, 4.
Kendall SCD, Sequential Compression Sleeves, Patent Information, Jan. 1993, 6 pgs.
Ramsley and Bushnell, "Development of the US Woodland Battle Dress Uniform", Jan. 1981, p. 8 paragraph 4.
Office action issued Mar. 11, 2011 in related U.S. Appl. No. 11/733,082, now issued as U.S. Pat. No. 8,034,007—7 pgs.
Office action issued Mar. 10, 2010 regarding U.S. Appl. No. 11/733,095, now issued as U.S. Pat. No. 8,016,779—15 pgs.
Response filed Aug. 9, 2010 to Office Action dated Mar. 10, 2010 regarding U.S. Appl. No. 11/733,095, now issued as U.S. Pat. No. 8,016,779—19 pgs.
Office action issued Sep. 7, 2010 regarding U.S. Appl. No. 11/733,095, now issued as U.S. Pat. No. 8,016,779—17 pgs.
Response filed Mar. 1, 2011 to Office Action dated Mar. 10, 2010 regarding U.S. Appl. No. 11/733,095, now issued as U.S. Pat. No. 8,016,779—17 pgs.
Office action issued Mar. 10, 2010 regarding U.S. Appl. No. 11/733,074, now issued as U.S. Pat. No. 8,029,450—13 pgs.
Response filed Aug. 9, 2010 to Office Action dated Mar. 10, 2010 regarding U.S. Appl. No. 11/733,074, now issued as U.S. Pat. No. 8,029,450—16 pgs.
Office action issued Sep. 7, 2010 regarding U.S. Appl. No. 11/733,074, now issued as U.S. Pat. No. 8,029,450—15 pgs.

(56) References Cited

OTHER PUBLICATIONS

Response filed Dec. 23, 2010 to Office Action dated Sep. 7, 2010 regarding U.S. Appl. No. 11/733,074, now issued as U.S. Pat. No. 8,029,450—5 pgs.
Supplemental response filed Feb. 7, 2011 to Office Action dated Sep. 7, 2010 regarding U.S. Appl. No. 11/733,074, now issued as U.S. Pat. No. 8,029,450—6 pgs.
Office action issued Feb. 11, 2011 regarding U.S. Appl. No. 11/733,074, now issued as U.S. Pat. No. 8,029,450—10 pgs.
Response filed May 11, 2011 to Office Action dated Feb. 11, 2011 regarding U.S. Appl. No. 11/733,074, now issued as U.S. Pat. No. 8,029,450—8 pgs.
Office action issued Mar. 10, 2010 regarding U.S. Appl. No. 11/733,084—10 pgs.
Response filed Aug. 10, 2010 to Office Action dated Mar. 10, 2010 regarding U.S. Appl. No. 11/733,084—11 pgs.
Response dated Sep. 18, 2014 to Office Action dated Jun. 18, 2014 in related U.S. Appl. No. 13/214,632, 11 pages.
Office Action dated Dec. 24, 2014 in related U.S. Appl. No. 13/214,632, 20 pages.
Response dated Jan. 6, 1015 to Office Action dated Oct. 6, 2014 in related U.S. Appl. No. 14/093,756, 3 pages.
Office action issued Sep. 7, 2010 regarding U.S. Appl. No. 11/733,084—9 pgs.
Response filed Feb. 7, 2011 to Office Action dated Sep. 7, 2010 regarding U.S. Appl. No. 11/733,084—9 pgs.
Office action issued Mar. 7, 2011 regarding U.S. Appl. No. 11/733,084—8 pgs.
Response filed Jun. 7, 2011 to Office Action dated Mar. 7, 2011 regarding U.S. Appl. No. 11/733,084—9 pgs.
Office action issued Jul. 6, 2011 regarding U.S. Appl. No. 11/733,084—10 pgs.
Response filed Oct. 7, 2011 to Office Action dated Jul. 6, 2011 regarding U.S. Appl. No. 11/733,084—6 pgs.
Office action issued Mar. 11, 2010 regarding U.S. Appl. No. 11/733,088, now issued as U.S. Pat. No. 8,016,778—14 pgs.
Response filed Sep. 13, 2010 to Office Action dated Mar. 11, 2010 regarding U.S. Appl. No. 11/733,088, now issued as U.S. Pat. No. 8,016,778—8 pgs.
Office action issued Sep. 28, 2010 regarding U.S. Appl. No. 11/733,088, now issued as U.S. Pat. No. 8,016,778—13 pgs.
Response filed Jan. 28, 2011 to Office Action dated Sep. 28, 2010 regarding U.S. Appl. No. 11/733,088, now issued as U.S. Pat. No. 8,016,778—11 pgs.
Office action issued Mar. 10, 2010 regarding U.S. Appl. No. 11/733,077—10 pgs.
Response filed Aug. 9, 2010 to Office Action dated Mar. 10, 2010 regarding U.S. Appl. No. 11/733,077—13 pgs.
Office action issued Sep. 7, 2010 regarding U.S. Appl. No. 11/733,077—13 pgs.
Response filed Nov. 8, 2010 to Office Action dated Sep. 7, 2010 regarding U.S. Appl. No. 11/733,077—7 pgs.
Advisory Action issued Nov. 23, 2010 in U.S. Appl. No. 11/733,077—3 pgs.
Supplemental response filed Mar. 1, 2011 to Office Action dated Sep. 7, 2010 regarding U.S. Appl. No. 11/733,077—8 pgs.
Office action issued Apr. 28, 2011 regarding U.S. Appl. No. 11/733,077—11 pgs.
Response filed Jul. 25, 2011 to Office Action dated Apr. 28, 2011 regarding U.S. Appl. No. 11/733,077—7 pgs.
Office action issued Aug. 19, 2011 regarding U.S. Appl. No. 11/733,077—14 pgs.
Response filed Dec. 19, 2011 to Office Action dated Aug. 19, 2011 regarding U.S. Appl. No. 11/733,077—9 pgs.
Office action issued Dec. 15, 2008 regarding U.S. Appl. No. 11/733,087—9 pgs.
Response filed May 7, 2009 to Office Action dated Dec. 15, 2008 regarding U.S. Appl. No. 11/733,087—10 pgs.
Office action issued Aug. 20, 2009 regarding U.S. Appl. No. 11/733,087—12 pgs.
Response filed Nov. 16, 2009 to Office Action dated Aug. 20, 2009 regarding U.S. Appl. No. 11/733,087—12 pgs.
Office action issued Jan. 29, 2010 regarding U.S. Appl. No. 11/733,087—11 pgs.
Response filed Jun. 16, 2010 to Office Action dated Jan. 29, 2010 regarding U.S. Appl. No. 11/733,087—10 pgs.
Office action issued Sep. 14, 2010 regarding U.S. Appl. No. 11/733,087—12 pgs.
Response filed Feb. 14, 2011 to Office Action dated Sep. 14, 2010 regarding U.S. Appl. No. 11/733,087—11 pgs.
Supplemental response filed Apr. 29, 2011 to Office Action dated Sep. 14, 2010 regarding U.S. Appl. No. 11/733,087—6 pgs.
Response filed May 13, 2011 to Office Action dated Mar. 11, 2011 regarding U.S. Appl. No. 11/733,082—6 pgs.
Australian Office action issued Oct. 26, 2011 regarding Australian Patent Application No. 2008201506, 2 pgs.
Response filed Apr. 18, 2012 to Australian Office action issued Oct. 26, 2011 regarding Australian Patent Application No. 2008201506, 8 pgs.
Chinese Office action issued Aug. 17, 2010 regarding Chinese Patent Application No. 200810090992.6, 6 pgs.
Chinese Office action issued Apr. 8, 2011 regarding Chinese Patent Application No. 200810090992.6, 3 pgs.
Chinese Office action issued Aug. 27, 2013 regarding Chinese Patent Application No. 201110269952.X, 7 pgs.
European Search Report for EP 10156035.7 issued May 6, 2010, 8 pgs.
European Office action issued Oct. 11, 2012 regarding European Patent Application No. EP 10156035.7, 3 pgs.
European Office action issued Oct. 11, 2012 regarding European Patent Application No. EP 10165217.0, 4 pgs.
Response filed Dec. 20, 2012 to European Office action issued Oct. 11, 2012 regarding European Patent Application No. EP 10165217.0, 7 pgs.
European Search Report for EP 10165217.0 issued Feb. 14, 2013, 8 pgs.
European Office action issued Mar. 25, 2013 regarding European Patent Application No. EP 10165217.0, 2 pgs.
Response filed Aug. 26, 2013 to European Office action issued Mar. 25, 2013 regarding European Patent Application No. EP 10165217.0, 4 pgs.
Office action issued Dec. 17, 2012 regarding U.S. Appl. No. 13/214,739—10 pgs.
Response filed Mar. 18, 2012 to Office Action dated Dec. 17, 2012 regarding U.S. Appl. No. 13/214,739—9 pgs.
Office action issued Oct. 26, 2012 regarding U.S. Appl. No. 13/234,835—8 pgs.
Response filed Jan. 25, 2013 to Office Action dated Oct. 26, 2012 regarding U.S. Appl. No. 13/234,835—13 pgs.
Office action issued May 30, 2013 regarding U.S. Appl. No. 13/234,835—6 pgs.
Response filed Jul. 26, 2013 to Office Action dated May 30, 2013 regarding U.S. Appl. No. 13/234,835—3 pgs.,

COMPRESSION DEVICE HAVING WELD SEAM MOISTURE TRANSFER

CROSS-REFERENCE TO RELATED APPLICATION

This application is a continuation of U.S. Ser. No. 11/733,077, filed Apr. 9, 2007, the entirety of which is incorporated herein by reference.

TECHNICAL FIELD

The present invention is directed generally to a compression device for applying compression therapy to a body part of a wearer, more particularly a compression sleeve.

BACKGROUND

A major concern for immobile patients and like persons are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popiteal and tibial return deoxygenated blood to the heart. For example, when blood circulation in these veins is retarded due to illness, injury or inactivity, there is a tendency for blood to accumulate or pool. A static pool of blood may lead to the formation of a blood clot. A major risk associated with this condition is interference with cardiovascular circulation. Most seriously, a fragment of the blood clot can break loose and migrate. A pulmonary emboli can form from the fragment potentially blocking a main pulmonary artery, which may be life threatening. The current invention can also be applied to the treatment of lymphedema.

The conditions and resulting risks associated with patient immobility may be controlled or alleviated by applying intermittent pressure to a patient's limb, such as, for example, a leg to assist in blood circulation. For example, sequential compression devices have been used, such as the device disclosed in U.S. Pat. No. 4,091,864 to Hasty. Sequential compression devices are typically constructed of two sheets of material secured together at the seams to define one or more fluid impervious bladders, which are connected to a source of pressure for applying sequential pressure around a patient's body parts for improving blood return to the heart. The inflatable sections are covered with a laminate to improve durability and protect against puncture. As part of the compression device, the two sheets are structurally designed to withstand a changing pressure over time under repeated use.

The impermeability of the sleeve makes it uncomfortable for the patient because moisture (i.e. perspiration) is trapped between the impermeable sheet and the patient's body part. This leads to the patient's unwillingness to wear the sleeve, thereby, endangering the health of the patient. Moreover, the sleeve is generally non-stretchable and bulky because the bladders must be able to retain a significant amount of fluid pressure during treatment. Thus, the prior art sleeves restrict the mobility of the patient. Also chafing of a patient's limb can occur because the prior art designs retain the inflatable bladders in a fixed position when under pressure. As the pressure changes during treatment, the bladders press and release against the patient's limb, rubbing and chafing the skin. A bladder may wrinkle or fold which can cause further irritation during a compression cycle. The final construction of a prior art sleeve is bulky, rigid and may feel heavy to a person over an extended period of use. The present invention is directed to solving the above mentioned deficiencies without compromising durability and clinical effectiveness.

As stated above, prior art devices are constructed for durability and strength. As shown in U.S. Patent Publication No. 2005/0187503 A1 to Tordella, Tordella describes a sleeve with a top and bottom sheet. The sheets are fixed at the perimeter to form an inflatable section or bladder, as shown in FIG. 2. The material forming the chambers or bladders is polyvinyl chloride or polyethylene. These materials are impervious to moisture as they need to be fluid tight and thick enough to withstand thousands of compression cycles without bursting. Tordella provides some cooling when the device provides for vent holes placed about the sleeve. Also, a slit is introduced through the sheets, but Tordella's slit is not within the area defined by the chambers (i.e. bladders). Generally, access to skin will provide evaporation of bodily fluids collected at the openings, but the Tordella invention does not provide for removing fluid trapped beneath the impervious sheet away from the openings. The evaporation is limited to the openings and the immediate area under the impervious sheet near the opening. At least some of the embodiments of the present invention provide a solution to the problem of trapped fluid by moving the fluid from underneath the impervious sheet, at a sufficient rate, to a plurality of openings positioned, sized and shaped to maintain blood flow and evaporate the moisture as described below. The Tordella sleeve construction is similar to the Model 9529 SCD Express device (knee length sleeve) available in the United States from Tyco Healthcare Group L.P., which is discussed in more detail below.

There are other prior art attempts to improve comfort through breathability and evaporation. U.S. Pat. No. 3,824,492 to Nicholas is directed to a garment that provides pulsating pressure to a lower extremity. A number of holes are placed at the toe area. Air entering the holes is pulled across the patient's skin through an air space provided by the device when worn. Nicholas has a hard outer shell. The Nicholas device suffers from a number of drawbacks not found in the present invention. The compression sleeves of at least some embodiments of the present invention are elastic, at the inner layer and outer layer, to improve patient mobility and flexure. Instead of a hard outer shell like Nicholas, the present invention has in some embodiments a breathable, soft and elastic outer covering. The elastic outer cover of the present invention helps the sleeve conform to the limb under pressure. The present invention does not have the structure for a channel at the skin to move air across the skin and into the ambient environment.

Hasty (U.S. Pat. No. 4,091,804) and Annis (U.S. Pat. No. 4,207,876) disclose a plurality of openings in communication with a ventilation channel. Air is forced through the channel and openings onto the skin by a compressor. The present invention does not use a ventilation channel within the layers of the sleeve. Furthermore in preferred embodiments of the present invention, the compression sleeve does not use its compressor to force the air through the openings onto the skin though the channel. In embodiments of the present invention, air at the openings interfaces with the wicking material to evaporate wicked moisture as described more fully below. The transport mechanism can be the wicking material in present invention. Other devices such as Jacobs (U.S. Pat. No. 5,489,259), provide for direct access to a portion of the patient's limb, but the Jacobs' device suffers in that cooling (evaporation) is limited to the localized openings. The Neal reference (U.S. Pat. No. 5,693,453), describes openings of various geometries, but the size, shape and distribution is a matter of convenience of use. The Neal device is not directed to prophylaxis treatment.

Breathability is associated with cooling through evaporation, as air must be allowed to pass over the openings to the skin. Faster evaporation can occur if a device can breathe through its outer layer which is a problem not solved in the cited references. A number of cited references mention breathing to avoid sweat build-up, but none of the references are directed to providing prophylaxis treatment using sequential compression. A device to Hall (U.S. Pat. No. 6,520,926), describes a support socking that is breathable, but Hall provides no additional detail on how it is made breathable. A device to Roth (U.S. Pat. No. 7,044,924), describes that various sized holes may be punched through both the inner and outer sheet 202/204, between adjacent seams 234 or 242 to allow for ventilation. Further, a moisture-wicking lining material may be applied to the surface of the inner sheet 204 for comfort. The lateral seams 230, 232 and 234 and the longitudinal seams 238 and 240 form a plurality of inflatable bladders 250. The Applicants adapt their inner sheet to provide wicking properties because the Applicants discovered laminating or applying the wicking material to a sheet may compromise the wicking ability of material. The fibers of the wicking material would be interrupted, made discontinuous by the lamination; therefore, interfering with the capillary action of the wicking fibers as described below.

Roth may introduce a low pressure area adjacent to bladders which has been shown to promote blood pooling. The Applicants particularly structured at least some embodiment of their device to avoid blood pooling by configuring adjacent bladders to minimize low pressure areas between the adjacent bladders. Applicant's device was demonstrated to maintain clinical efficacy as described below. Roth does not provide any information regarding the clinical efficacy of its device and does not provide any figures showing its openings or its wicking material. A sock device to Linnane (U.S. Patent Publication No. 2006/0010574), describes a compression stocking with a wicking material near the person's skin for wicking moisture along channels to the outside of the stocking. The present invention directs moisture to a plurality of openings sized, shaped, and located along the compression device for maximizing evaporation while maintaining clinical efficacy.

Elasticity is found in the prior art and is commonly understood to be an important benefit for compression stockings such as the T.E.D®, sold by the assignee of the present invention. A drawback of the prior art sequential compression devices, like that shown in Hasty, is that the bladder material is flexible but not elastic. The prior art bladders are formed as part of a laminated construction adding further rigidity and durability. The Tordella reference discloses a sleeve with flexible, elastic sections between the inflatable sections or portions to facilitate mobility of a patient. Tordella does not disclose an elastic design circumferentially and longitudinally along the sleeves entire length, which is solved by the present invention.

The present invention helps overcome patient discomfort without decreasing clinical effectiveness, as shown in supporting lab tests disclosed in this application. An important objective is to improve patient compliance, defined as using the sleeve as prescribed by a doctor. There is a direct correlation of patient compliance with patient comfort. Compliance with mechanical compression devices has always been a concern in healthcare. A clinical staff is overworked with patient loads and duties and thus one-on-one patient care time is at a premium. Often it has been reported that patients will become uncomfortable wearing compression sleeves and request that the sleeves be taken off, even though they may be necessary to prevent a fatal occurrence of a pulmonary embolism. Clinical staff may not have time to fully educate the patient on the importance of wearing the sleeve, and may not have the time to ensure that the patient is constantly wearing the sleeve. For example, a research study performed by the CMAJ Clinical Practice Guidelines for the Care and Treatment of Breast Cancer, discussed treating lymphedema associated with breast cancer. The study indicates patients are not compliant because the devices are generally difficult to use and not comfortable. It is this reason that compression sleeve manufacturers are trying to introduce more comfortable sleeves while maintaining the clinical efficacy already found in the prior art devices. With the need for shorter stays at the hospital and more outpatient surgery, the need for more a comfortable device that is easier to use, while maintaining clinical efficacy, is a long-felt need in the industry.

As stated above there is a long felt need, not found in prior art sleeves for improving comfort without compromising clinical effectiveness. Other prior art devices on the market, such as Aircast®, Huntleigh®, and Hill-Rom® suffer from a number of drawbacks, disclosed below, and solved in the present invention. Preferred embodiments of the present invention provide substantial cooling without compromising the clinical efficacy of the prior art devices such as Kendall's Model 9529 and 9530 compression sleeves in providing prophylaxis DVT. The present invention is directed to improving patient comfort and thus compliance in terms of physician prescribed use. The following list of features is included in the construction of at least some embodiments of the present invention: soft, cool, easy to use and apply, non-irritating, flexible, fit a patients changing needs, and improved patient compliance.

The present invention in its preferred embodiments is engineered to provide the maximum amount of evaporation, which is a function of wicking properties and opening size, location and shape, while minimizing any negative impact on blood flow augmentation or clinical efficacy. Blood flow is dependent on opening size, shape and location, that is, the opening properties must be minimized not to interfere with blood flow, while maximizing the evaporation of trapped moisture beneath the impervious layer.

As is known in the art, a compression sleeve is used to provide prophylaxis treatment to a wearer's body part. This treatment is to help prevent the formation of blood clots by increasing the velocity of blood, in a cascading manner along a limb toward the heart. The illustrated and described embodiments of the present invention wrap around the full circumference around a patient's limb. The embodiments of the present invention are not limited to full wrap devices. The structural changes that accomplish the features described below will enhance the comfort and use of the prior art devices, but not necessarily at the expense of their claimed clinical efficacy.

SUMMARY

In a first aspect, a device for applying compression treatment to a part of a wearer's body generally comprises a wicking layer contacting skin on the wearer's body part when the device is mounted on the body part. A bladder selectively applies compression to the body part. The bladder comprises two sheets of air impermeable thermoplastic bladder material secured together and to the wicking layer along a weld having a thickness extending from the wicking layer through the thickness of the sheets of bladder material. The wicking layer has uniformly distributed polymeric wicking fibers that extend through the thickness of the weld to allow fluid wicked from a wearer's skin to evaporate to the atmosphere.

In said first aspect, where the wicking layer is a knitted sheet.

In said first aspect, where the separate sheets of bladder material are secured to the wicking layer along a plurality of welds. One weld extends along a periphery of each sheet of bladder material.

In said first aspect, where the wicking layer extends beyond the periphery of the sheets of bladder material.

In said first aspect, where the weld is a spot weld.

In said first aspect, where the thermoplastic bladder material has a polar molecule and the polymer of the polymeric wicking fibers has a non-polar molecule.

In said first aspect, where the thermoplastic bladder material is PVC and the polymeric wicking fibers are polyester.

In said first aspect, where the bladder extends around at least 90 percent of a median circumference of the wearer's body part.

In said first aspect, further comprising an outer layer disposed on a side of the bladder away from the wearer's body part when the device is mounted on the body part. The outer layer is secured to the thermoplastic bladder material and the wicking layer at the weld.

In said first aspect, where the bladder defines a plurality of openings. The wicking layer and the outer layer are secured to each other at the openings.

In said first aspect, where the outer layer comprises woven fibers.

In said first aspect, where the outer layer is a polyester mesh material treated with a hydrophilic material.

In said first aspect, where at least one of the wicking layer and the outer layer is resilient.

In a second aspect, a device for applying compression treatment to a part of a wearer's body generally comprises a wicking layer contacting skin on the wearer's body part when the device is mounted on the body part. A bladder selectively applies compression to the body part. The bladder comprises two sheets of polyvinyl chloride bladder material secured together and to the wicking layer along a weld having a thickness extending from the wicking layer through the thickness of the sheets of bladder material. The wicking layer is a knitted sheet having polyester wicking fibers that extend through the thickness of the weld to allow fluid wicked from a wearer's skin to evaporate to the atmosphere.

In said second aspect, where the separate sheets of bladder material are secured to the wicking layer along a plurality of welds. One weld extends along a periphery of each sheet of bladder material.

In said second aspect, where the wicking layer extends beyond the periphery of the sheets of bladder material.

In said second aspect, where the weld is a spot weld.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
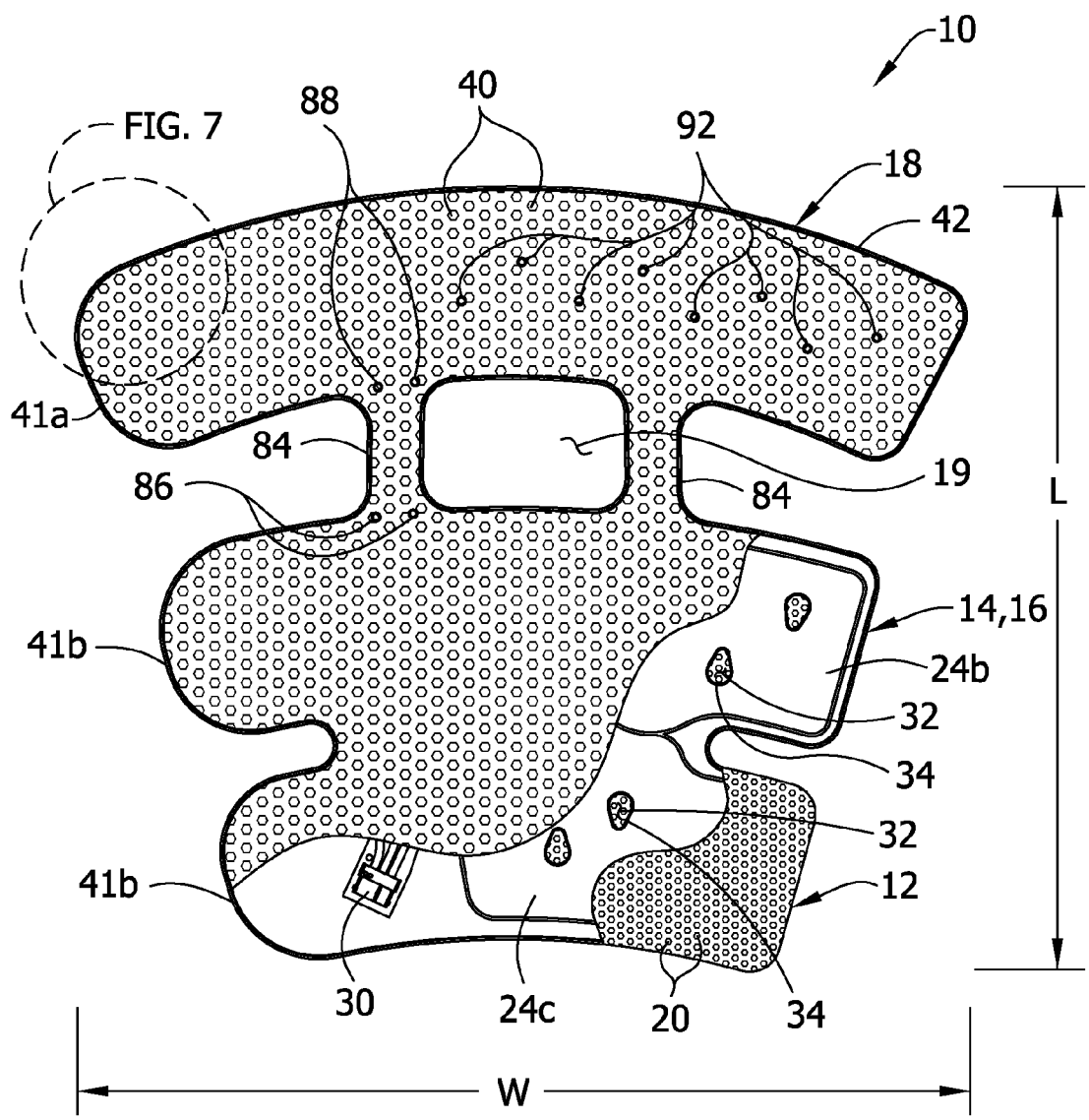
FIG. 1 is a front elevation of one embodiment of a compression sleeve with an outer cover and intermediate layers of the sleeve partially removed to show underlying layers.
Figure 2:
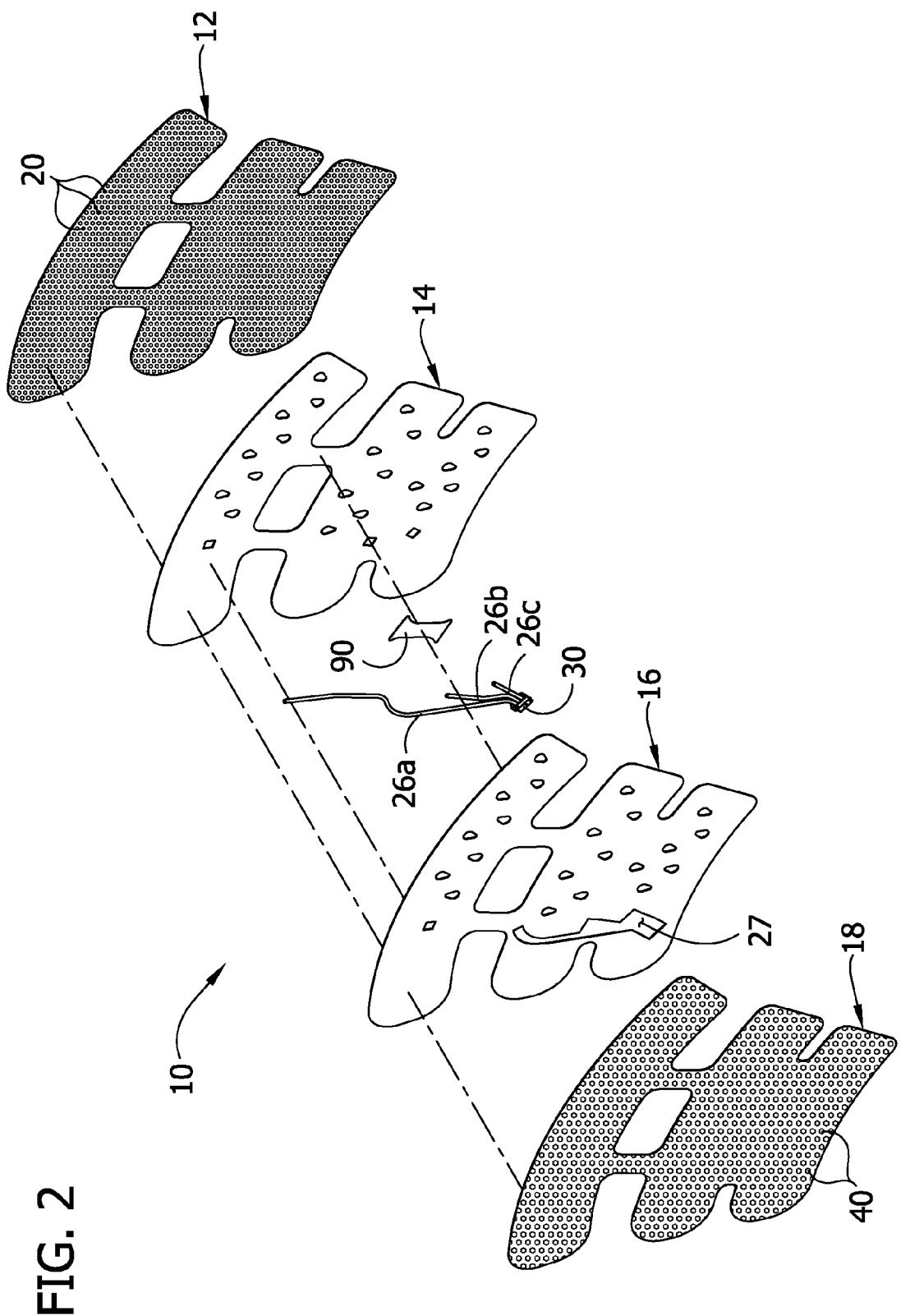
FIG. 2 is an exploded perspective of the compression sleeve.

Referring now to the drawings, and in particular to FIGS. 1 and 2, one embodiment of a compression device (broadly, "a garment or a sleeve") is generally indicated at 10 for applying sequential compression therapy to a limb of a wearer. The compression sleeve is of the type sized and shaped for being disposed around a leg of the wearer, but could be configured for application to other parts of the wearer's body. More specifically, the sleeve 10 has a width W (FIG. 1) for being wrapped around a full circumference of the leg and a length L (FIG. 1) for running from the ankle to a thigh of the leg. This type of sleeve is generally referred to in the art as a thigh-length sleeve. It will be understood that a compression sleeve may come in different sizes, such as a knee length sleeve (FIG. 20) that extends from the ankle up the calf of the leg. It is understood that other types of compression devices for being disposed about other limbs of the wearer's body, are within the scope of this invention, such as a wrap around a patient's chest in the treatment of breast cancer.

A numerical study performed by R. D. Kamm, titled "Bioengineering Studies of periodic External Compression as Prophylaxis Against Deep Vein Thrombosis—Part I: Numerical Studies" concluded, among other things, that "the entire length of the veins should be emptied as full and as rapidly as possible." The Kamm study reviews three types of compression, the one of interest is wavelike compression. Wavelike compression is most similar to sequential compression provided by the illustrated embodiments of the present invention. The Kamm Study found wavelike compression is most effective in moving blood for an effective prophylaxis treatment.

Referring to FIG. 1, the compression sleeve 10 comprises four layers secured together in the illustrated embodiment of the present invention. The scope of the present invention is not limited to four layers. More specifically, the compression sleeve comprises an inner layer, generally indicated at 12, on which a first intermediate layer (broadly, a first bladder layer), generally indicated at 14, is overlaid. A second intermediate layer (broadly, a second bladder layer), generally indicated at 16, overlies the first intermediate layer 14 and is secured thereto. An outer cover generally indicated at 18, overlies and is secured to the second intermediate layer 16. In use, the inner layer 12 is disposed most adjacent to the limb of the wearer and is in contact with the limb of the wearer, and the outer cover 18 is most distant from the limb of the wearer. A knee opening 19 is formed through the sleeve 10 that is generally aligned with the back of the knee when the sleeve is applied to the leg. The layers have the same geometric shape and are superposed on each other so that edges of the layers generally coincide. It is contemplated that one or more of the layers 12, 14, 16, or 18 may not be superposed on a corresponding layer, but slightly offset to accommodate a particular feature of a patient's limb. Moreover, the number of sheets or thickness making up each layer 12, 14, 16, or 18 of the compression sleeve 10 may be other than described. The thickness of the layers may vary to add strength or to cause more expansion in one direction, such toward the limb, during inflation.

Figure 4:
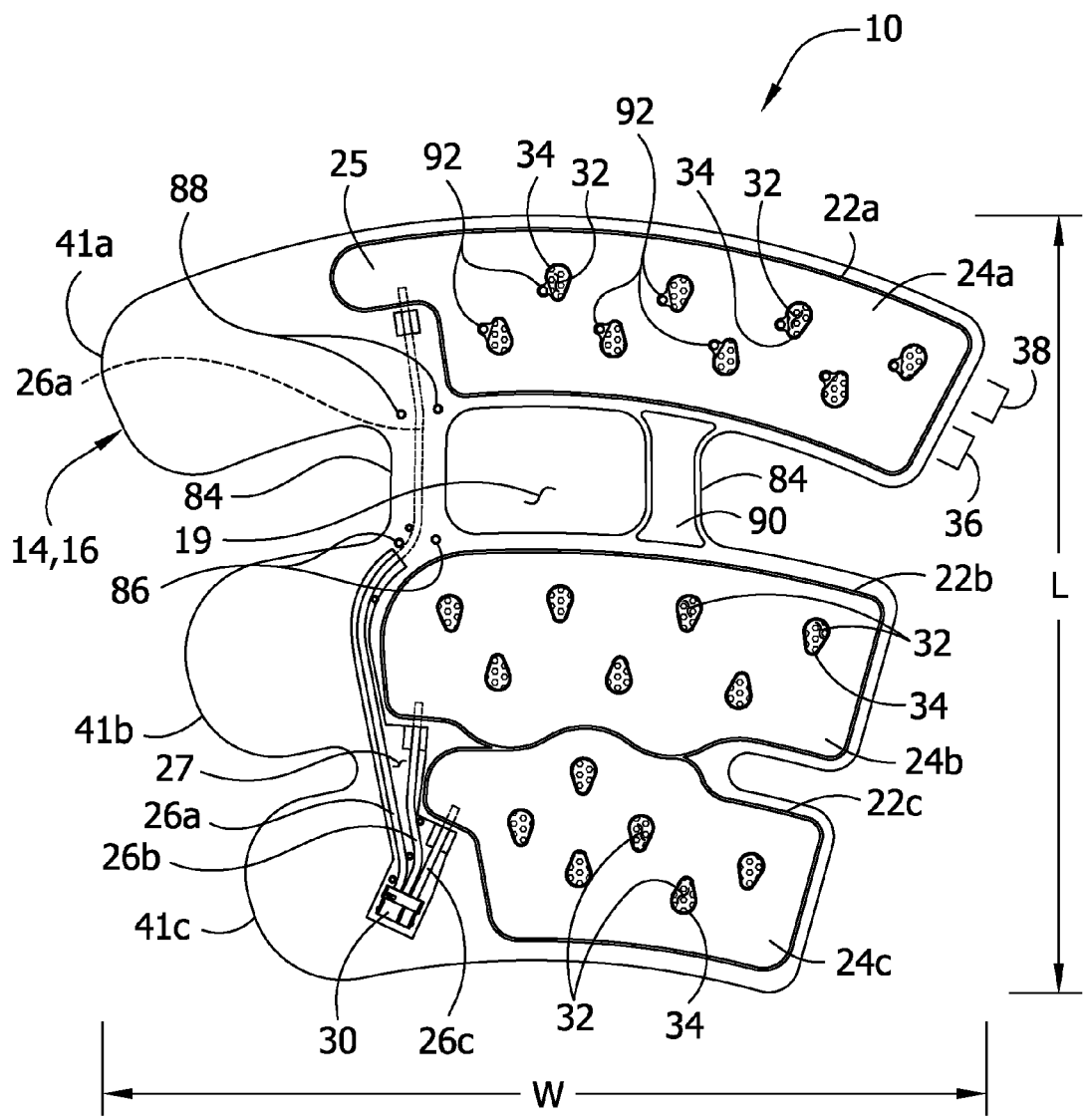
FIG. 4 is a front elevation of the compression sleeve with the outer cover removed.

Referring to FIGS. 1, 2 and 4, the first and second intermediate layers 14, 16, respectively, each include a single sheet of elastic material (broadly, "bladder material"). For example, the sheets 14 and 16 are made of a pliable PVC material as the bladder material. Layers 12 and 18 are made of a polyester material. The second intermediate layer 16 is secured to the first intermediate layer 14 via three separate bladder seam lines 22a, 22b, 22c defining a proximal bladder 24a, an intermediate bladder 24b and a distal bladder 24c, respectively, that are spaced apart longitudinally along the sleeve 10. The number of bladders may be other than three without departing from the scope of the present invention. As used herein, the terms "proximal", "distal", and "intermediate" represent relative locations of components, parts and the like of the compression sleeve when the sleeve is secured to the wearer's limb. As such, a "proximal" component or the like is disposed most adjacent to a point of attachment of the wearer's limb to the wearer's torso, a "distal" component is disposed most distant from the point of attachment, and an "intermediate" component is disposed generally anywhere between the proximal and distal components.

For reasons discussed below, the proximal bladder 24a defines a proximal, lateral extension 25 near the upper edge margin of the sleeve 10. The bladders 24a, 24b, 24c are circumferential bladders meaning that they are sized and shaped to be wrapped around substantially the entire circumference of the wearer's limb or very nearly the entire circumference of the limb. For example, in one embodiment the bladders 24a, 24b, 24c each extend around at least 90% of a median circumference of a leg. However, prior art devices have partial bladders such as AirCast® @ and HillRom®, and these prior art devices do not provide for openings, elasticity and other features of the present invention. It is to be understood that the construction described herein can be adopted by the prior art sleeves with a partial bladder construction, without departing from the scope of the present invention.

The intermediate layers 14, 16 may be secured together by radiofrequency welding, adhesive, or other chemical and/or mechanical process. It is understood that the intermediate layers 14, 16 may be secured together at other locations, such as around their peripheries and at bladder seam lines 22a, 22b, 22c to further define the shape of the inflatable bladders 24a, 24b, 24c. For purposes discussed below, the first intermediate layer 14 is secured to the inner layer 12 along a seam line 25 (FIGS. 5 and 6) that runs along the outer periphery of the first intermediate layer 14 so that central regions of the bladders 24a, 24b, 24c are not secured to the inner layer 12. This permits the bladders 24a, 24b, 24c to move relative to the inner layer 12. The second intermediate layer 16 may also be secured to the inner layer 12 along the same seam line 25. The first intermediate layer 14 may be secured to the inner layer 12 by RF welding or adhesive or in other suitable ways. This structure improves comfort as described below.

Referring to FIGS. 2 and 4, each inflatable bladder 24a, 24b, 24c receives fluid from a source of compressed fluid (not shown) via a dedicated proximal bladder tube 26a, intermediate bladder tube 26b, and distal bladder tube 26c, respectively, (FIG. 2). A tube line need not be dedicated to a bladder to practice the invention. Each tube 26a, 26b, 26c is disposed between the intermediate layers 14, 16 and secured to the respective bladder 24a, 24b, 24c by the respective bladder seam line 22a, 22b, 22c. As shown best in FIGS. 2 and 4, the first intermediate layer 16 defines a cutout 27 (FIG. 2) so that portions of the tubes 26a, 26b, 26c are not disposed between the intermediate layers. Other ways of securing the tubes 26a, 26b, and 26c to the bladders 24a, 24b, and 24c are within the scope of the invention. The opposite ends of the tubes 26a, 26b, 26c are grouped together using a second connector 30 (FIGS. 1 and 2) that is adapted to fluidly connect the tubes to the source of compressed fluid. The source of compressed fluid may be an air compressor under the control of a microprocessor that sequentially pressurizes the bladders as is generally known in the art. An exemplary air compressor is described in U.S. Pat. No. 5,876,359 to Bock, the disclosure of which is incorporated herein by reference. The bladders 24a, 24b, 24c may be configured to contain air pressurized to at least about 10 mm Hg (1333 Pa) to about 45 mm Hg (6000 Pa). The bladders should be capable of being repeatedly pressurized without failure. Materials suitable for the sheets include, but are not limited to, flexible PVC material that will not stretch substantially. In another embodiment, the intermediate layers may form a chamber for receiving an inflatable bladder that is formed separate from the chamber. In this embodiment, the layers may not be capable of containing pressurized air as along as the inflatable bladders are so capable. It will be noted that the bladders 24a, 24b, 24c can have openings 32 extending completely through the bladders, as described in the embodiments of the present invention.

Referring particularly to FIGS. 1 and 4, the sleeve 10 defines a connecting section including a pair of bridge members 84 on opposite sides of the knee opening 19 that extend between and connect a proximal portion of the sleeve that includes the proximal bladder 24a to the remainder of the sleeve. The proximal tube 26a generally lies along an axis of bridge member 84 to provide structural, lengthwise support to the sleeve 10. As shown best in FIG. 4, the cutout 27 in the intermediate sheet 16 does not extend through the bridge member 84. The proximal tube 26a extends between spaced apart distal spot welds 86 disposed adjacent to a distal end of the bridge member 84 and between spaced apart proximal spot welds 88 disposed adjacent to a proximal end of the bridge member. The spot welds secure the tube 26a to the bridge member 84 such that the proximal bladder tube 26a constitutes a rigid structural component (broadly, a "first rigid structural component") for maintaining the spacing between the proximal bladder 24a and the intermediate bladder 24b and in maintaining the longitudinally structural integrity of the connecting section. In other words, the sleeve 10 is rigidified against collapsing or sliding down the wearer's leg. As explained above, the proximal bladder tube 26a is secured to the proximal bladder 24a at the proximal, lateral extension 25. The proximal bladder tube 26a runs along a side of a distal portion of the proximal bladder 24a so that it does not enter the bladder until it reaches the proximal, lateral extension 25. Being secured at the proximal, lateral extension 25 of the bladder 24a provides additional longitudinal support to the sleeve 10 because the proximal bladder tube 26a extends lengthwise across more of the proximal portion of the sleeve than if the tube was secured at a distal portion of the bladder. In one embodiment, the proximal bladder tube 26a extends at least a quarter of the way across a thigh section of the sleeve 10. In another embodiment shown in FIG. 4, the tube 26a extends more than half way across the thigh section. This helps to keep the proximal portion of the sleeve 10 from collapsing and/or sliding out of position down the wearer's leg.

Referring to FIGS. 2 and 4, in addition to the proximal bladder tube 26a, a second rigid structural component 90, disposed between the intermediate layers 14, 16 and extending within the other bridge member 84 of the connecting section, also provides longitudinal structural support to the sleeve 10. The second structural component 90 extends between proximal and distal ends of the bridge member 84. The respective proximal and distal ends of the structural component 90 are wider than an intermediate portion of the component and the periphery of the component generally conforms to the peripheries of side walls of the bridge member 84 so that the structural component is secured to the bridge member.

Figure 3:
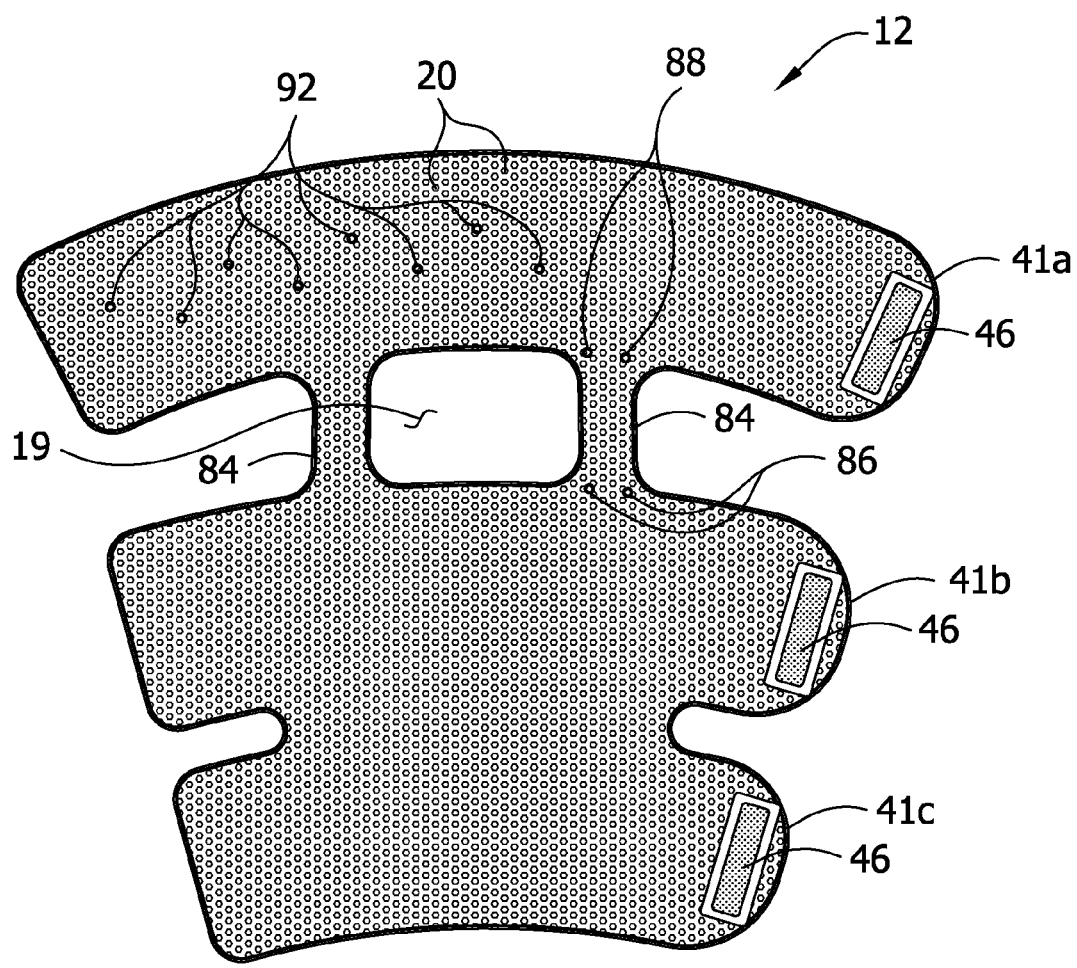
FIG. 3 is a rear elevation of an inner layer of the compression sleeve.

Referring to FIGS. 1, 3 and 4, the proximal bladder 24a is secured to the inner layer 12 and the outer cover 18 at spot welds 92 adjacent to the bladder openings 32 and within an outer perimeter of the bladder defined by the bladder seamline 22a. The spot welds 92 maintain the outer cover 18 and the inner layer 12 in proper position with respect to the bladders 24a, 24b, 24c. In other words, the spot welds 92 prevent the bladders 24a, 24b, 24c from substantially shifting relative to the inner layer 12 and the outer cover 18 while still providing the sleeve 10 with substantial flexibility. Too much movement of inner layer 12 and the outer cover 18 with respect to the bladders 24a, 24b, 24c may reduce the fit of the sleeve, thereby leading to reduced efficacy of the compression therapy. The proximal bladder 24a is free from securement to the inner layer 12 and outer cover 18 other than at the spot welds 92 to maintain flexibility of the sleeve so that mobility of the patient's leg is not compromised. Inner layer 12 may be joined to layer 16 at the spot welds 86, 88, 92 or the inner layer 12 may be joined at the seam line 34 of the opening 32. Away from the openings 32 and spot welds 86, 88, 92, the inner layer 12 is not joined to surface of the bladder material forming the bladder that expands to provide compression treatment to the patient's limb.

In one embodiment, the bladders 24a, 24b, 24c are constructed to expand more toward the wearer than away from the wearer, thereby applying a greater compressive force on the wearer's limb. In one example, the first intermediate layer 14 (i.e., the layer most adjacent to the inner layer 12) has a lesser thickness than that of the second intermediate layer 16. With both layers 14, 16 being of the same material (i.e., elastic PVC material) the first intermediate sheet will have a lower modulus of elasticity. Thus, when air is introduced into the bladders 24a, 24b, 24c, the bladders will expand more toward the inner layer 12 and the wearer than away from the wearer. It is understood that other ways, besides a difference in thickness between the intermediate layers 14, 16, of constructing the bladders 24a, 24b, 24c so that they expand more toward the wearer than away from the wearer is within the scope of the invention.

Referring to FIGS. 2 and 3, the inner layer 12 is constructed of a material that is capable of wicking moisture near a patient's limb. The inner (or "wicking") layer 12, through capillary action, absorbs moisture trapped near the leg or limb of the wearer, carries the moisture away from the surface of the limb, and transports the moisture from locations on the limb at the inner layer 12 where the moisture is abundant to areas where it is less abundant, at the openings 32, for evaporation to the ambient environment. The openings may be of various sizes, shapes and locations within the bladder area providing the compression. An opening 32 exposes the wicking layer to the ambient or surrounding air as opposed to the portion of the wicking layer beneath the bladder material. The portions of the inner layer 12 in registration with the openings 32 may be referred to as "exposed portions". Other ways of exposing the wicking material are within the scope of this invention, such as slits or extending the wicking material outside the perimeter of the bladder material. The present invention has its exposed portion within the bladder area that provides compression. The compression region is the bladder area expanding and contracting under the influence of air pressure or other fluids. The area of the bladder not providing compression is the seamline or weld points which are points of the bladder material sealed together to provide an air or water tight boundary or other regions of the opposed sheets 14, 16 outside the perimeter of the bladder. The wicking material 12 may be inter-weaved with the impervious material to form the inner layer 12. The wicking material 12 transports moisture to an area of less moisture. The openings 32 must be engineered to maintain blood velocity, while maximizing evaporation of moisture. Suitable wicking materials may be comprised of, for example, some form of, polyester, although they may be comprised of polypropylene. Microfibers may be used. Suitable microfiber materials include, but are not limited to, CoolDry model number CD9604, sold by Quanzhou Fulian Warp Knitting Industrial Co., Ltd., Quanzhou City, Fujian Province, China and CoolMax®, sold by E. I. du Pont de Nemours and Company, Wilmington, Del.

A number of lab tests were performed to determine the embodiments of the present invention. The tests looked at the evaporation rate, wicking performance and elasticity to provide improved comfort without compromising blood flow velocity. The study used Kendall's 9529 knee length sleeve model and three other competitor models denoted as knee length sleeves A, B and C. Third party testing has demonstrated the superior performance of a full length, circumferential wrap such as Kendall's 9530. The American Journal of Surgery study "Effectiveness of Leg Compression in Preventing Venous Stasis", concluded a sequential compression device, like Kendall's 9530 model, is best at moving blood.

The study concluded that DVT prophylaxis using the 9530 leg sleeve device encounters fewer issues and problems than administering a drug such as Heparin, and the leg sleeve device was proven, to move contrast media injected in the blood along the patient's leg more effectively than the other methods described in the article.

As discussed above, the structural changes were directed to a sleeve that is softer; cools itself without compromising blood flow; is easy to use and apply; effectively eliminates irritation and pressure points; is flexible and elastic to improve patient mobility and is overall compliant with the existing expectations for clinical efficacy. To improve softness the wicking material, at the inner layer 12, was chosen to be a knitted sheet rather than an impervious non-woven such as polyvinyl chloride.

Figure 22:
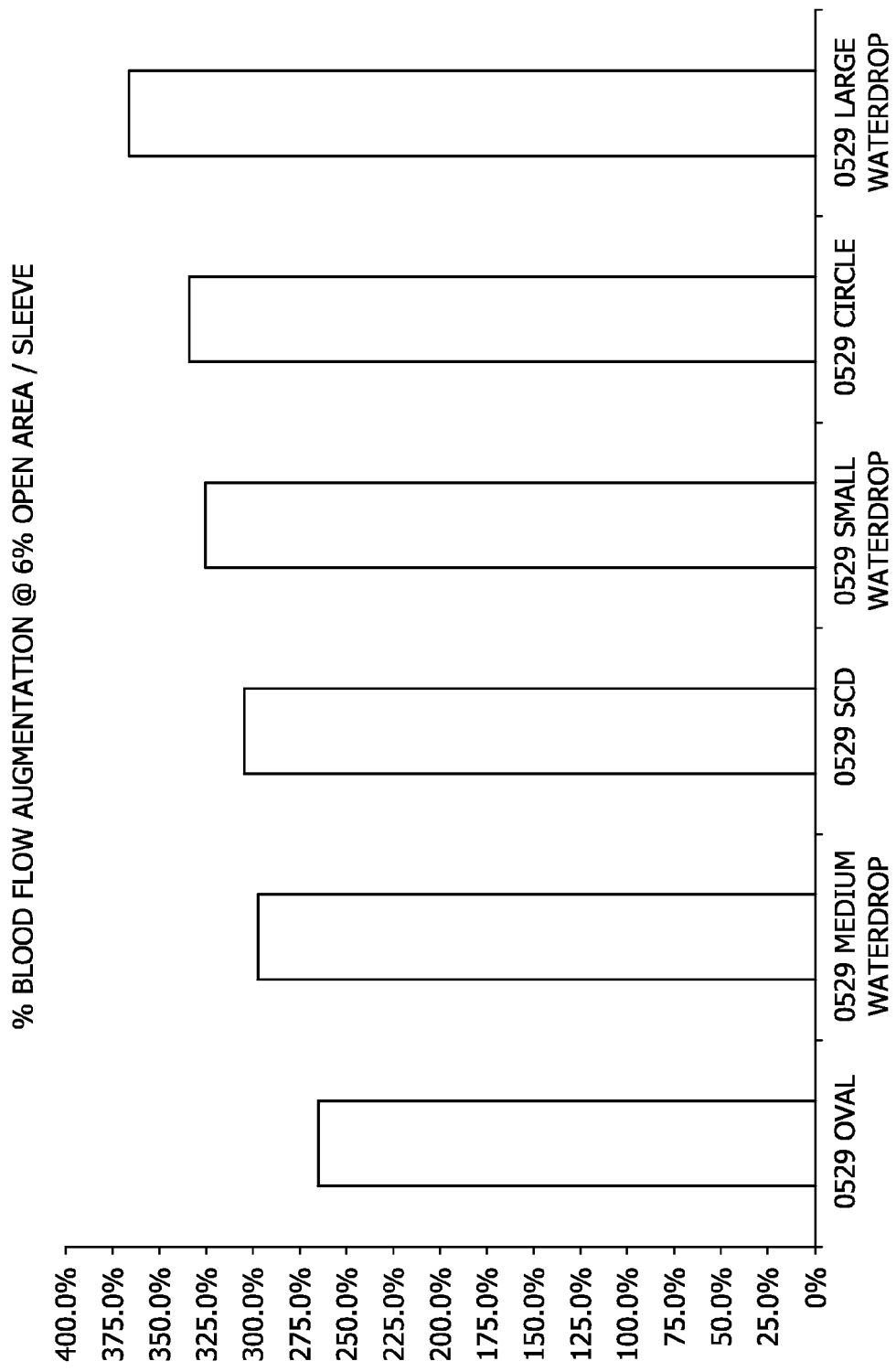
FIG. 22 is a percent of blood flow augmentation at 6% open area per sleeve for various opening shapes.

Cooling is achieved in at least one embodiment by a combination of wicking material and the openings 32. The openings allow for evaporation of the wicked moisture from a patient's limb. The wicking material 12 or inner layer was tested for the amount of fluid it could absorb from the patient's skin based on the assumption that the area between the skin and the inner layer 12 would be laden with sweat. This is called the wicking rate in terms of moisture absorbed. Once the wicking material absorbed moisture, the next wicking test is how far the material could move the absorbed moisture. This is called the wicking rate in terms of distance. The wicking rate in terms of distance is important because it impacts the location and number of openings 32, 34 in a bladder. Increasing the size and number of openings 32 impacts blood flow, as shown in FIG. 22, when the bladder pushes against the patient's limb to move blood to the heart. Findings shown in FIG. 22 suggest larger openings provide the highest blood flow, but a larger opening may cause blood pooling. The importance of the opening characteristics is described below.

The next test was the amount of open bladder space as a percentage of the sleeve area for maximum evaporation and still be considered a compliant device. This is called the % Opening to Patients Skin. The % Open to Patients Skin (through the bladder) was maximized to improve evaporation, while maintaining a clinical efficacy of blood flow—as found in the Model 9529 sleeves currently sold by Kendall. It is beneath the bladder where the moisture and heat are trapped, which provides the discomfort to the patient.

To summarize the evaporation improvement of a certain embodiment of the present invention, Table I is presented.

TABLE I

Comparison of Sleeve Evaporation

| Sleeve | Type | Circumferential Wrap of the Bladder around the Limb | % Opening to Patients Skin through bladder | % Evaporation of moisture at 1 hour | % Evaporation of moisture at 8 hours |
|---|---|---|---|---|---|
| 9529 | Knee | Yes | 0% | ~5% | 12-18% |
| Sleeve of the Present Invention | Knee | Yes | ~6% | 15% | 80-85% |
| Sleeve A | Knee | No | 0% | 35% | 90-95% |
| Sleeve B | Knee | Yes | 0% | ~5% | 35-40% |
| Sleeve C | Knee | No | 0% | 25% | 80-85% |

Figure 21:
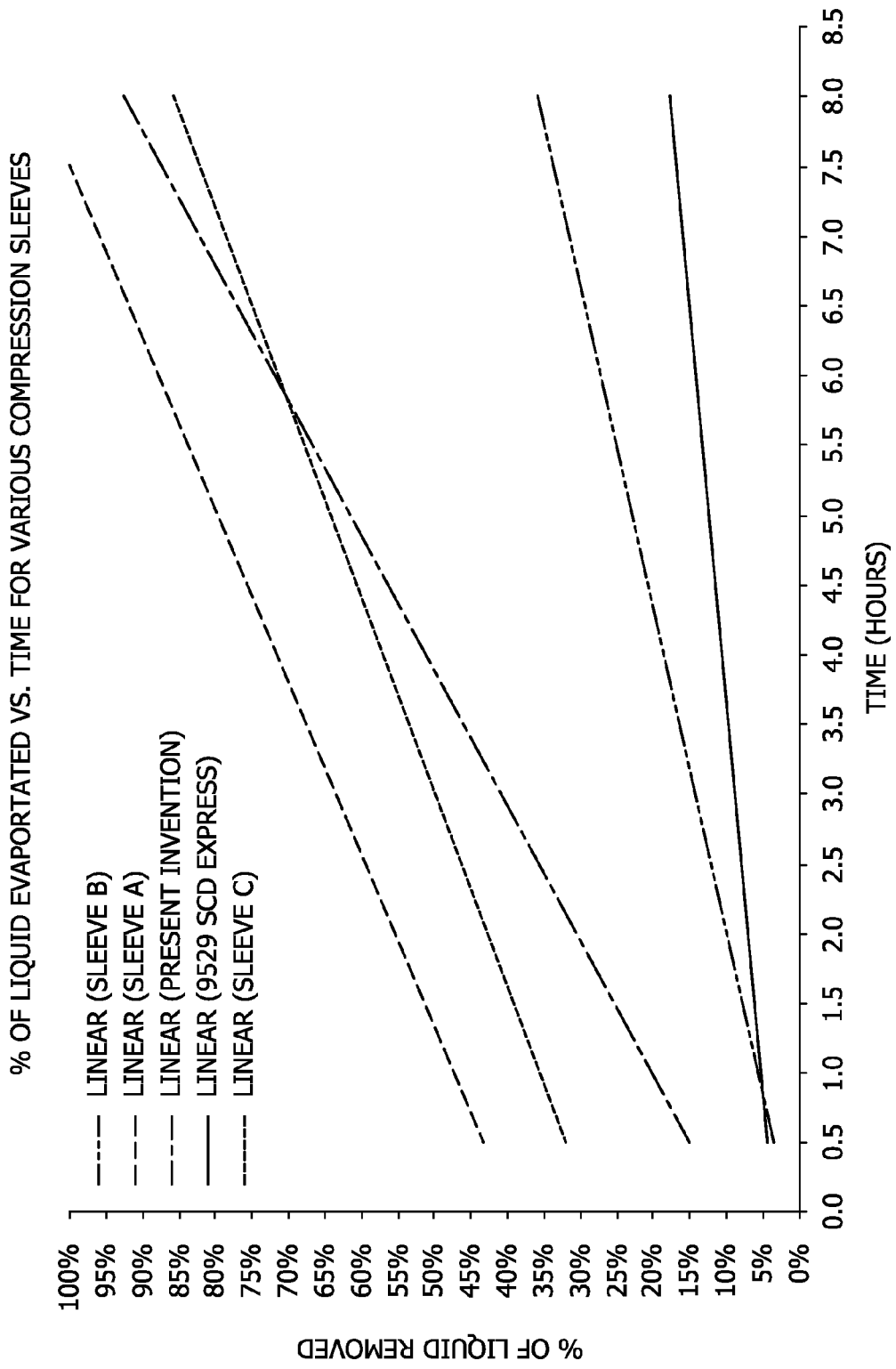
FIG. 21 is a graph of a percent of liquid evaporated over time for various compression sleeves including the sleeve of the present invention.

The sleeves tested were the Kendall model 9529, a sleeve constructed according to the principles of the present invention as an improvement to the 9529 or 9530 models, a Hill Rom® ActiveCare knee length sleeve, a Huntleigh® Flowtron sleeve and an AirCast® VenaFlow calf cuff. The competitor sleeves are represented as Sleeve A, B or C in the table. Table I demonstrates the unexpected results of the tested embodiment of the present invention. The tested embodiment of the present invention improves evaporation at least three times over the 9529 model within the first hour. At eight hours, the evaporation is about six times more than the 9529 model. The compression sleeve constructed according to the principles of the present invention gave final results comparable to Sleeves A and C, which do not have bladders that extend circumferentially around a limb or leg. The rate of evaporation is about 10% liquid evaporated per hour for the sleeve of an embodiment of the present invention as compared to the 9529 model at 1.35% rate. The % Liquid Evaporated over time is presented in FIG. 21.

Figure 20:
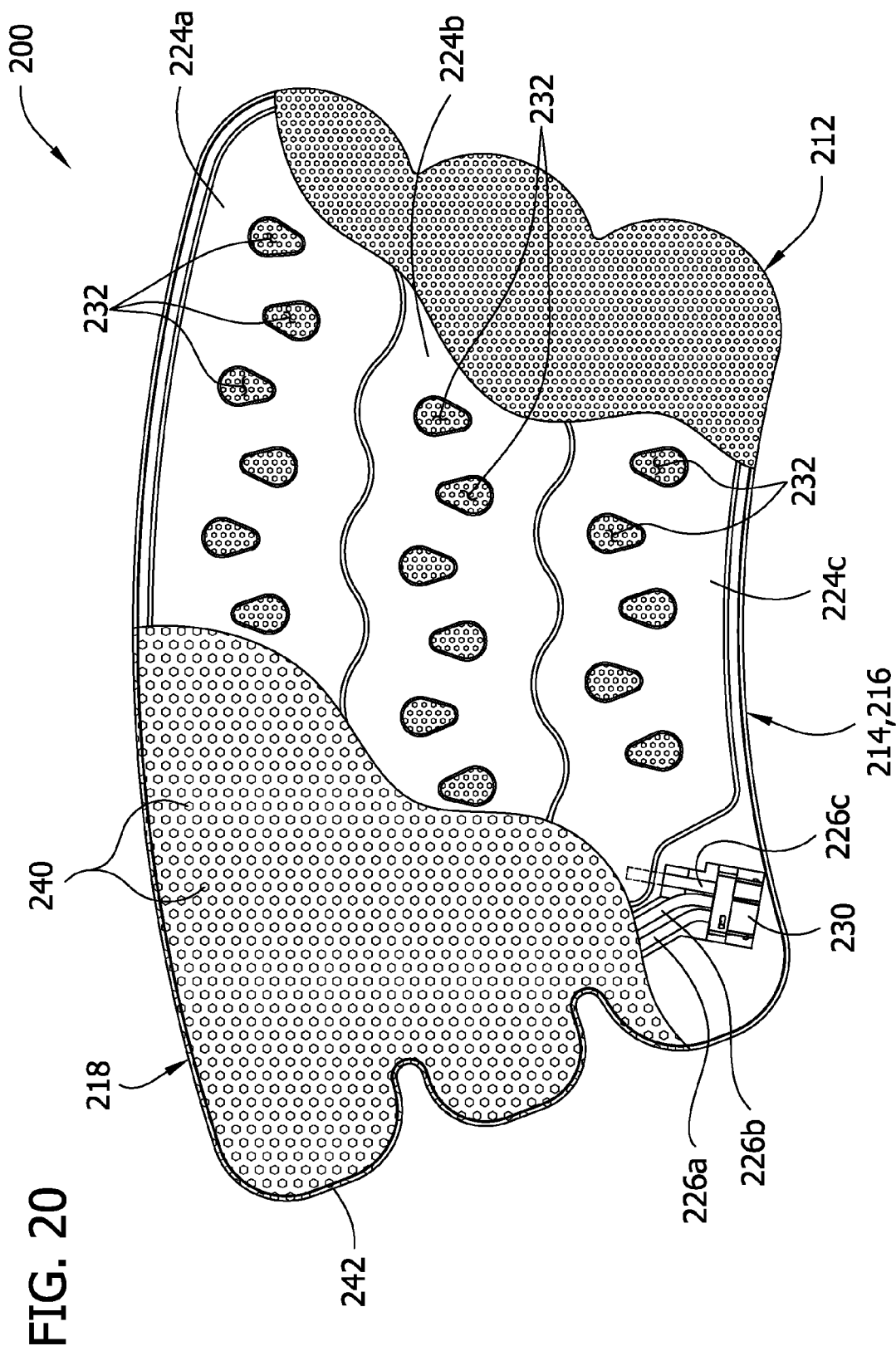
FIG. 20 is a front elevation of a compression sleeve of another embodiment with an outer cover and intermediate layers of the sleeve partially removed to show underlying layers.

The testing used new sleeves. All sleeves are knee length. For the tested embodiment of the present invention, the knee length sleeve is shown in FIG. 20. The moisture loss due to evaporation is dependent on the wicking properties of the inner layer 12, and the location, and size of the openings as well as their distribution pattern along and around the sleeve as shown in the inverted waterdrop configuration of FIG. 1.

The wicking test was devised to characterize the absorption and movement of wicked fluid at the inner layer of the SCD Express device sold by the Assignee of the present application. First the Applicant will describe the wicking test procedure. The results of the wicking test have been tabulated and are discussed hereinafter. The wicking material is the vehicle to absorb and move the otherwise trapped fluid beneath the impermeable bladder layer to the openings or external to the inside of the sleeve.

The optimal wicking rate and distance is dependent on the opening size and location which impacts blood flow or treatment. Kamm, described previously herein, reached the conclusion that the entire length of the veins should be emptied and filled as rapidly as possible. This does not mean a partial bladder can not meet the Kamm result, but too many openings in a full circumferential body wrap can introduce blood pooling. Thus, the key is to prevent blood pooling, which means the device is moving blood toward the heart, while maximizing cooling by maximizing the size and number of openings throughout the body wrap. The pattern of the openings 32 can help to maximize the number of openings by arranging the waterdrops as shown in FIG. 1 and FIG. 4.

Next, the Applicant evaluated and determined the size, type, location and number of openings for evaporating the wicked fluid. The opening size and location impacts comfort and blood flow. Too many openings may interfere with placing the sleeve on the limb because the sleeve is too loose and will not conform to the body part. Too many openings can reduce overall blood velocity. The pressure applied is directly related to blood velocity, that is, less pressure corresponds to lower flow rates of blood and uneven pressure may cause blood to pool at the openings. The sleeve pressure may act as a tourniquet if not properly placed on the user. Too many openings can cause adjacent bladder areas to fold on one another creating a possible tourniquet effect when secured using the hook and loop straps or flaps. If the openings are too large, this will lead to low pressure areas which can possibly lead to the pooling of blood.

The wicking test is used to experimentally quantify the wicking capability (i.e. absorption and movement) needed at the inner layer 12 of the compression sleeve 10. First, a sample is cut from the inner layer of the tested embodiment of the present invention and the prior art 9529 sleeve. The sample has a length of 6 in (15.24 cm) and a width of 0.75 in (1.91 cm). Other lengths may be used. The sample is marked with a longitudinal centerline so that the length of the strip is divided into two 3 in (7.62 cm) portions. The sample is weighed, and its weight is recorded as a starting weight. The sample is attached to a lab stand or other structure. The lab stand has an arm extending horizontally from a vertical post. The vertical position of the arm on the post is adjustable. The sample is attached adjacent to the free end of the arm so that the length of the sample extends downward, substantially perpendicular to the arm.

A 400 ml beaker of wicking fluid is placed underneath the sample as it hangs from the lab stand. The wicking fluid is room temperature tap water with red food coloring added for contrast against the sample. With the beaker underneath the sample, the lab stand arm is lowered so that the sample is submerged into the wicking fluid to the centerline of the sample. The sample remains submerged for 60 seconds. After 60 seconds, the lab stand arm is raised to completely withdraw the sample from the wicking fluid. The sample remains above the beaker for 10 seconds to allow any excess absorbed fluid to drip off. After 10 seconds, the sample is cut in half at its centerline and the lower half of the sample (i.e., the portion of the sample that was submerged in the wicking fluid) is discarded. The other half of the sample (i.e., the top portion) is weighed on a digital scale with a precision of $\frac{1}{100}$th gram. This weight is recorded, and the weight of the fluid that was wicked is calculated by subtracting the original half-weight of the sample from the weight of the top portion after wicking. The sample is laid on a plastic sheet, and the distance the wicking fluid progressed is measured from the cut end (i.e., the centerline) to the highest point to which the wicking fluid progressed. This distance is recorded.

After recording the progression of the wicking fluid, the sample remains untouched on the plastic sheet for 60 minutes at ambient room temperature conditions. After 60 minutes, the distance from the cut end of the top portion to the highest point to which the wicking fluid progresses is measured. This distance is recorded. Next, the top portion is weighed on the digital scale, and its weight is recorded.

Using the recorded data above, the average wicking rate is determined in terms of wicking distance for the material used at the inner layer, according to the following equation:

$WD_{60s}/60 \text{ s} = \text{distance/s}$, where $WD_{60s}$ is the average wicking distance of the four samples after 60 seconds.

Moreover, the average wicking rate in terms of amount of fluid wicked at the inner layer is calculated according to the following equation:

$WW_{60s}/60 \text{ s} = \text{amount wicked (g)/s}$, where $WW_{60s}$ is the average weight of the fluid wicked by the four samples after 60 seconds.

Using the above testing approach, the wicking capabilities of CoolDry model number CD9604 were determined. Four samples are cut from a sheet of the CoolDry model number CD9604, and the samples were weighed. A sample each has a dry weight of 0.40 grams, so that the half-weight, and therefore, the original weight of the top portion, is 0.20 grams. The mean weight of the top portion of the samples after 60 seconds in the wicking fluid totaled 0.49 grams, with the largest observed weight at 0.50 grams and the smallest weight at 0.48 grams. The mean weight of the fluid wicked is 0.29 grams for a sample. The mean wicking distance for the top portion of the samples after 60 seconds in the wicking fluid is 2.25 in (5.72 cm), with the largest distance recorded at 2.31 in (5.88 cm) and the smallest distance recorded at 2.19 in (5.56 cm). The mean weight of the top portion after 60 minutes at ambient room conditions is 0.213 grams, with the largest weight recorded at 0.22 grams and the smallest weight recorded at 0.21 grams. The mean wicking distance for the top portion after 60 minutes at ambient room conditions is 2.82 in (7.16 cm), with the largest distance recorded at 3.00 in (7.62 cm) and the smallest distance recorded at 2.63 in (6.68 cm).

Using the above data and equations, the average wicking rate in terms of distance ($WD_{60s}$) is about 0.0375 in/s (0.09525 cm/s). The average wicking rate in terms of amount of fluid wicked ($WW_{60s}$) is about 0.0048 g/s. The determined wicking rate and distance allows one to engineer the openings 32 about the sleeve for improving comfort while maintaining clinically acceptable blood flow. The mere inclusion of wicking material does not ensure the cooling affect to the patient. The wicking rate and distance must be correlated with the opening characteristics to ensure clinically effective blood flow augmentation, as tabulated in FIG. 22.

Preferably, the inner layer 12 has an average wicking rate in terms of distance ($WD_{60s}$) that is at least about 0.01 in/s (0.0254 cm/s) and an average wicking rate in terms of weight of fluid wicked ($WW_{60s}$) of at least about 0.002 g/s.

The construction of wicking layer, openings, bladder and outer layer is discussed. The openings must be sized and shaped to maintain the blood flow efficacy of a compression sleeve like model 9529 and to provide improved evaporation of moisture for increasing patient compliance. Referring to FIGS. 1 and 4, the sleeve 10 is constructed so that portions of the intermediate layers 14, 16 do not overlie the inner layer 12 so that moisture wicked by the inner layer 12 travels to open portions of the inner layer 12 and evaporates to the atmosphere. In this illustrated embodiment, each inflatable bladder 24a, 24b, 24c includes openings 32 that extend through the first and second intermediate layers 14, 16, respectively, to the inner layer 12. One way to form such an opening is to seal the intermediate layers 14, 16 together within the periphery of the respective bladder 24a, 24b, 24c using a continuous sealing line 34. The portions of the intermediate layers 14, 16 within a periphery of the sealing line 34 can be removed, such as by cutting, thereby forming the openings 32. Other ways of forming the openings 32 are within the scope of this invention. Once an opening size and pattern is determined, a metal die is cast to cut the openings in the PVC bladder material for the opposing sheets.

For the preferred embodiment, the opening shape is generally shaped like a waterdrop. Each opening 32 is tapered from a first round end portion toward a second, smaller round end portion. The openings 32 may be of other shapes, such as circles, ovals, and slits, without departing from the scope of the invention. The opening shapes may be inter-mixed at the bladder without departing from the scope of the invention. The waterdrop-shape provided the clinically efficacy, as found in FIG. 22, and this shape allowed for the largest number of openings within the available area without compromising the structural integrity of the bladder. The available bladder area varies from sleeve to sleeve because of seam line placement and other features. The more openings, at the same area per an opening, the greater area of the sleeve or body wrap that is available for evaporation. The circle and larger waterdrop-shape provide for larger low pressure, than the medium water-drop shape of the present. As stated above, low pressure areas as susceptible to the pooling of blood. Table II shows the medium waterdrop-shape as the preferred shape for the present invention. Other shapes are possible for compression devices of different shapes and sizes. The opening shape, size and distribution defining the % Open Area are proportional to the bladder size. As stated in the present invention, the Applicants determined about 6-10% Open Area per a Sleeve is preferred for maintaining clinical efficacy, while improving evaporation or cooling for patient comfort.

The water-drop shape has one of the highest number openings for the device as shown in FIGS. 1 and 20. Also, the area per an opening demonstrated good structural integrity upon wrapping as well as a shape that allowed an evenly distributed pattern at the sleeve. This provides for an optimal number of points of evaporation at a low % Open Area of a Sleeve, but not too low of % Open Area such that evaporation will not occur at a rate that improves patient comfort, thus, compliance. The more openings the less distance wicked moisture will need to travel to reach the atmosphere from beneath the layers of non-woven material.

TABLE II

Opening Shape Characteristics

| Opening Shape | Open Area per a Opening | # of Opening at a Sleeve | Open Area of a Sleeve |
|---|---|---|---|
| 0529 Oval | 0.81 | 23 | 6.7% |
| 0529 Small Waterdrop | 0.27 | 27 | 2.6% |
| 0529 Medium Waterdrop | 0.61 | 27 | 5.9% |
| 0529 Large Waterdrop | 1.08 | 20 | 7.7% |
| 9529 SCD Express | 0 | 0 | 0.0% |
| 0592 Circle | 0.81 | 23 | 6.7% |

The opening size correlated with the wicking rate and distance determines the evaporation of the wicked moisture.

Referring to FIG. 22 the blood flow augmentation of the medium waterdrop is substantially similar to the knee-length 9529 sleeve at 6% Open Area of a Sleeve. This means the clinical efficacy is maintained while substantially improving comfort.

The measured blood flow augmentation is the amount of additional blood moved with treatment, sequential compression, as compared to no treatment. No treatment would be the blood flow of the patient at rest. Blood flow augmentation, in its measure, includes blood velocity and blood vessel diameter of a patient. Blood flow augmentation is a more accurate measure because it removes the affect of differing blood vessel size between the patients. Another measure is peak velocity augmentation. This is a measure of the highest blood flow velocity reached during a treatment cycle. The faster the velocity the more shear imparted to the blood to help prevent the formation of blood clots.

FIG. 22 shows the compression sleeve having a 6% open area and medium waterdrop-shaped openings each having an area of about 0.6 in$^2$ is most similar to the current clinical efficacy of Kendall's 9529 model. The sleeve having the medium waterdrop-shaped openings produced a blood flow augmentation substantially at the 9529 SCD Express level while increasing evaporation of moisture more than 10% after one hour of use compared to the current 9529 model sleeve. The peak velocity of the sleeve having the medium waterdrop-shaped openings and the 9529 device were within percentage points of each other, while the circle was the closest. Though the sleeve having the large waterdrop-shaped openings produced the greatest blood flow augmentation, the medium waterdrop-shaped openings are preferred because the large open areas of the large waterdrop-shaped openings will likely cause blood pooling. The results of Kamm, and the findings of Nicolaides, Olson and Best suggested the more sleeve area providing compression the less likely there is the possibly of blood to pool. Blood pooling is caused by a localized area of low pressure created by openings or such features between areas of higher pressure.

As derived from the evaporation and hemodynamic testing, each waterdrop-shaped opening has an area between about 0.50 in$^2$ (3.23 cm$^2$) and about 0.90 in$^2$ (5.81 cm$^2$), and preferably about 0.61 in$^2$ (3.94 cm$^2$). In one example, the openings 32 comprise between about 2% and about 20% of the total surface area of the respective inflatable bladder, and more preferably between about 4% and about 15% of the total surface area of the respective inflatable bladder 24$a$, 24$b$, 24$c$. Each opening 32 may comprise between about 0.5% and about 1.2% of the total surface area of the respective bladder 24$a$, 24$b$, 24$c$. The total percent surface occupied by the openings is calculated by summing the areas of the openings and dividing the sum by the total surface area of the uninflated bladder, where the total surface area of the uninflated bladder includes the areas of the openings. The percent surface area occupied by each opening is the area of that one opening divided by the total surface area of the uninflated bladder, where the total surface area of the uninflated bladder includes the areas of the openings.

It is understood that the percentage of openings 32 may depend on the type of compression sleeve. In an embodiment for a thigh-length compression sleeve, such as the illustrated sleeve, the openings more preferably comprise between about 4% and about 6% of the total surface area of the respective bladder. For example, in the illustrated embodiment, the openings 32 in the distal bladder 24$c$ comprise about 4.36% of the total surface area of the respective inflatable bladder; the openings in the intermediate bladder 24$b$ comprise about 5.00%; and the openings in the proximal bladder 24$c$ comprise about 5.96%. Each opening 32 may comprise between about 0.5% and about 1.0% of the total surface area of the respective inflatable bladder. For example, in the illustrated embodiment, each opening 32 in the distal bladder 24$c$ comprises about 0.87% of the total surface area of the respective inflatable bladder; each opening in the intermediate bladder 24$b$ comprises about 0.72%; and each opening in the proximal bladder 24$c$ comprises about 0.60%. In the illustrated embodiment, the total surface areas of the distal, intermediate and proximal bladders are 70.01 in$^2$ (451.68 cm$^2$), 81.05 in$^2$ (522.90 cm$^2$) and 102.42 in$^2$ (660.77 cm$^2$), respectively. For example, the sleeve can have at the distal bladder 24$c$ 5 openings; at the intermediate bladder 24$b$ 7 openings; and at the proximal bladder 24$a$ 10 openings. Moreover, all of the openings have the same area of 0.61 in$^2$ (3.94 cm$^2$). An opening's area may vary from opening to opening.

In an embodiment for a knee-length sleeve, the openings more preferably comprise between about 7% and about 10% of the total surface area of the respective inflatable bladder. In one example, openings in the distal bladder of a knee-length sleeve may comprise about 9.52% of the total surface area of the respective inflatable bladder; the openings in the intermediate bladder may comprise about 8.60%; and the openings in the proximal bladder may comprise about 7.77%. Each opening may comprise between about 0.5% and about 1.5% of the total surface area of the respective inflatable bladder. For example, each opening in the distal bladder may comprise about 1.20% of the total surface area of the respective inflatable bladder; each opening in the intermediate bladder may comprise about 0.96%; and each opening in the proximal bladder may comprise about 0.77%. In the illustrated embodiment, the total surface areas of the distal, intermediate and proximal bladders are 51.25 in$^2$ (330.64 cm$^2$), 63.84 in$^2$ (411.87 cm$^2$) and 78.48 in$^2$ (506.32 cm$^2$), respectively. For example, the sleeve can have at the distal bladder 8 openings;

at the intermediate bladder 9 openings; and at the proximal bladder 10 openings. All of the openings have the same area of 0.61 in$^2$ (3.94 cm$^2$).

It is contemplated that the openings 32 may comprise a greater or lesser percent of the total surface area of the inflatable bladder than given above. However, there is a limit to the percent opening in an inflatable section. Experimentally total opening area above 10% is found to be uncomfortable to the patient, this relationship of opening size, the number of openings and their location is bounded by an upper and lower percent opening. In preferred embodiments of the present invention, the sleeve extends around the full circumference of the leg (or limb). However, the use of openings registered with wicking material can be included in other sleeves such as Huntleigh®, Hill-Rom® and Aircast® that have bladders that do not extend around the full circumference of the limb.

Opening location is important for comfort, use and blood flow. Recent internal studies at the Applicants demonstrated that blood flow for the current SCD Express models did not vary significantly when rotated about the wearer's leg. This further supports a symmetrical distribution of openings around and along the patient's limb for maintaining blood flow augmentation as was found in the testing shown in FIG. 22.

With respect to each bladder 24a, 24b, 24c, the openings 32 are arranged in a distal row 36 and a proximal row 38 (FIG. 4). Both rows 36, 38 extend across the respective bladder 24a, 24b, 24c along the width W of the sleeve 10. As depicted in the drawings, the openings 32 in each proximal row 38 are inverted medium waterdrop-shaped openings in that the openings taper distally, while the openings in each distal row 36 are right-side-up in that the openings taper proximally. The openings 32 in each distal row 36 are offset along the width W of the sleeve from the openings in the respective proximal row 38. Offsetting the openings 32 distributes the openings evenly across the surface area of the bladders 24a, 24b, 24c, thereby increasing the breathability of the bladders and the overall breathability of the sleeve 10 without compromising the structural integrity of the bladders or their ability to apply compressive force (i.e., prophylaxis treatment) to the leg or body part. Moreover, offsetting the openings in the respective distal and proximal rows 36, 38, also makes the bladders 34a, 34b, 34c more stretchable in the widthwise direction of the sleeve 10. The above configuration allowed for one of the highest number of openings as found in Table II. In another embodiment described below the addition of peripheral openings 39 improved the effective or useable % Open area of a Sleeve as explained below.

Other ways of allowing fluid wicked by the inner layer 12 to evaporate, besides the openings 32 through the bladders are within the scope of the invention. For example, referring to FIG. 14, another embodiment of the sleeve is generally indicated at 10a. The sleeve is similar to other embodiments in the present invention, and therefore corresponding parts have corresponding reference numerals. The difference between this sleeve 10a and the previous sleeve 10 is that in addition to the bladder openings 32, peripheral openings 39 are formed through portions of the intermediate layers 14, 16 which do not define the bladders 24a, 24b, 24c (i.e., outside the peripheries of the bladder seam lines 22a, 22b, 22c). More specifically, the peripheral openings 39 are generally formed through portions of the intermediate layers 14, 16 corresponding to side flaps 41a, 41b, or 41c of the sleeve 10. The peripheral openings 39 are generally waterdrop-shaped but are larger than the bladder openings 32. Side flap 41a has three peripheral openings 39, side flap 41b has two openings and side flap 41c has 1 opening. Like the bladder openings 32, the peripheral openings 39 allow moisture wicked by the inner layer 12 to evaporate to the atmosphere. The peripheral openings 39 most commonly overlap or entirely overlie the sleeve 10 when the sleeve is wrapped circumferentially around the wearer's leg and secured to itself. In that situation, the portions of the inner layer 12 in registration with the peripheral openings 39 are not in direct contact with the wearer's leg. Moisture wicked by portion of the inner layer 12 in contact with the wearer's leg will move to the portions of the inner layer 12 in registration with the peripheral openings 39 because the openings allow evaporation of the wicked moisture (i.e., drying). Accordingly, the peripheral openings 39 provide more area for moisture to be evaporated from the inner layer 12, which reduces the number and size of openings in the bladder area.

Figure 14:
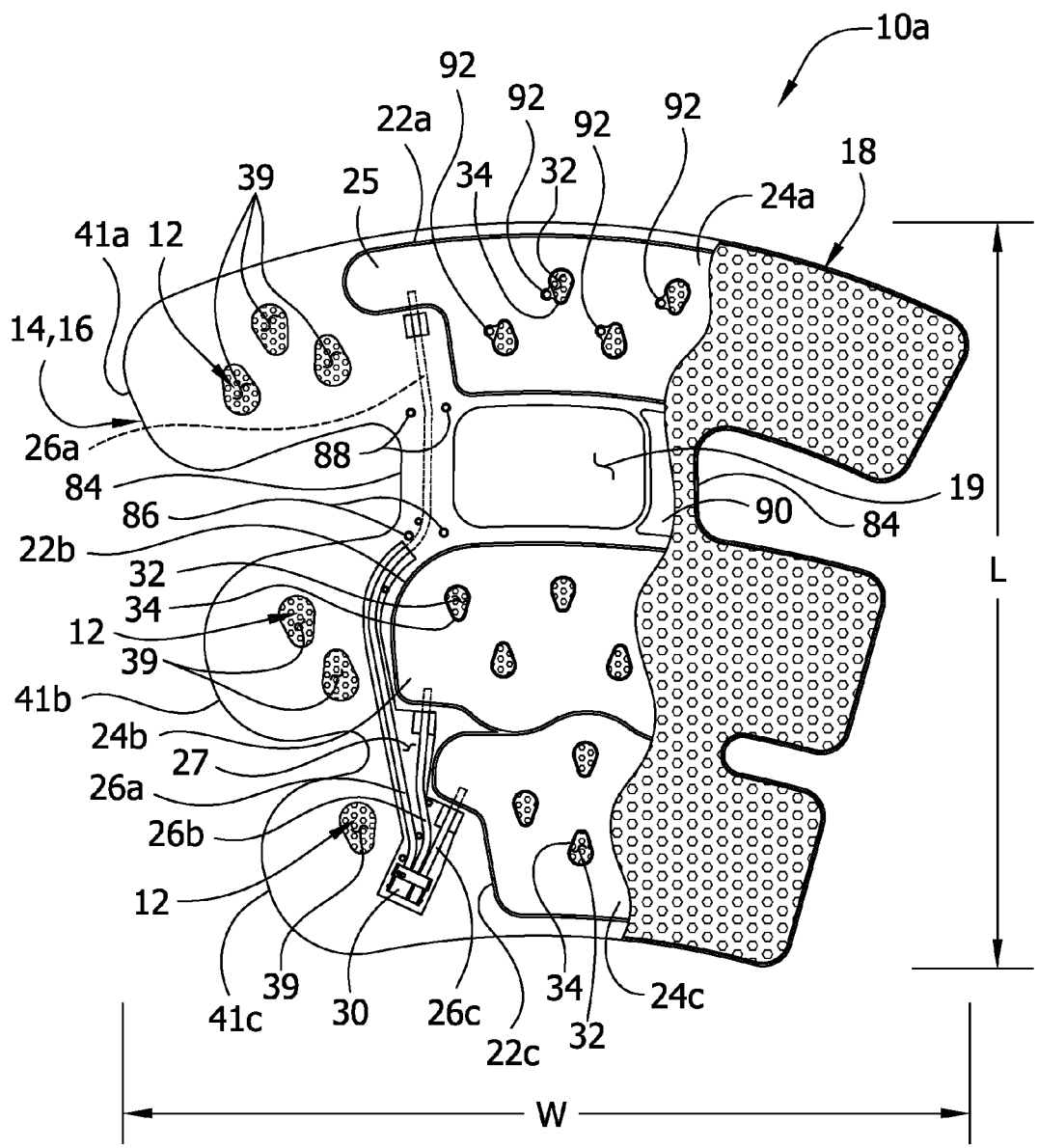
FIG. 14 is a front elevation of another embodiment of a compression sleeve with an outer cover partially removed to show intermediate layers and an inner layer.
Figure 15:
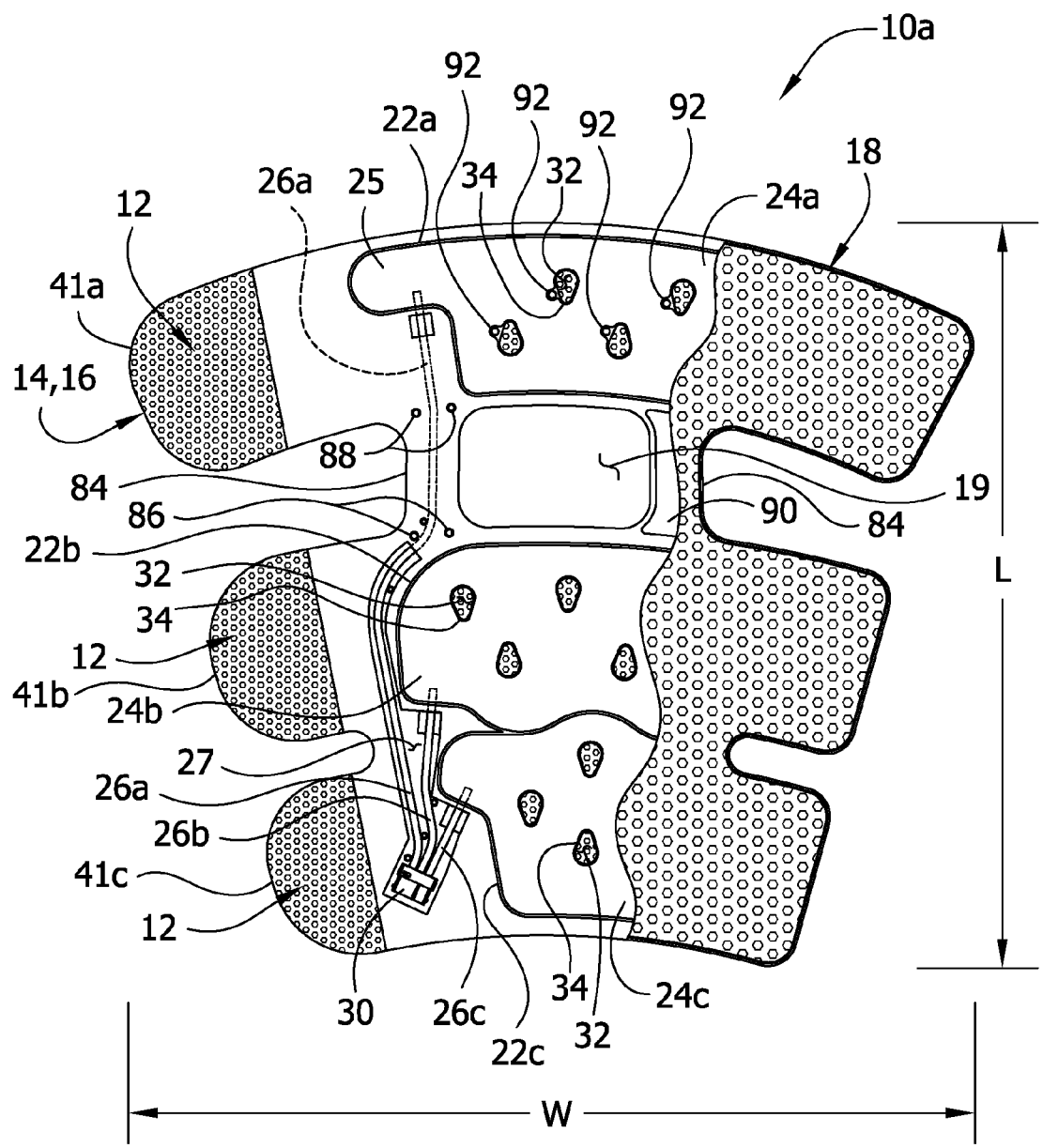
FIG. 15 is a front elevation of yet another embodiment of a compression sleeve with an outer cover partially removed to show intermediate layers and an inner layer.

Referring to FIG. 15, in yet another example, the size and shape of the intermediate layers 14, 16 are such that the peripheries of the layers do not completely cover or overlie the inner layer 12, whereby the inner layer 12 is exposed to the atmosphere. In the illustrated embodiment, the flaps 41a, 41b, 41c project laterally outward from lateral edges of the intermediate layers 14, 16. Through this construction, large areas of the inner layer 12 forming the flaps 41a, 41b, 41c are not covered by the intermediate layers 14, 16 and wicked fluid is allowed to evaporate through these areas. This embodiment functions in a similar manner as the embodiment illustrated in FIG. 14, in that it allows more moisture wicked by the inner layer 12 to be evaporated to the atmosphere. Other ways of allowing moisture wicked by the inner layer 12 to evaporate into the atmosphere are within the scope of the invention. The peripheral openings 39 allow for fewer openings at the inflatable section thereby improving blood flow to its theoretical maximum while maintaining the cooling affect for the patient.

With the addition of the peripheral openings 39 in the intermediate layers 14, 16 (FIG. 14) and/or the portions of the inner layer 12 not overlaid by the intermediate layers (FIG. 15), "a total open percentage" of the inner layer may be calculated, correlating to the total surface area of the inner layer not overlaid or covered by the intermediate layers 14, 16. The total open percentage of the inner layer 12 is calculated by summing the surface areas of all portions of the inner layer that are not overlaid or covered by the intermediate layers 14, 16 and dividing this sum by the surface area of the inner layer. The surface area of the inner layer 14 is determined by the periphery dimensions of the inner layer, irrespective of any holes or openings in the layer. It is noted that the "total open percentage" of the inner layer 12 of the previous embodiment illustrated in FIGS. 1-7 is equal to the total surface area occupied by the bladder openings 32 of all the bladders 24a, 24b, 24c divided by the total surface area of the bladders because the remainder of the intermediate layers 14, 16 completely overlies or covers the inner layer. However, in the present embodiments (FIGS. 14 and 15), the total open percentage of the inner layer 12 is calculated by summing the surface areas occupied by the openings 32 in the bladders 24a, 24b, 24c (correlating to the total surface area of the inner layers in registration with the openings and therefore "open") together with surface areas of any other portions of the inner layer that is not overlain or covered by the intermediate layers. In FIG. 14, the total open percentage of the inner layer 14 is equal to the sum of the areas of bladder openings 32 and the areas of the peripheral openings 39 divided by the surface area of the inner layer.

In FIG. 15, the total open percentage of the inner layer 14 is equal to the sum of the areas of bladder openings 32 and the surface areas of the other portions of the inner layer not covered by the intermediate layers 14, 16 divided by the surface area of the inner layer. In one example, the total open percentage of the inner layer 12 may be greater than about 10%, more specifically, between about 10% and about 20%, without patient discomfort when the openings are located at the sleeve itself. In another example, the total open percentage of the inner layer may be greater than 20%. Patient discomfort can result when the sleeve folds on itself or just does not stay snug or secure around a patient's limb. Therefore flaps are needed to hold the wrap onto the patient's body part. Prior art flaps would cover openings at the sleeve. By placing openings at the flaps as shown as peripheral openings 39, the openings 39 are positioned to overlay the openings 32 and the total open percentage of the wicking material is maintained. Also, changing the opening 32 distribution not to coincide with the flaps is within the scope of this invention. Prior art devices such as U.S. Pat. No. 6,592,534 to Rutt show flaps 20 that wrap over the body of the foot cuff with no openings therethrough. Even Roth (U.S. Pat. No. 7,044,924) which has openings at the flaps for handles does not describe aligning the flap openings with the openings at seams of its sleeve. At FIG. 2A of Roth, the handles 222 are off the sleeve and over the loop material at the sleeve outer layer.

Figure 18:
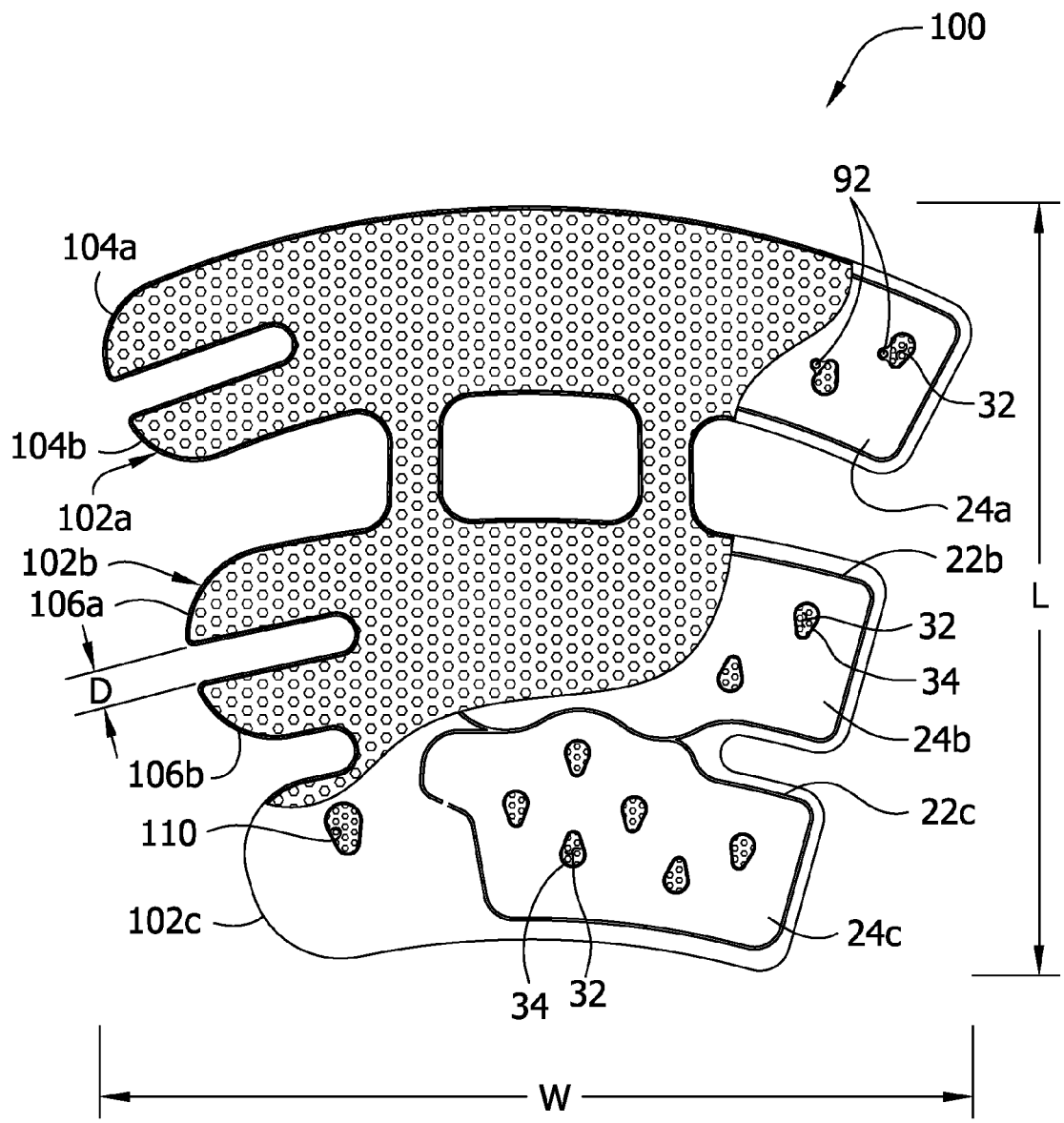
FIG. 18 is a front elevation of another embodiment of a compression sleeve with an outer cover partially removed to show underlying layers.
Figure 19:
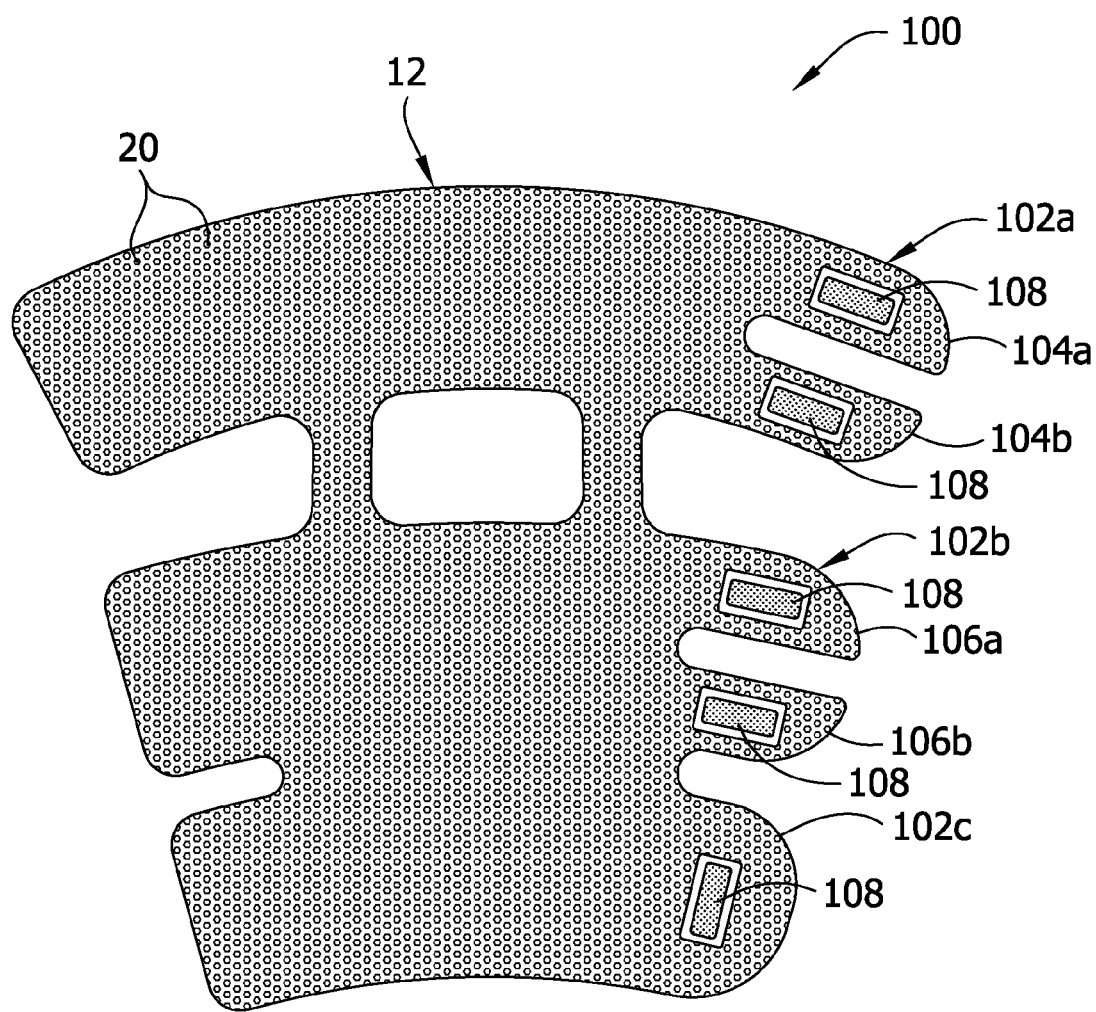
FIG. 19 is a rear elevation of the embodiment of FIG. 18.

Referring to FIGS. 18 and 19, yet another embodiment of a compression sleeve is generally indicated at 100. The flaps described provide an adjustable means to secure the wrap around the patient's limb. The flaps described are typically found in the prior art, such as U.S. Pat. No. 6,592,534 to Rutt, to be made of uniform, impermeable sheet with hook or loop material corresponding to loop or hook material at the outer cover. The difference is the flaps of the illustrated embodiment have an opening or cut out section from the flaps 102a, 102b, 102c, which generally corresponds to the opening at the outer cover or bladder area of the sleeve. Thus, the open flap allows wicked moisture to evaporate to the atmosphere, as it is in registration with wicking material at the patent's skin. This will reduce the number of openings otherwise need to meet the evaporation rates needed to provide a cooler sleeve during use.

This embodiment is similar to the sleeve 10 illustrated in FIGS. 1-7, and therefore, like components are indicated by corresponding reference numerals. The difference between the present sleeve 100 and the sleeve 10 is that the present sleeve has bifurcated or split proximal and intermediate flaps 102a, 102b, each being indicated generally in FIGS. 18 and 19. The amount of split or bifurcated distance "D" depends on the location and distribution of the openings 32, so the opening distance "D" overlies the maximum number of openings 32. Each of the proximal and intermediate flaps forms a pair of fingers 104a, 104b and 106a, 106b, respectively, on which a fastening component 108, such as a hook component, is secured. A peripheral opening 110 is formed through the intermediate layers 14, 16 at a distal, non-bifurcated flap 102c for purposes described above with respect to the embodiment illustrated in FIG. 14. The bifurcated flaps 102a, 102b make the sleeve 100 more adjustable when securing it circumferentially around a patient's leg to allow for different leg proportions among patients and to provide more comfort for the patient. It is understood that the flaps may be divided into more than two fingers and that different ones or all of the flaps may be bifurcated.

Figure 16:
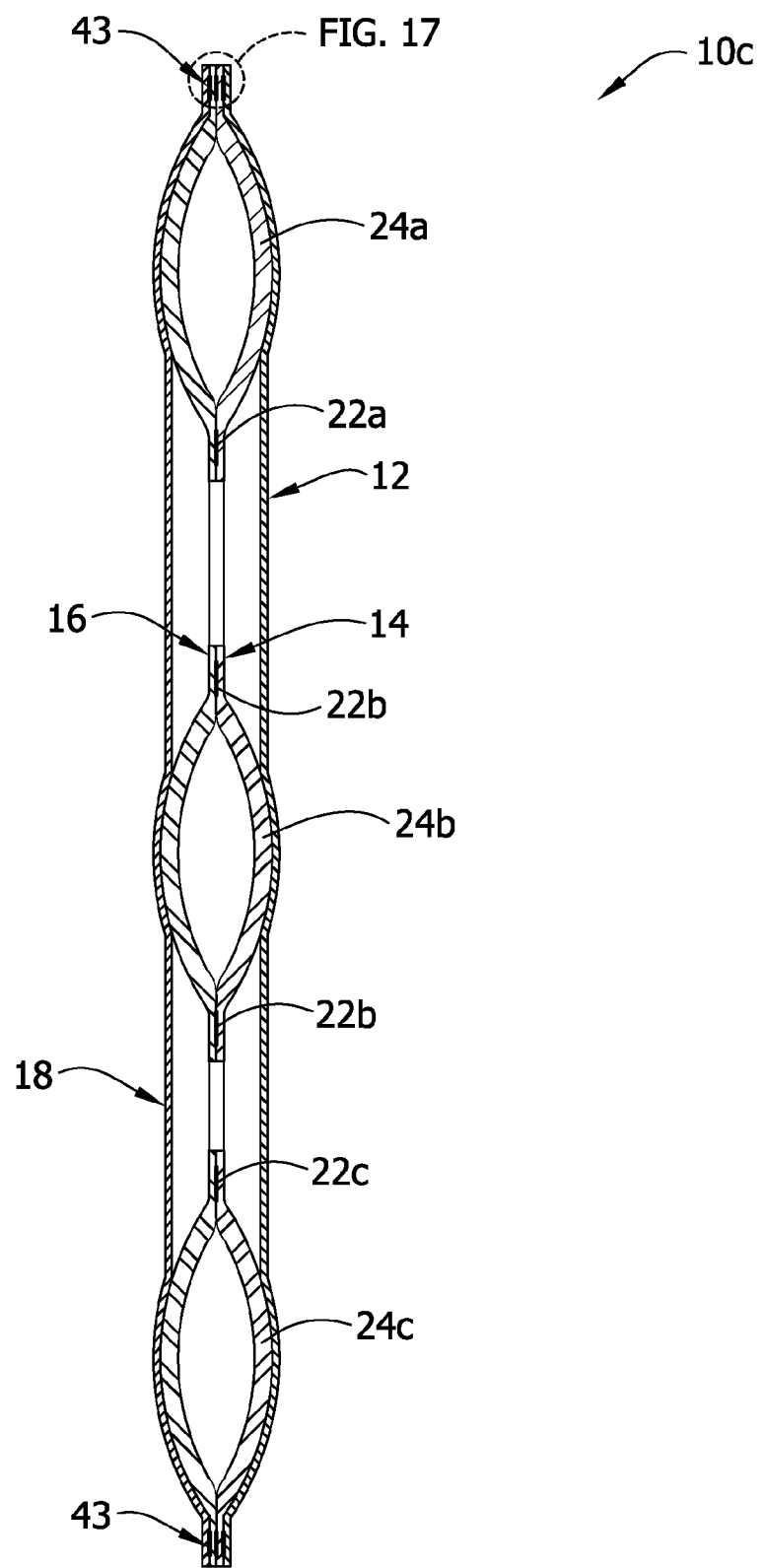
FIG. 16 is a section of another embodiment of a compression sleeve, similar to FIG. 5 with components of the sleeve being secured together along a single peripheral seam line.
Figure 17:
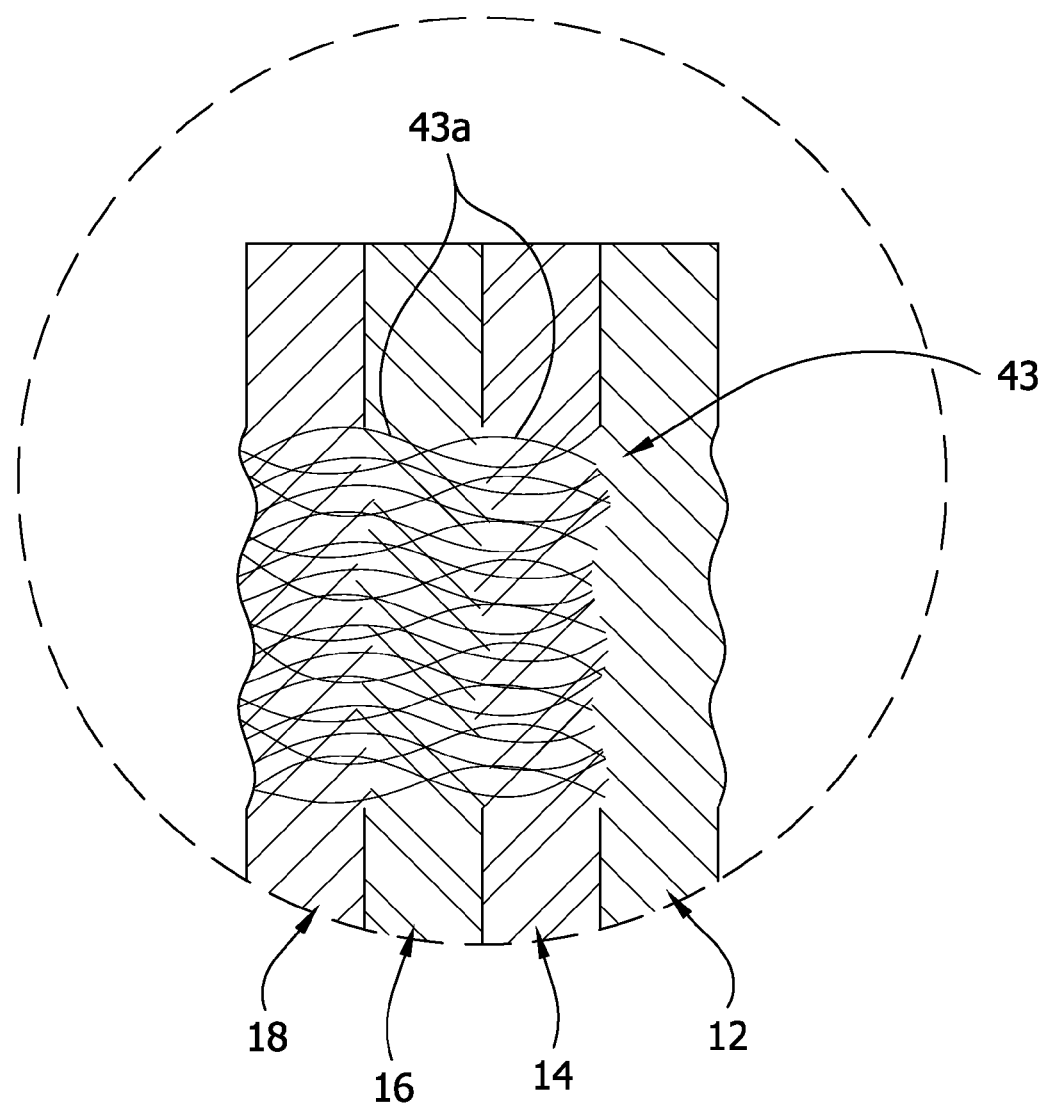
FIG. 17 is an enlarged detail of the seam line illustrated in FIG. 16.

Referring to FIGS. 16 and 17, in another embodiment of the sleeve, generally indicated at 10c, the inner layer 12, the intermediate layers 14, 16 and the outer cover 18 are secured together along a single seam line 43, which runs along the peripheries of the outer cover and the layers. In this embodiment, it has been found that the seam line 43 allows fluid wicked by the inner layer 12 to travel through the intermediate layers 14, 16 to the outer cover 18 and evaporate into the atmosphere. The outer cover 18, the intermediate layers 14, 16 and the inner layer 12 are secured to one another in a single welding step, such as by a radiofrequency welder, after the layers have been stacked on one another. During this step, the intermediate layers 14, 16 are heated and softened along the seam line 43. The softening of the intermediate layers 14, 16 is one way the fibers 43a (FIG. 17) of the inner layer 12 extend entirely through the seam line to the exterior of the compression sleeve 10. The fibers 43a are distributed uniformly throughout inner layer 12. Thus, the inner layer 12 is able to wick fluid through the seam line 43 for evaporating into the atmosphere. The wicking layer 12 can be placed between layers 14, 16 at a spot weld. A seam line may be positioned along or around the compression device not just at the peripheral of a bladder.

Referring to FIGS. 1 and 2, the outer cover 18 of the compression sleeve 10 is constructed of a single sheet of material. The outer cover 18 is breathable and has a multiplicity of openings 40 or perforations so that it has a mesh construction to provide even more breathability. A suitable material for the outer cover 18 may be a polyester mesh. The rate of evaporation from the openings is improved by treating the fibers of the mesh material with a hydrophilic material. The mesh material will absorb the wicked fluid more readily. Wicking fibers of this type are indicated generally at 21 in FIG. 7. These hydrophilic fibers lower the surface tension of the mesh material to allow bodily fluids to more easily absorb into the fibers and spread therethrough for a more efficient evaporation of the wicked fluid. Absorbing fluid more readily will allow the fluid to move to the open areas more quickly for evaporation. The capillary effect is made more efficient as the absorbed fluid at the openings is moved more quickly through the mesh outer cover 18.

Figure 5:
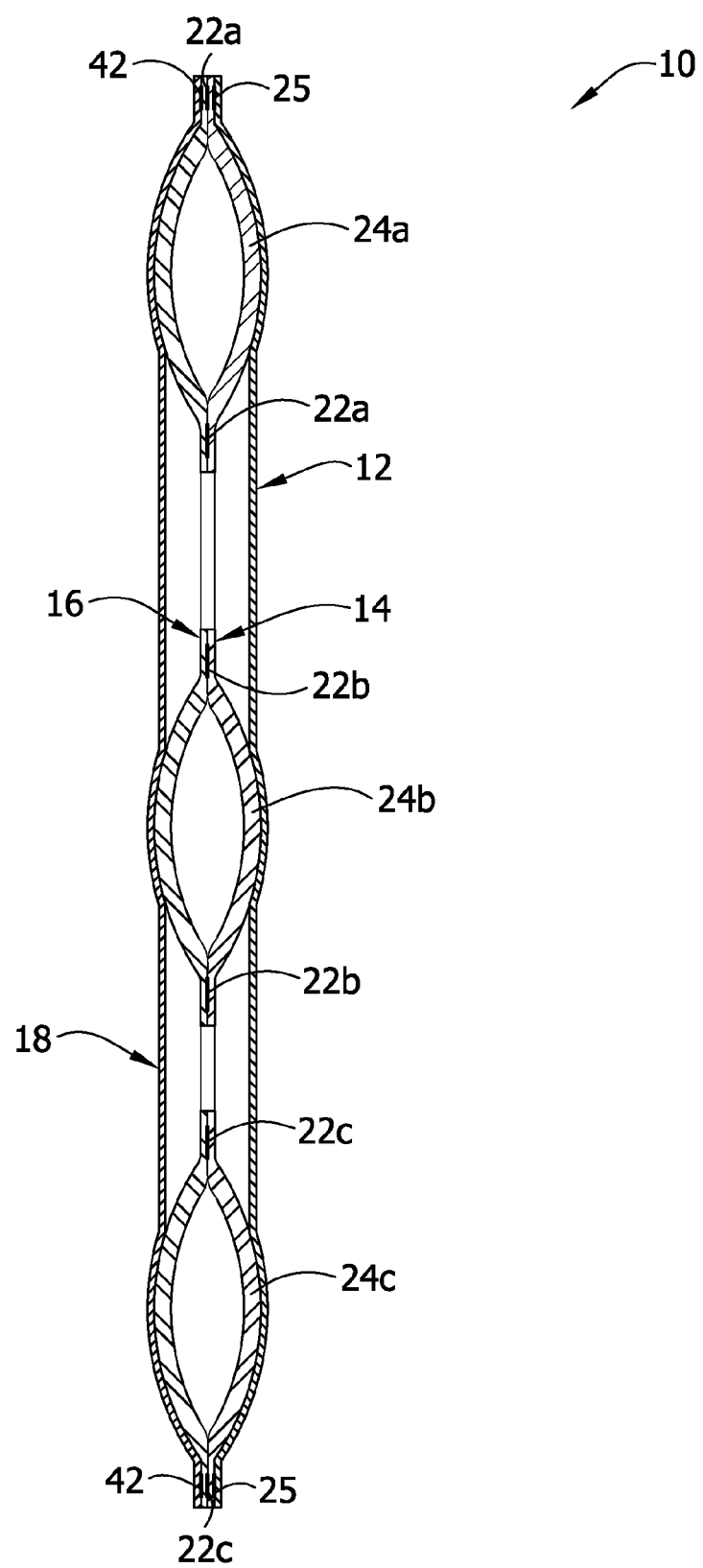
FIG. 5 is a longitudinal section of the compression sleeve with inflatable bladders of the sleeve in an inflated state.
Figure 6:
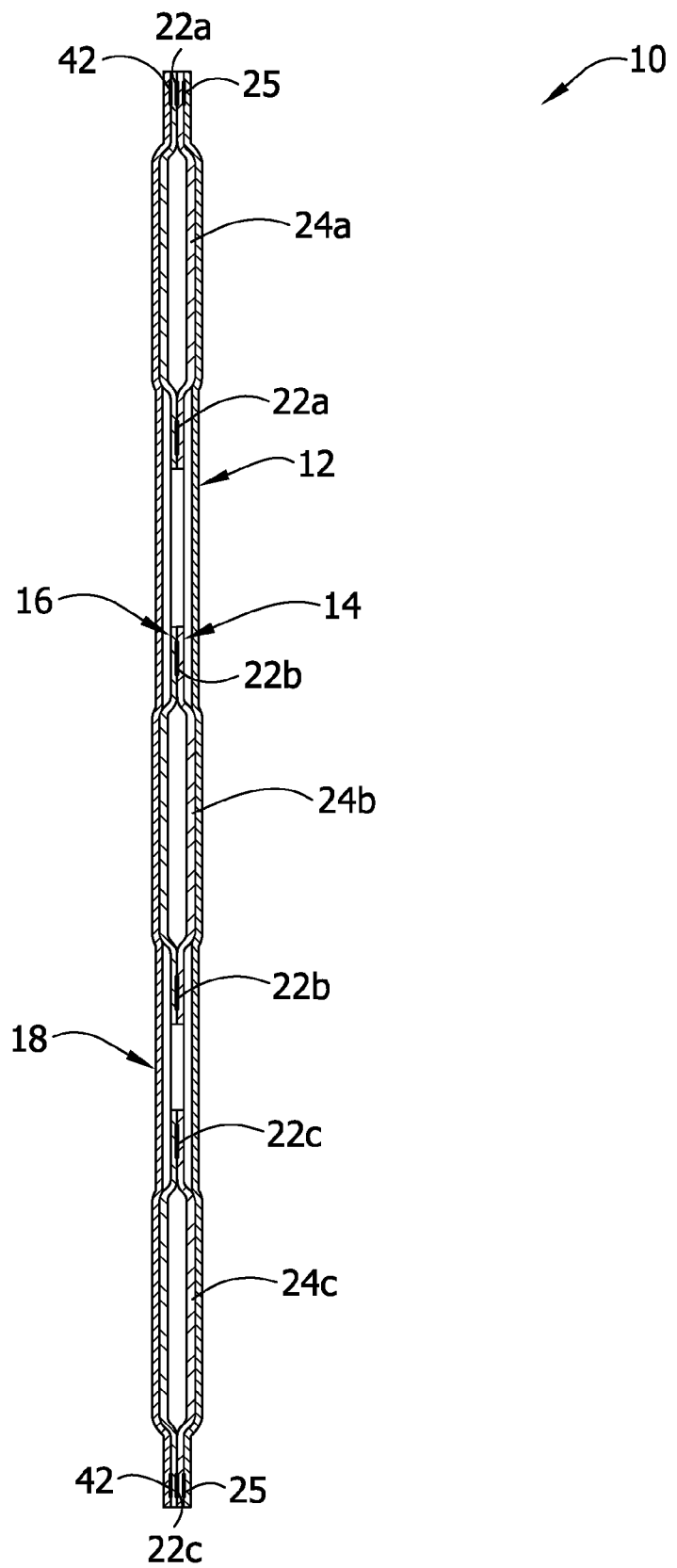
FIG. 6 is a longitudinal section of the compression sleeve with the inflatable bladder in a deflated state.

Referring to FIGS. 1, 5 and 6, the outer cover 18 is secured to the second intermediate layer 16 along seam line 42, which runs only adjacent to the outer periphery of the second intermediate layer so that the bladders 24a, 24b, 24c are free from attachment to the cover. The second intermediate layer 16 may be secured to the inner layer 12 by RF welding or adhesive or in other suitable ways.

Figure 7:
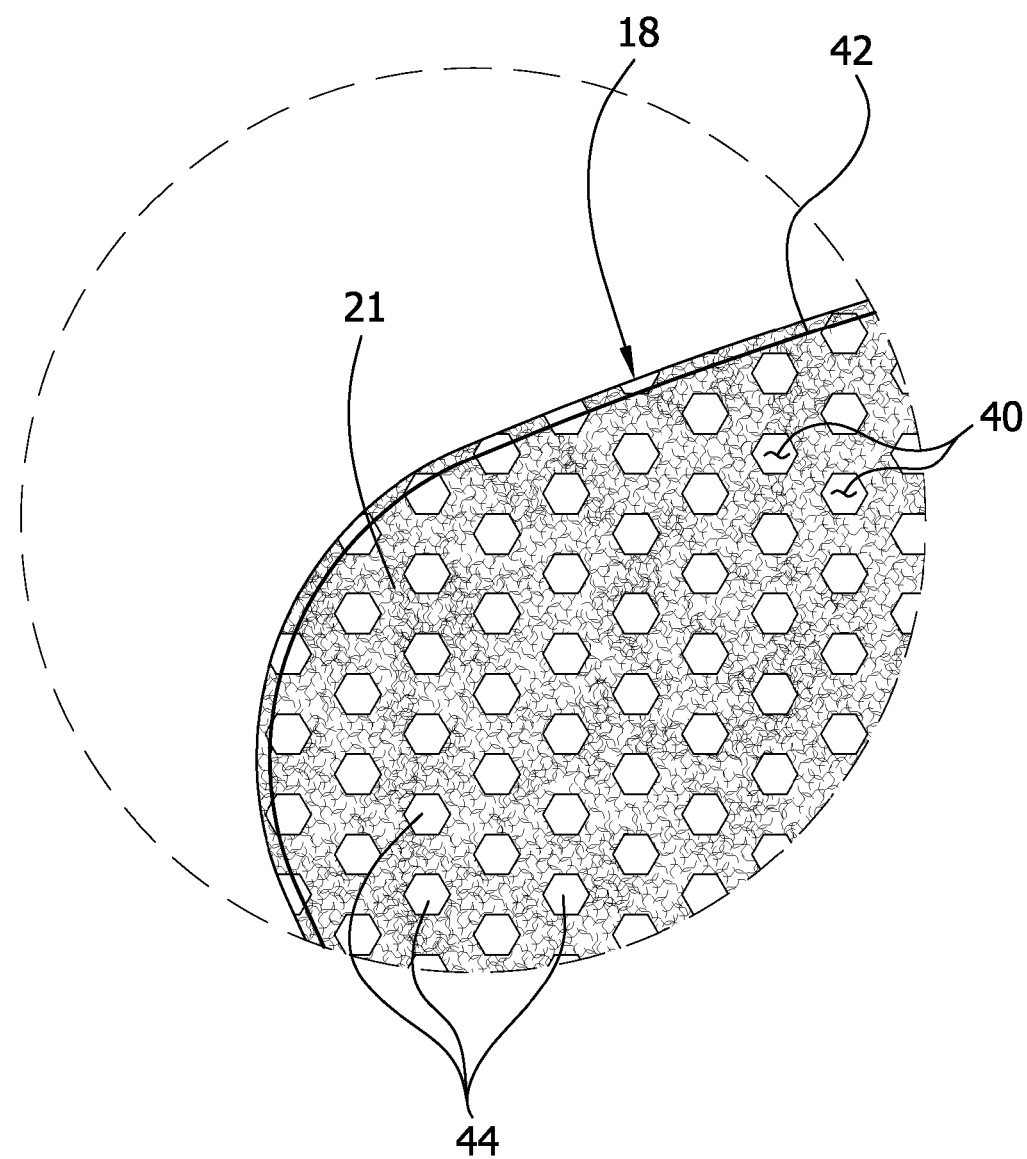
FIG. 7 is an enlarged fragmentary elevation of the outer cover illustrating loop material.

Referring to FIGS. 1 and 7, the entirety of an outer surface of the outer cover 18 also acts as a fastening component of a fastening system for securing the sleeve 10 to the limb of the wearer. In a particular embodiment, the outer cover 18 of mesh (FIG. 7), for example, has an outer surface comprising loops 44 (FIG. 7), that acts as a loop component of a hook-and-loop fastening system. A mesh construction, as shown in FIG. 7, has interconnected or weaved fibers 21 of material forming the outer cover 18. The loops 44 may be formed as part of the material of the outer cover 18 or otherwise disposed on the surface of the outer cover. A suitable material with such construction is a polyester mesh loop 2103 sold by Quanzhou Fulian Warp Knitting Industrial Co., Ltd. of Quanzhou City, China. Hook components 46 (FIG. 3) are attached to an inner surface of the inner layer 12 at the proximal, intermediate and distal flaps 41a, 41b, 41c, respectively. The loops 44 of the outer cover 18 allow the hook components 46 (FIG. 3) to be secured anywhere along the outer surface of the outer cover when the sleeve 10 is wrapped circumferentially around the limb of the wearer. This allows for sleeve 10 to be of a substantially one-size-fits-all configuration with respect to the circumferences of different wearers' limbs. Moreover, the outer cover 18 having the loops 44 allows the practitioner to quickly and confidently secure the sleeve 10 to the wearer's limb without needing to align the fastening components.

It is contemplated that the outer cover 18 may be capable of wicking fluid in addition to being breathable. For example, the outer cover 18 may be constructed of the same material as the inner layer 12 (e.g., Cool dry). In this way, the moisture wicked by the inner layer 12 may be wicked by the outer cover 18 through the openings 32 in the bladders 24a, 24b, 24c. The moisture will then spread out evenly across the outer cover 18 and is able to evaporate more readily than if the outer cover was not formed of a wicking material because a greater surface area of the outer cover, as opposed to the inner layer 12, is exposed to air. Alternatively, the cover can have a wicking material laced in or on top of outer layer.

Figure 13:
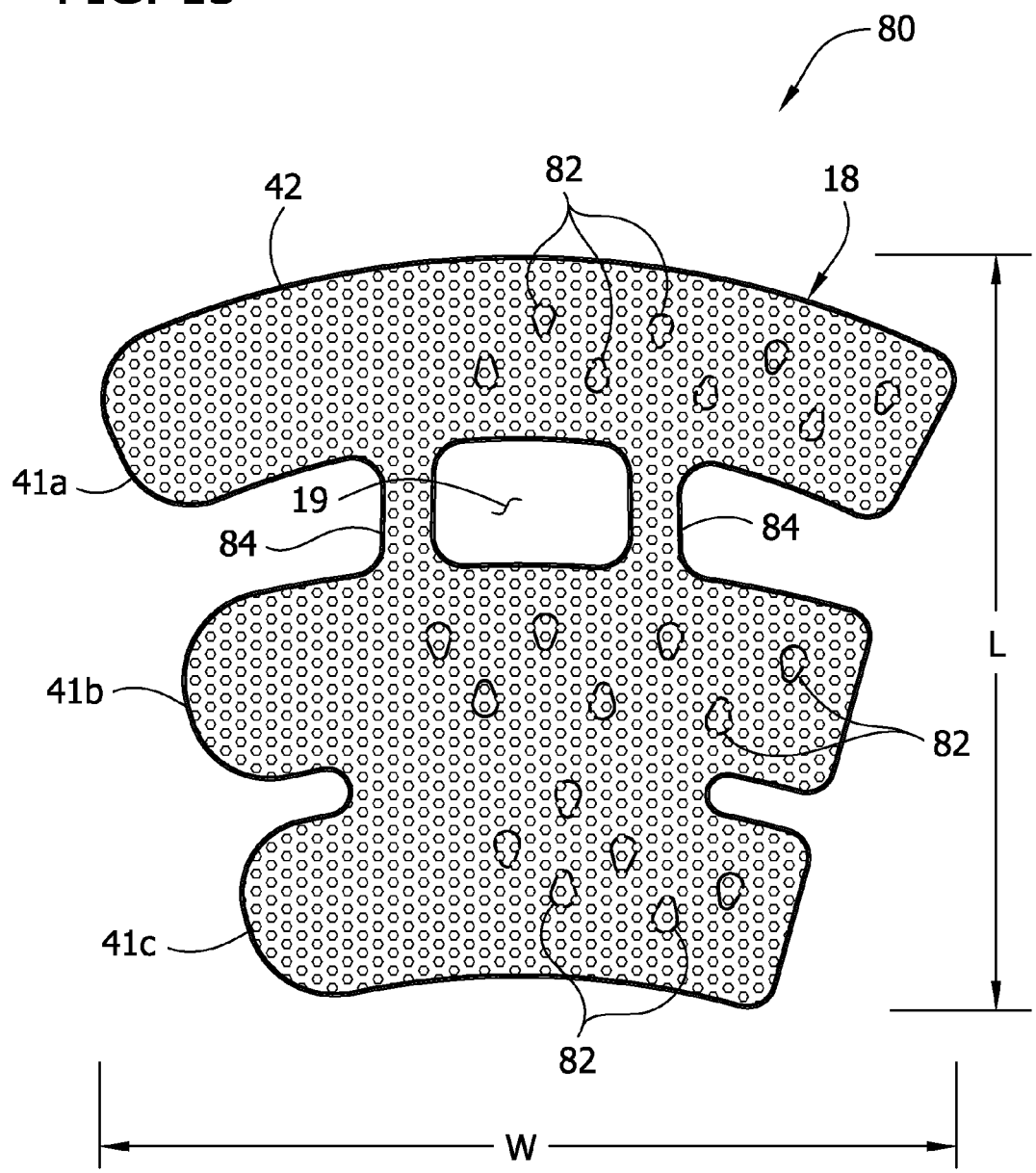
FIG. 13 is a front elevation of another embodiment of a compression sleeve.

Referring to FIG. 13, yet another embodiment of the sleeve is generally indicated at 80. The difference between this sleeve and the first embodiment 10 is that the inner layer 12 and the outer cover 18 are secured to each other at seam lines 82 through the openings 32 in the bladders 24a, 24b, and 24c to maintain the inner layer and outer cover in direct contact. In this embodiment, both the inner layer 12 and the outer cover 18 are constructed of suitable wicking material, such as CoolDry or CoolMax®. By being in constant contact, the outer cover 18 continuously wicks moisture from the inner layer 12 through the openings 32 in the bladders 24a, 24b, 24c. As explained above, in this way a larger surface area having wicked moisture is exposed to air and the wicked moisture can evaporate more quickly.

The compression sleeve 10 as a whole is more comfortable to wear because of the synergistic relationship of the layers 12, 14, 16, 18. For example, the inner layer 12 is capable of wicking moisture from the limb and allowing the moisture to evaporate out of the sleeve 10. As stated above, wicking involves transporting moisture away from the limb and moving moisture from locations where it is abundant and transporting it to areas where it is less abundant. Material decreases its wicking rate when the moisture is equally distributed in the wicking material and the wicking material is saturated. However, the breathability of the sleeve 10 allows for the wicked moisture to evaporate. The waterdrop-shaped openings 32 in the bladders 24a, 24b, 24c and the breathable outer cover 18 allow moisture in the inner layer 12 that is adjacent to the openings to evaporate therethrough. Accordingly, as the moisture evaporates, it is transported to the drier portions of the inner layer 12, and the inner layer is able to wick more moisture. Testing described below supports the findings of breathable outer cover improves the cooling affect to the patient. If one places the openings 32 at the corner points of a generally square pattern, then the middle of the square is theoretically the farthest distance trapped moisture must be wicked in terms of distance to an opening. The closer the openings are together the more rapidly the wicked moisture is evaporated because the distance to an opening is shortened. The further apart the openings, the greater the distance the wicked moisture must travel and the less comfort the device provides to the patient, in terms of cooling. The testing described below helped determine the optimum spacing and size to provide cooling without compromising blood flow as shown in FIG. 22.

Summarized in Table III are the evaporation test results of an embodiment constructed according to the principles of the present invention having the waterdrop-shaped opening as compared with competitor sleeves A and C.

TABLE III

Evaporation Rates by Sleeve

|  | Present Invention Waterdrop-shape | Prior Art SCD Express 9529 | Sleeve A | Sleeve C |
|---|---|---|---|---|
| Entire Sleeve Area (in²) | 280 | 264 | 210 | 198 |
| Available Bladder Area (in²) | 173 | 178 | 55 | 58 |
| % of Bladder Area | 61.8% | 67.4% | 26.2% | 29.3% |
| % of Open Area through Bladder of Entire Sleeve | 5.9% | 0.0% | 0.0% | 0.0% |
| Average Evaporation Rate (g/min) | 0.03268 | 0.00598 | 0.0424 | 0.03488 |
| Average Evaporation Rate per in² of Entire Sleeve (g/min/in²) | 0.00012 | 0.00002 | 0.00020 | 0.00018 |
| Average Evaporation Rate Vs. Bladder Coverage (g/min) | 0.02019 | 0.00403 | 0.01110 | 0.01022 |

For purposes of this application, the following test (referred to herein as the "static evaporation test") is used to determine the rate of evaporation of moisture wicked by the wicking layer through sleeve (e.g., through the openings, at the seam lines and/or the other portions of the bladder layers not overlying the wicking layer). The results are summarized in Table III. A polycarbonate plate is placed on a digital scale. The polycarbonate plate has a peripheral shape matching the peripheral shape of the sleeve to be tested, so that the sleeve may be superposed on the plate. The digital scale has a 2000 gram capacity with a 0.01 gram resolution. After the plate is placed on the scale, the scale is zeroed. Next, a mixture of room temperature tap water and food coloring (e.g., red food coloring) is sprayed onto the polycarbonate plate using a spray bottle. About 18 to 20 grams of the mixture is sprayed generally uniformly across the surface area of the plate. The sleeve to be tested is then placed on the plate so that the sleeve is generally flat on the plate and generally superposed thereon. The mass reading on the scale is recorded, along with the room temperature and the relative humidity. Every 30 minutes for at least 5 hours, the mass reading on the scale, the room temperature and the relative humidity are recorded. After completion of the test, with the sleeve still on the plate, a photograph of the underside of plate is taken to capture the distribution of any remaining fluid on the plate and the sleeve. Finally, using the recorded data, the evaporation rate and percentage of fluid evaporated by mass (e.g., mg/minute) for each sleeve is calculated.

Using the above-described static evaporation test, a sleeve of the type illustrated in FIG. 20 was tested. The same testing procedure can be applied to the other embodiments, such as the full length sleeve of FIG. 1. It was shown that moisture wicked by the inner layer of the sleeve was able to evaporate through each opening of the sleeve at a rate of between about 0.5 mg/minute and about 2.0 mg/minute and more specifically, between about 1.1 mg/minute and about 1.5 mg/minute. The overall rate of evaporation through all of the openings was between about 20 mg/minute and about 50 mg/minute and more specifically, between about 30 mg/minute and about 40 mg/minute. As explained above, in general the static evaporation test showed that increasing the percentage of the openings with respect to individual bladders increased the evaporation rate of the sleeve. The increase in evaporation rate did not increase proportionally above 30% total open percentage of the inner layer 12. It is also contemplated that using an inner layer that is capable of wicking fluid at a faster rate may also increase the evaporation rate of the sleeve. Other ways of increasing the evaporation rate of the sleeve are within the scope of the present invention.

The overall breathability of the sleeve 10 also aids in keeping the sleeve comfortable for the wearer. Because the inner layer 12, the bladders 24a, 24b, 24c and the outer cover 18 are breathable, the limb has access to air and heat is allowed to dissipate out of sleeve. The waterdrop-shaped openings 32, through their number and location along and around the sleeve, allow a significant amount of air to reach the limb and a significant amount of heat and moisture therein to be removed from the sleeve. This has the effect of keeping the limb cool and comfortable for the wearer.

The calculation of evaporation results, as found in Table III above is determined by the following equations:

% of liquid evaporated,$LEi=((Wsn-Wso)-(Wsn-1-Wso))/(Wsn-Wso)$,

Where LEi is the incremental % of liquid evaporated at a given data point;
Where Wsn is the weight of the sample at the desired data point;
Where Wsn−1 is the weight of the sample at the previous data point;
Where Wso is the original dry weight.

% of liquid evaporated,$LEc=[((Wsn-Wso)-(Wsn-1-Wso))/(Wsn-Wso)]\Sigma nLEi$,

Where ERc is the cumulative % of liquid evaporated;
Where Wsn is the weight of the sample at the desired data point;
Where Wsn−1 is the weight of the sample at the previous data point;
Where Wso is the original dry weight;
Where $\Sigma nLEi$ is the summation of the previous incremental % of liquid evaporated.

Evaporation Rate,$ER=(Wsn-1-Ws)/\Delta t$,

Where Wsn−1 is the weight of the sample at the previous data point;
Where Ws is the current weight of the sample;
Where Δt is the change in time between Wsn−1 and Ws.

To improve patient mobility, the sleeve was designed to have an elastic inner layer 12 and outer cover 18. An elastic sleeve improves comfort which increases patient compliance. Refer to FIGS. 1-7 for the discussion on elasticity below. An elastic device will conform to a patient's limb to ensure continuous wicking. A compliant or substantially conforming fit will help ensure the contact of the bladder against a patient's skin during use. The bladder applies the pressure to move the blood. The elastic outer layer helps reduce number of straps to hold the sleeve in place because the elastic outer layer 18 returns its original shape exerting a slight force against the patient's limb. This force helps hold the sleeve in place and also allows the practitioner not to over tighten a strap. Some prior art devices use an elastic stocking, such as the T.E.D.® stocking, beneath the compression sleeve. The compression sleeve of at least some embodiments avoids the two step process of first placing the compression stocking on the patient, then placing the sleeve over the stocking. Also sleeves of preferred embodiments of the present invention simplify the job of the nurses because there is no need to order a stocking and sleeve.

The Applicant devised an elasticity test for determining the amount of stretch around the limb and along the limb. A patient needs to be mobile during treatment. Prior art sleeves can be awkward, stiff and heavy so the user would remove the device, if they needed to move about. The need is to improve elasticity without distorting the openings 32 too much such as becoming elongated or causing an opening to overlie, which reduces its size for evaporation.

For example, the inner layer 12 is preferably elastically stretchable along the width W of the sleeve 10 so that the inner layer is able to conform circumferentially to the shape of the wearer's limb. Conforming circumferentially allows the inner layer 12 to remain in close, intimate and continuous contact with the wearer's limb to ensure that the inner layer is continuously wicking moisture from the limb. The inner layer 12 may also be stretchable the length L. Preferably, the inner layer 12 is elastically stretchable along both the width W and the length L of the sleeve and is more elastically stretchable along the length of the sleeve 10 than along the width. Summarizing the preferred approach, using the test described below, the inner layer 12 may have an average elasticity in the widthwise direction of the sleeve of between about 13 lbs/in (23 N/cm) and about 14 lbs/in (25 N/cm), and in one embodiment has an elasticity of about 13.3 lbs/in (23.3 N/cm). The inner layer 12 may have an average elasticity in the lengthwise direction of the sleeve of between about 0.5 lbs/in (0.9 N/cm) and about 0.7 lbs/in (1.2 N/cm), and in one embodiment has an elasticity of about 0.63 lbs/in (1.10 N/cm). The small openings 20 in the inner layer 12 also allow for the inner layer stretch more.

The outer cover 18 is also elastically stretchable along the length L of the sleeve 10 or stretchable along both lengthwise and widthwise (circumferentially). Preferably, the outer cover 18 is more elastic longitudinally than widthwise. Although elastically stretchable, the outer cover 18 acts to restrain the amount of expansion of the bladders 24a, 24b, 24c. The outer cover 18 helps to conform the bladder to the limb for helping to evenly apply pressure for moving blood. For example, using the elasticity test described below, the outer cover 18 may have an average elasticity in the widthwise direction of between about 13 lbs/in (23 N/cm) and about 15 lbs/in (26 N/cm), and in one embodiment has an elasticity of about 13.6 lbs/in (23.8 N/cm). The outer cover 18 may have an average elasticity in the longitudinally direction of between about 19 lbs/in (33 N/cm) and about 22 lbs/in (39 N/cm), and in one embodiment an elasticity of about 19.8 lbs/in (34.7 N/cm).

The compression sleeve 10 as a whole is stretchable longitudinally by way of the longitudinally stretchable inner layer 12, intermediate layers 14, 16 and outer cover 18. Further, the sleeve 10 is slightly stretchable widthwise by way of the abilities of the inner layer 12, intermediate layers 14, 16 and the cover 18 to stretch widthwise. The waterdrop-shaped openings 32 and the fact that the openings are offset widthwise also aid in the widthwise stretching.

It is common for patients that have undergone surgery to incur swelling of the limbs. The widthwise stretching of the sleeve 10 is more comfortable for patients that experience swelling because the sleeve will stretch, i.e., increase in size circumferentially, as the limb swells. Moreover, elasticity of the sleeve 10 allows the wearer to have more mobility of his or her limb and gives the practitioner a greater degree of freedom when wrapping the sleeve around a wearer's leg. For example, using the elasticity test described below, the thigh-length sleeve 10, comprising the inner layer 12, the intermediate layers 14, 16 and the outer cover 18 as described above, may have an average elasticity in the widthwise direction of between about 22 lbs/in (39 N/cm) and about 27 lbs/in (47 N/cm), and in one embodiment an elasticity of about 24.3 lbs/in (42.6 N/cm). The compression sleeve 10 may have an average elasticity in the lengthwise direction of between about 17 lbs/in (30 N/cm) and about 22 lbs/in (39 N/cm), and in one embodiment an elasticity of about 19.4 lbs/in (34.0 N/cm).

In another example, using the elasticity test described below, a knee-length sleeve, comprising an inner layer, intermediate layers and outer cover of the same material as the thigh-length sleeve described above, may have an average elasticity in the widthwise direction of between about 22 lbs/in (39 N/cm) and about 27 lbs/in (47 N/cm), and an average elasticity in the lengthwise direction of between about 33 lbs/in (58 N/cm) and about 40 lbs/in (70 N/cm).

The following test (herein referred to as the "elasticity test") is used to measure the elasticity of the layers 12, 14, 16 and 18 and the sleeve 10, both widthwise and lengthwise. First, structure clamps are secured to the structure (e.g., one of the layers 12, 14, 16, and 18 or the sleeve 10) to be tested. When testing the lengthwise elasticity, the structure clamps are secured to top and bottom edges of the structure. When testing the widthwise elasticity, the structure clamps are secured to opposite side edges of the structure. The sleeve sample with the structure clamps secured thereto is placed in a universal tensile testing machine (such as a universal testing machine manufactured by Instron® of Grove City, Pa.) by securing the structure clamps to opposing machine clamps of the machine. The machine should include a microprocessor having a tensile force measurement program used to control the machine and record measurements of force and displacement. Once the structure is secured in the machine, the opposing machine clamps are moved apart to a position that eliminates or minimizes the slack in the structure. This position is the initial position for all subsequent tests. The tensile force measurement program is then executed. The displacement of the sleeve sample as the machine clamps are moved apart should be uniform linear elongation and should not damage the structure. This displacement is set and maintained for each test repetition. The test is repeated 7 times for each layer 12, 14, 16 and 18 and the sleeve 10. Elasticity is calculated as force (lbs) divided by the displacement (in). An average elasticity of the 8 tests is calculated by summing the elasticity calculations for the 8 tests and dividing the sum by 8.

The sleeve in some embodiments is made more comfortable for the wearer by the fact that the inner layer 12 and the outer cover 18 are secured to the respective intermediate layers 14, 16 only adjacent to the outer peripheries of the inner layer and cover whereby the bladders 24a, 24b, 24c are not secure directly to the inner layer and cover. This construction allows for the bladders 24a, 24b, and 24c to move independently of the inner layer 12, and vice versa. Co-assigned U.S. patent application Ser. No. 11/299,568 disclosing an embodiment directed to reducing chafing of a person's skin during use is incorporated herein by reference.

Thus, when the sleeve 10 is wrapped circumferentially around the wearer's limb, the inner layer 12 substantially conforms to the contour or shape of the limb and will remain substantially stationary against the wearer's limb as the bladders 24a, 24b, 24c inflate and deflate and/or shift positions. The movement of the bladders 24a, 24b, 24c both as they inflate and deflate and shift positions relative to the limb may cause chaffing and other discomfort for the patient if the surface of the bladders continuously rubbed against the limb. However, by being secured only at the outer peripheries of the intermediate layers 14, 16, the inner layer 12 creates a buffer between the bladders 24a, 24b, 24c and the limb that prevents chaffing and other friction against the skin of the limb. The bladders 24a, 24b, 24c may move without causing corresponding movement of the inner layer 12 against the skin.

Figure 8:
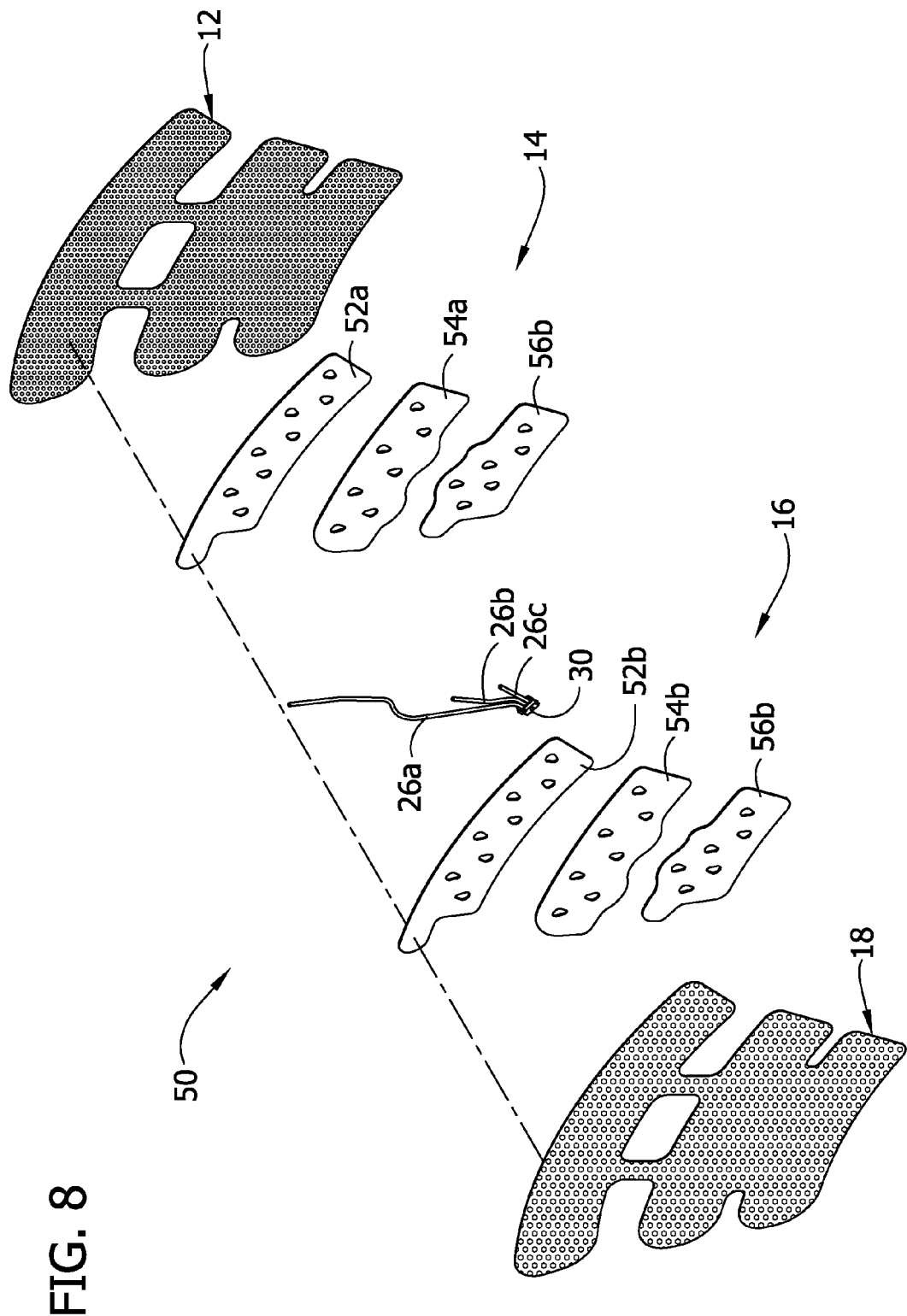
FIG. 8 is an exploded perspective of another embodiment of a compression sleeve.
Figure 9:
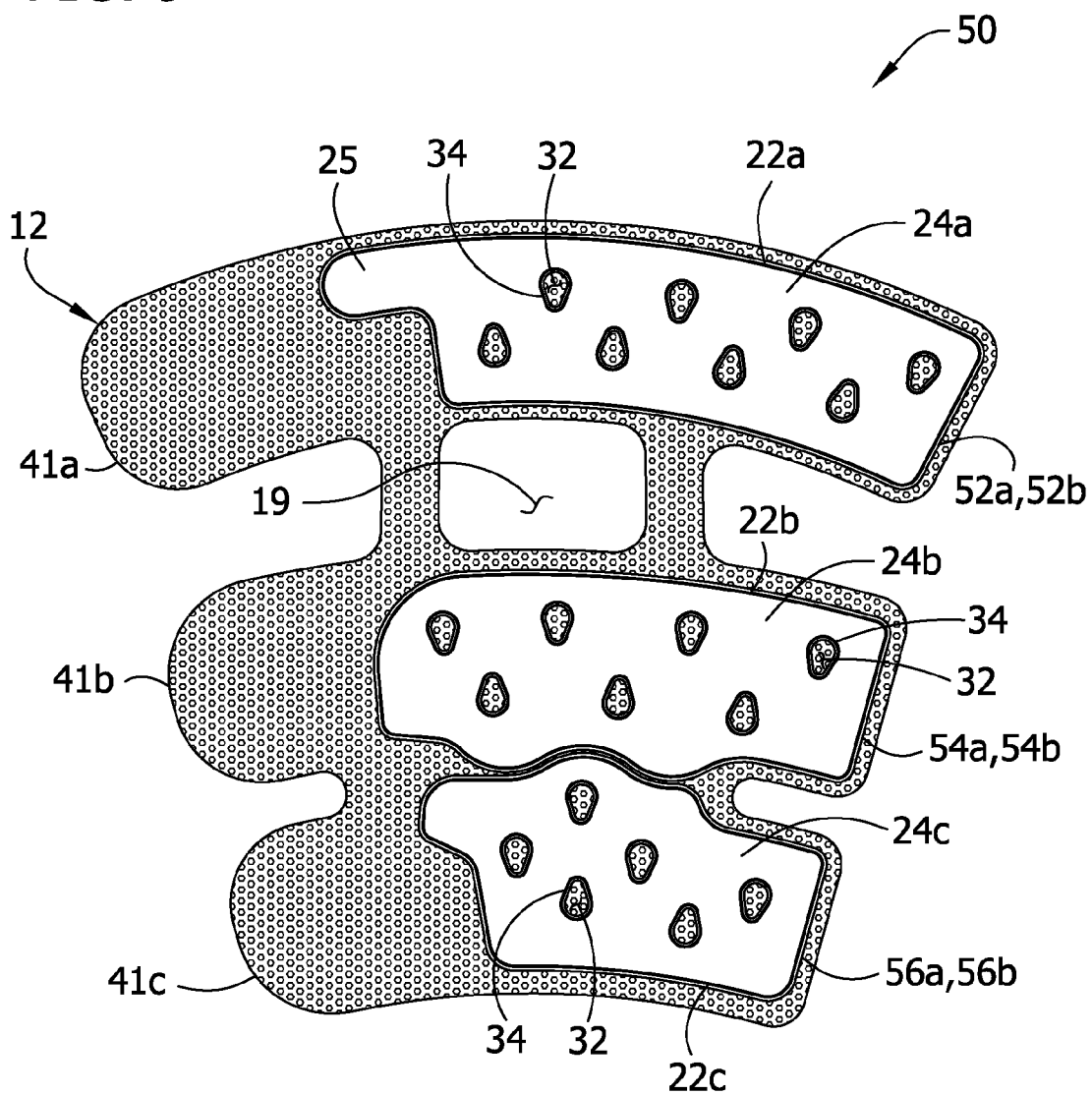
FIG. 9 is a front elevation of the compression sleeve of FIG. 8 with an outer cover removed.

Referring now to FIGS. 8 and 9, another embodiment of the sleeve is generally indicated at 50. This embodiment 50 is similar to the first embodiment 10, and therefore, corresponding parts will be indicated by corresponding reference numbers. The difference between the present embodiment 50 and the first embodiment 10 discussed above is that each of the intermediate layers 14, 16 comprises three separate sheets 52a, 54a, 56a and 52b, 54b, 56b, respectively. Corresponding intermediate sheets 52a, 52b and 54a, 54b and 56a, 56b, are secured together to form the three separate bladders 24a, 24b, 24c (FIG. 9). The remainder of the sleeve 50 is constructed similar to the first embodiment, including the intermediate sheets 52a, 54a, 56a and 52b, 54b, 56b being secured only adjacent to the respective peripheries of the outer cover 18 and the inner layer 12 so that the central portions of the bladders 24a, 24b, 24c are free from securement to the inner layer and outer cover. It is also contemplated that adjacent bladders 24a, 24b, 24c may be connected to each other by elastically stretchable material other than the inner layer 12.

In addition to the advantages given above with respect to the first embodiment 10 of the compression sleeve, the present embodiment 50 also allows for better fit to a given individual's leg because the ability of the sleeve to stretch longitudinally is dependent only on the stretchabilities of the inner layer 12 and cover 18. In one embodiment, the inner layer 12 and the outer cover 18 are more stretchable than the intermediate layers 14, 16, and in particular, more stretchable longitudinally than the inner layer and the outer cover. Thus, the sleeve 50 may stretch between the proximal and intermediate bladders 24a, 24b without shifting the locations of the bladders on the leg (i.e., the bladders remain in place). In one example, at least one of the inner layer 12 and outer cover 18 is not resilient so that the sleeve 50 retains its stretched form after stretching. In another example, at least one of the inner layer 12 and outer cover 18 is resilient so that the sleeve 50 returns to its original form after a stretching force is released. The ability of the sleeve 50 to elastically stretch allows for the practitioner to readily adjust the positions of the bladders with respect to the wearer's limb. It is also contemplated that another stretchable component or material, other than the inner layer and the outer cover, may connect adjacent bladders.

Figure 10:
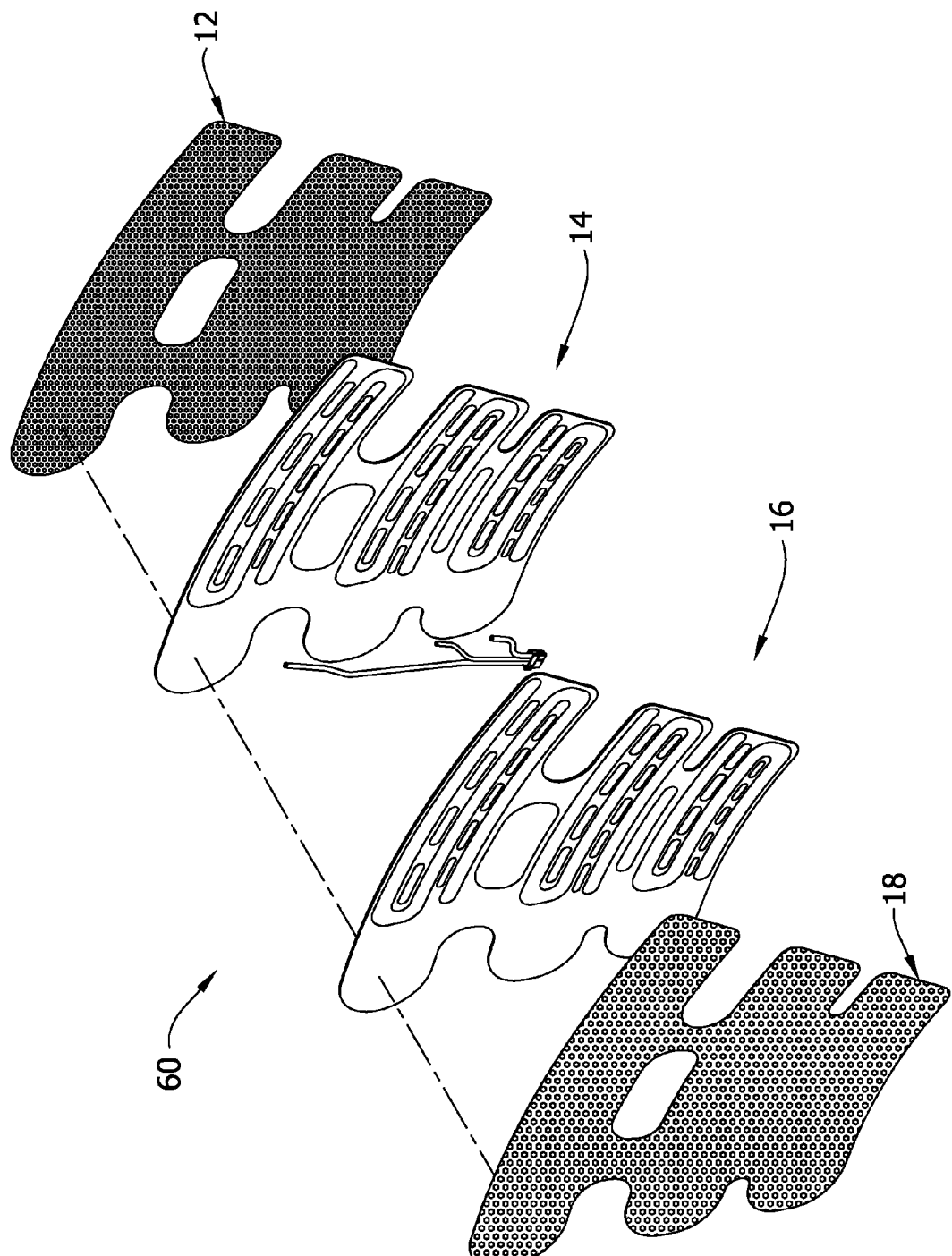
FIG. 10 is an exploded perspective of another embodiment of a compression sleeve.
Figure 11:
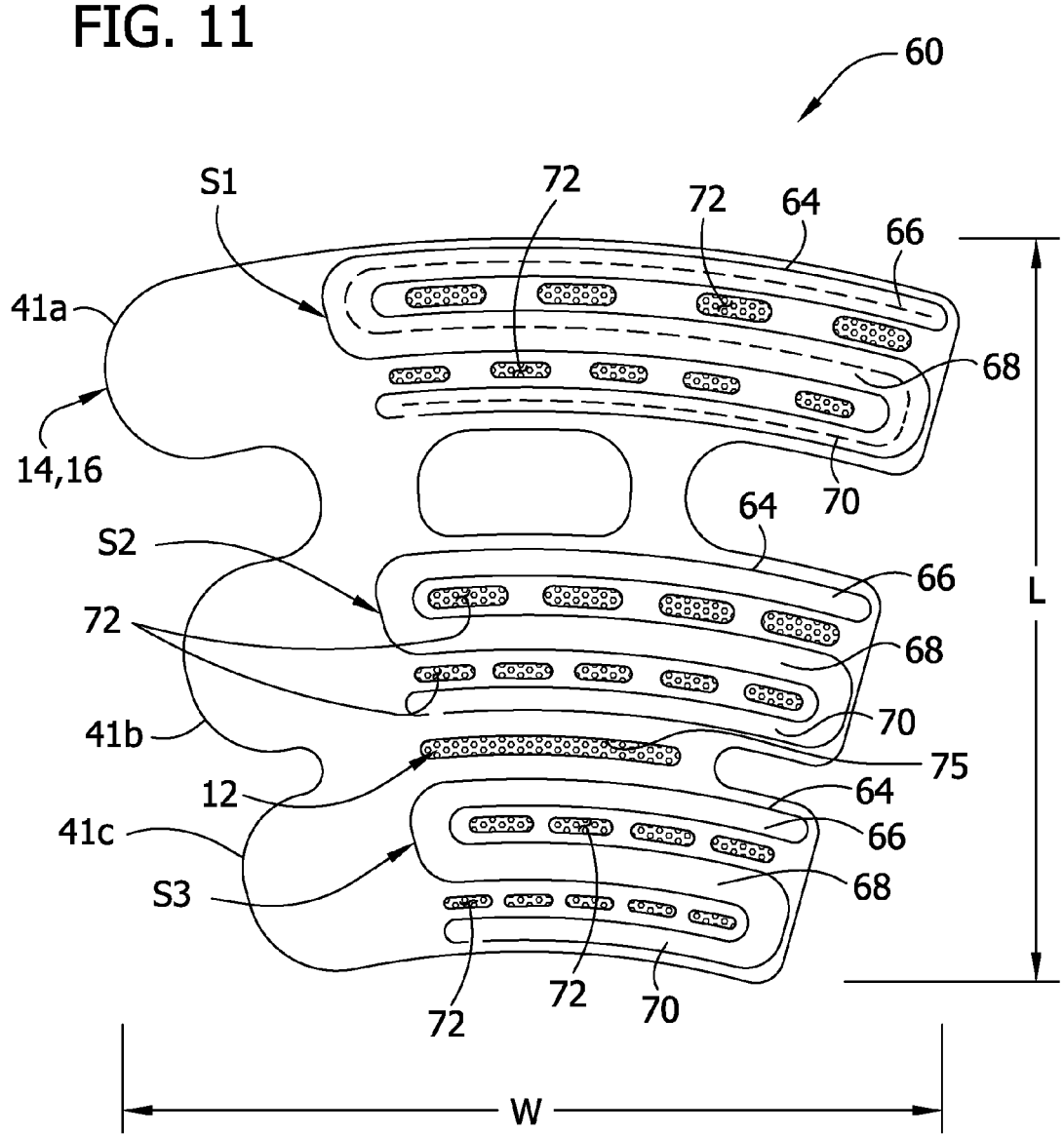
FIG. 11 is a front elevation of the compression sleeve of FIG. 10 with an outer cover removed.
Figure 12:
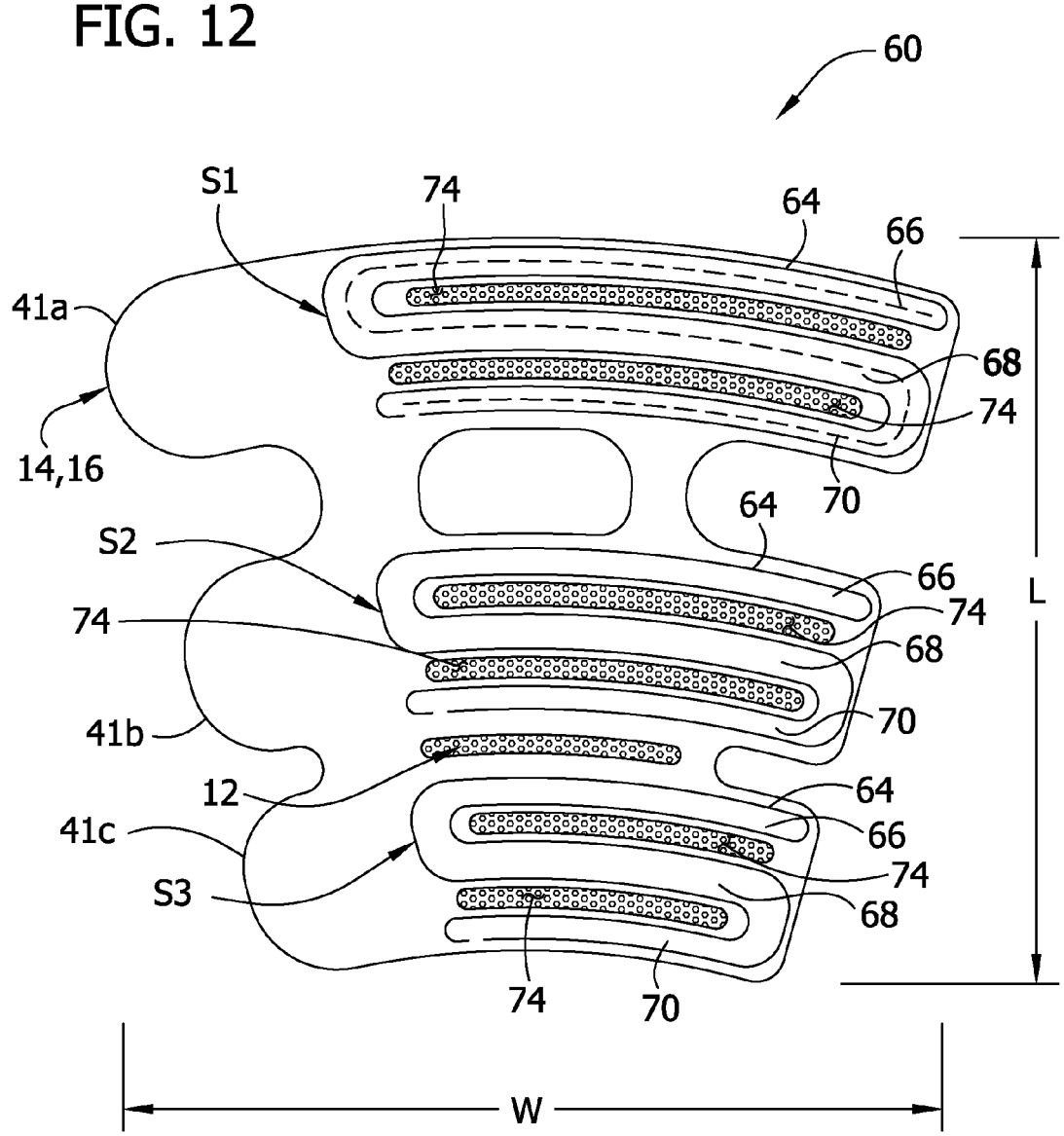
FIG. 12 is a front elevation of another embodiment of a compression sleeve, similar to the embodiment of FIG. 11, with an outer cover removed.

Referring to FIGS. 10-12, yet another embodiment of a compression sleeve is generally indicated at 60. Sleeve 60 is similar to the first embodiment, and therefore, like parts are indicated by corresponding reference numerals. The difference between this sleeve 60 and the first embodiment 10 is that inflatable bladders, generally indicated at S1, S2, S3 (FIG. 11), are generally S-shaped and do not include openings formed therethrough.

Each S-shaped bladder S1, S2, S3 is formed by securing the two intermediate layers 14, 16 together along an S-shape seam line 64. The S-shaped bladders S1, S2, S3 each include spaced apart proximal, intermediate and distal (or "first, second, and third") sections 66, 68, 70, respectively, along the length L of the sleeve 60. The general shapes of the bladders S1, S2, S3 are indicated by a centerline in FIG. 10. Holes 72 are formed through the intermediate layers 14, 16 between the proximal and intermediate portions 66, 68, respectively, of the bladders S1, S2, S3 and the intermediate portion and distal portion 70 of the bladders. Referring to FIG. 12, instead of numerous openings 72, continuous slits 74 may extend along the width of the sleeve 60 substantially the entirety of the length of the space between disposed between the proximal and intermediate portions 66, 68 and intermediate portion and distal portion 70 of each bladder S1, S2, S3. The openings/slits 72, 74 may be other shapes and sizes. Additional opening(s) may also be formed through the intermediate layers 14, 16 between the individual bladders S1, S2, S3 to make the sleeve 60 more breathable. For example, in the illustrated embodiment, an opening 75 is located between the bladders S2 and S3. Moreover, it is understood that the S-shaped bladders may include the openings (e.g., like openings 32) through the bladders S1, S2, S3 as shown in the first embodiment without departing from the scope of the invention. Alternatively, as with the sleeve 50 embodied in FIGS. 8 and 9, the bladders S1, S2, S3 may be formed separately from separate intermediate sheets and may be spaced apart longitudinally along the sleeve 60. The remainder of the sleeve 60 may be constructed in the same manner as described above with respect to the first and second embodiments.

The present sleeve 60 allows for large openings 72, 74, 75 to be formed through the intermediate layers 14, 16, thereby making the sleeve more breathable and allowing for more moisture to dissipate through the sleeve, without forming openings through the bladders S1, S2, S3. Openings 72, 74 in the sleeve 60 are spaced at smaller intervals along the length L of the sleeve without forming holes through the bladders S1, S2, S3 than if the bladders were not S-shaped.

In another embodiment shown in FIG. 14, the distal and intermediate bladders 24c, 24b, respectively, share a portion of their seam lines 22c, 22b, respectively. This portion of seam lines 22c, 22b is generally wavy so that portions of the intermediate bladder 24b are distal of adjacent portions of the distal bladder 24c, and correspondingly, portions of the distal bladder are proximal of adjacent portions of the intermediate bladder.

As is known in the art, the bladders 24a, 24b, 24c are pressurized to different pressures. For example, the distal bladder 24c is pressurized to a higher pressure than the intermediate bladder 24b. The wavy portion of the seam lines 22c, 22b creates a transition section defined by the wavy portion having a pressure that is between the high pressure of the distal bladder 24c and the lower pressure of the intermediate bladder 24b. The wavy transition section, in effect, avoids a region of essentially zero pressure and helps prevent pooling of blood between the adjacent bladders 24b, 24c. Industry studies performed by Nicolaides, Olson and Best all describe the importance of preventing the pooling of blood that can lead to venous stasis—a condition having a high occurrence of leading to a pulmonary embolism.

Referring now to FIG. 20, another embodiment of a compression sleeve is generally indicated at 200. This sleeve is a knee-length sleeve. The sleeve 200 is similar to the sleeve illustrated in FIGS. 1-7, and like parts are indicated by corresponding reference numerals plus 200. The sleeve 200 includes a wicking, breathable inner layer 212, intermediate layers 214, 216 defining three bladders 224a, 224b, 224c, and a breathable outer cover 218. Openings 232 are formed in each of the bladders 224a, 224b, 224c to allow moisture (e.g., moisture) wicked by the inner layer 212 to evaporate through the intermediate layers 214, 216 and the outer cover 218. The difference between the present sleeve 200 and the sleeve 10 illustrated in FIGS. 1-7 is that the present sleeve is sized and shaped to be received around the lower portion of the leg below the knee. Thus, the sleeve 200 does not have bridge members or a knee opening. Instead, the three bladders 224a, 224b, 224c are conjoined. It is understood that the sleeve 200 may have other configurations and/or characteristics, such as those described above in reference to other embodiments, without departing from the scope of the present invention.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A device for applying compression treatment to a part of a wearer's body, the device comprising:
    a wicking layer contacting skin on the wearer's body part when the device is mounted on the body part; and
    a bladder for selectively applying compression to the body part, the bladder comprising two sheets of air impermeable thermoplastic bladder material secured together and to the wicking layer along a weld having a thickness extending from the wicking layer through the thickness of the sheets of bladder material, wherein the wicking layer has uniformly distributed polymeric wicking fibers that extend through the thickness of the weld to allow fluid wicked from a wearer's skin to evaporate to the atmosphere.

2. The device of claim 1, wherein the wicking layer is a knitted sheet.

3. The device of claim 1, wherein the separate sheets of bladder material are secured to the wicking layer along a plurality of welds, one weld extending along a periphery of each sheet of bladder material.

4. The device of claim 3, wherein the wicking layer extends beyond the periphery of the sheets of bladder material.

5. The device of claim 1, wherein the weld is a spot weld.

6. The device of claim 1, wherein the thermoplastic bladder material has a polar molecule and the polymer of the polymeric wicking fibers has a non-polar molecule.

7. The device of claim 1, wherein the thermoplastic bladder material is PVC and the polymeric wicking fibers are polyester.

8. The device of claim 1, wherein the bladder extends around at least 90 percent of a median circumference of the wearer's body part.

9. The device of claim 1, further comprising an outer layer disposed on a side of the bladder away from the wearer's body part when the device is mounted on the body part, the outer layer secured to the thermoplastic bladder material and the wicking layer at the weld.

10. The device of claim 9, wherein the bladder defines a plurality of openings, and the wicking layer and the outer layer are secured to each other at the openings.

11. The device of claim 9, wherein the outer layer comprises woven fibers.

12. The device of claim 9, wherein the outer layer is a polyester mesh material treated with a hydrophilic material.

13. The device of claim 9, wherein at least one of the wicking layer and the outer layer is resilient.

14. A device for applying compression treatment to a part of a wearer's body, the device comprising:
    a wicking layer contacting skin on the wearer's body part when the device is mounted on the body part; and
    a bladder for selectively applying compression to the body part, the bladder comprising two sheets of polyvinyl chloride bladder material secured together and to the wicking layer along a weld having a thickness extending from the wicking layer through the thickness of the sheets of bladder material, wherein the wicking layer is a knitted sheet having polyester wicking fibers that extend through the thickness of the weld to allow fluid wicked from a wearer's skin to evaporate to the atmosphere.

15. The device of claim 14, wherein the separate sheets of bladder material are secured to the wicking layer along a plurality of welds, one weld extending along a periphery of each sheet of bladder material.

16. The device of claim 15, wherein the wicking layer extends beyond the periphery of the sheets of bladder material.

17. The device of claim 14, wherein the weld is a spot weld.

* * * * *